US010017480B2

(12) United States Patent
Bruno et al.

(10) Patent No.: US 10,017,480 B2
(45) Date of Patent: Jul. 10, 2018

(54) COMPOUNDS HAVING A SELECTIVE PDE4D INHIBITING ACTIVITY

(71) Applicants: UNIVERSITÀ DEGLI STUDI DI GENOVA, Genoa (IT); THE TRUSTEES OF COLUMBIA UNIVERSITY, New York, NY (US); MAASTRICHT UNIVERSITY, Maastricht (NL)

(72) Inventors: Olga Bruno, Genoa (IT); Chiara Brullo, Genoa (IT); Alessia Romussi, Genoa (IT); Ernesto Fedele, Genoa (IT); Roberta Ricciarelli, Genoa (IT); Ottavio Arancio, New York, NY (US); Jos Prickaerts, Maastricht (NL)

(73) Assignees: UNIVERSITA DEGLI STUDI DI GENOVA, Genoa (IT); THE TRUSTEES OF COLUMBIA UNIVERSITY, New York, NY (US); MAASTRICHT UNIVERSITY, Maastricht (NL)

(*) Notice: Subject to any disclaimer, the term of this patent is extended or adjusted under 35 U.S.C. 154(b) by 0 days.

(21) Appl. No.: 15/119,034

(22) PCT Filed: Feb. 10, 2015

(86) PCT No.: PCT/EP2015/052683
§ 371 (c)(1),
(2) Date: Aug. 15, 2016

(87) PCT Pub. No.: WO2015/121212
PCT Pub. Date: Aug. 20, 2015

(65) Prior Publication Data
US 2016/0355489 A1 Dec. 8, 2016

(30) Foreign Application Priority Data
Feb. 14, 2014 (EP) .................................. 14425015

(51) Int. Cl.
*C07D 207/34* (2006.01)
*C07D 207/337* (2006.01)
(Continued)

(52) U.S. Cl.
CPC ....... *C07D 261/04* (2013.01); *C07D 207/337* (2013.01); *C07D 207/34* (2013.01);
(Continued)

(58) Field of Classification Search
None
See application file for complete search history.

(56) References Cited

U.S. PATENT DOCUMENTS

| 4,684,652 A * | 8/1987 | Dubroeucq | C07D 211/26 514/211.15 |
| 2005/0075383 A1* | 4/2005 | Palle | C07D 498/10 514/378 |

(Continued)

FOREIGN PATENT DOCUMENTS

| WO | 2004094375 A2 | 11/2004 |
| WO | 2004094411 A1 | 11/2004 |

(Continued)

OTHER PUBLICATIONS

Bruno et al., "New Selective Phosphodiesterase 4D Inhibitors Differently Acting on Long, Short, and Supershort Isoforms",Journal of Medicinal Chemistry, 2009, vol. 52, No. 21, pp. 6546-6557.

(Continued)

*Primary Examiner* — Emily Bernhardt
(74) *Attorney, Agent, or Firm* — Lucas & Mercanti, LLP

(57) ABSTRACT

Compounds of formula (I), wherein Z=cyclopentyl. cyclopropylmethyl, —$CH_3$; R'=—$CH_3$, $CHF_2$, X=formula (II) (III) (IV) (V) Y=—CO; —C=O($CH_2$), —CH(OH)—$CH_2$, —$CH_2$—C=O, —$CH_2$—$CH_2$—C=O; —$CH_2$—CH(OH)—$CH_2$, —$CH_2$—CH(OCOR$_1$)—$CH_2$ NR$_2$= —N($CH_2$—$CH_2$OH)$_2$, formula (VI) (VII) (VIII) (IX) (X) (XI) R$_1$=optionally substituted $C_1$-$C_8$ alkyl, optionally substituted aryl; optionally substituted aralkyl, preferably $C_1$-$C_3$ alkyl, more preferably $CH_3$; and enantiomers, diastereoisomers and pharmaceutically acceptable salts thereof; these compounds have a PDE4D inhibiting activity and can be used as a medicament for treating dementia, in particular Alzheimer disease, and for improving memory.

(Continued)

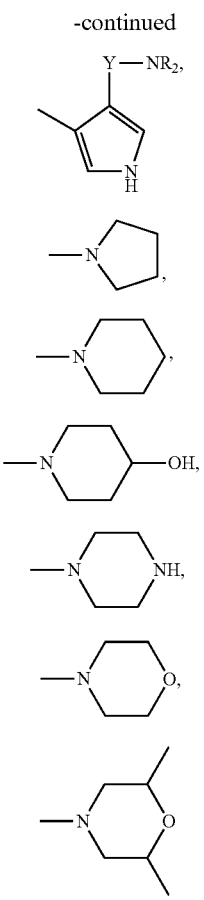

12 Claims, 4 Drawing Sheets

(51) Int. Cl.
*C07D 231/12* (2006.01)
*C07D 261/04* (2006.01)
*C07D 261/08* (2006.01)
*C07D 261/18* (2006.01)
*C07D 401/06* (2006.01)
*C07D 413/06* (2006.01)
*C07D 403/06* (2006.01)

(52) U.S. Cl.
CPC ......... *C07D 231/12* (2013.01); *C07D 261/08* (2013.01); *C07D 261/18* (2013.01); *C07D 401/06* (2013.01); *C07D 403/06* (2013.01); *C07D 413/06* (2013.01)

(56) References Cited

U.S. PATENT DOCUMENTS

| | | | | |
|---|---|---|---|---|
| 2006/0063772 | A1* | 3/2006 | Arora | C07D 261/08 514/253.1 |
| 2010/0105665 | A1* | 4/2010 | Kwok | C07D 233/90 514/218 |
| 2011/0112074 | A1* | 5/2011 | Follmann | C07D 413/14 514/217.05 |

FOREIGN PATENT DOCUMENTS

| | | |
|---|---|---|
| WO | 2005021515 A2 | 3/2005 |
| WO | 2008035315 A2 | 3/2008 |

OTHER PUBLICATIONS

Database Registry Chemical Abstracts Service, 2011, XP002723415, Database accession No. 1348351-21-2, Compound 1348351-21-2, Abstract. (1 page).
Database Registry Chemical Abstracts Service, 2006, XP002723416, Database accession No. 902289-52-5, Compound 902289-52-5, Abstract. (1 page).
Database Registry Chemical Abstracts Service, 2006, XP002723417, Database accession No. 902289-50-3, Compound 902289-50-3, Abstract (1 page).
Database Registry Chemical Abstracts Service, 2006, XP002723418, Database accession No. 899532-24-2, Compound 899532-24-2, Abstract (1 page).
International Search Report for International Application No. PCT/EP2015/052683. (4 pages) (dated Apr. 15, 2015).

* cited by examiner

COMPOUNDS HAVING A SELECTIVE PDE4D INHIBITING ACTIVITY

CROSS-REFERENCE TO RELATED APPLICATIONS

This application is a 371 of PCT/EP2015/052683, filed Feb. 10, 2015, which claims the benefit of European Patent Application No. 14425015.6, filed Feb. 14, 2014.

FIELD OF APPLICATION

The present invention concerns the technical field of the pharmaceutical industry.

In particular, the invention refers to new PDE4 inhibitors selective for type D isoform, which are able to improve cAMP release in hyppocampi and useful to restore memory impairments in neurodegenerative diseases, in particular Alzheimer Disease (AD), without side effects.

PRIOR ART

Dementia is a syndrome that can be caused by a number of progressive disorders and affects memory, thinking, behaviour and the ability to perform everyday activities. Alzheimer's disease (AD) is the most common type of dementia.

AD etiology and pathogenesis remain unclear, but many factors have been found to be implicated in AD. The dysregulation of some enzymatic systems (cholinesterases, phosphodiesterases) plays a pivotal role in cognitive symptoms. Another important etio-pathological factor is the alteration in Aβ amyloid levels and fibrils aggregation that cause neurons dead.

At the moment there are only five drugs available to attenuate memory deficits in Alzheimer's disease. In addition, all drugs (four acetylcholinesterase inhibitors and one NMDA antagonist) have limited efficacy and have severe side effects. Based on animal research, PDE inhibitors have been suggested as a promising target for the treatment of a variety of cognitive deficits and in particular memory impairment.

The cognitive process of memory consolidation strictly depends on cyclic adenosine monophosphate (cAMP) level in peculiar brain compartments. Indeed, a large body of evidence has shown that long term potentiation (LTP), the neurochemical substrate of learning and memory processes, requires the functioning of the cAMP/PKA/CREB pathway and its genetic or pharmacological manipulation can affect cognitive functions.

During the last decade, a large body of evidence has shown that cAMP enhancing compounds may benefit patients with Alzheimer Disease (AD). Phosphodiesterase 4 (PDE4) specifically controls the intracellular cAMP levels by hydrolyzing it to 5'-AMP.

In the last ten years several important studies demonstrated the pivotal role of phosphodiesterase type 4 (PDE4) in the synaptic function and memory, and evidenced that Rolipram (a well known unselective PDE4 inhibitor) is able to reverse the beta-amyloid induced dysfunction of the cAMP/PKA/CREB pathway, to restore hyppocampal LTP and to ameliorare cognitive deficits in a murine model of AD (Gong, Arancio O. et al, *J Clin. Invest.*, 2004; Rutten K., Prickaerts J. et al., *Neurobiol. of Learn and Mem.* 2008).

However, despite the potential clinical relevance, the therapeutic use of Rolipram is limited because of its major side effect of emesis. Since Rolipram inhibits all PDE4 isoforms, the Applicants wondered whether a more selective pharmacological strategy could avoid or overcome the side effects, still functioning on memory.

A very recent study on PDE4 knock-out mice indicates that PDE4D, and in particular PDE4D-D5 splice variants, play a critical role in the mediation of memory. This study also shows that the reduced expression of PDE4D4 and PDE4D5 enhances memory without causing emesis (Li Y F et al., *J. Neurosci.* 2011, 5, 172), thus strongly supporting the above hypothesis.

Finally, one of the Applicants recently published a study on a first PDE4D selective inhibitor (GEBR-7b), which increases memory function in mice and rats without emesis (Bruno et al, *Br. J. Pharm.*, 2011, 164:2054). In addition, they demonstrated that continuous prophylactic treatment with GEBR-7b can improve spatial memory in the APPswe/PS1dE9 mouse model of Alzheimer's disease (AD), even after the onset of the pathology, without altering emotional or neuroendocrine regulation [A.S.R. Sierksma et al., *Neuropharmacology*, 2014, 77:120].

O. Bruno et al., *Farmaco*, 2004, 59(3), 223, disclose certain 3-cyclopentyloxy-4-methoxybenzaldehyde and 3-cyclopentyloxy-4-methoxybenzoic acid derivatives as PDE4 inhibitors that can inhibit the neutrophil activation.

O. Bruno et al., *J. Med. Chem.* 2009, 52, 6546-6557, disclose 3-cyclopentyloxy-4-methoxybenzaldehyde derivatives as selective PDE4D inhibitors.

C. Brullo et al., *J. Med. Chem.* 2014, 57:7061, disclose new 3-cyclopentyloxy-4-methoxybenzaldehyde derivatives as selective PDE4D inhibitors.

The following dihydroisoxazolyl compounds are known from the Database Registry of the Chemical Abstracts:

RN 1348351-21-2: [3-[3-(cyclopentyloxy)-4-methoxyphenyl]-4,5-dihydro-5-isoxazolyl]-1-piperidinyl-methanone;

RN 902289-52-5: [3-(3,4-dimethoxyphenyl)-4,5-dihydro-5-isoxazolyl]-4-morpholinyl-methanone;

RN 902289-50-3: [3-(3,4-dimethoxyphenyl)-4,5-dihydro-5-isoxazolyl]-1-pyrrolidinyl-methanone;

RN 899532-24-2: [3-(3,4-dimethoxyphenyl)-4,5-dihydro-5-isoxazolyl]-1-piperidinyl-methanone.

No activity is disclosed for the above compounds.

WO 2005/021515 A2 discloses PDE4 inhibitors having the following formula:

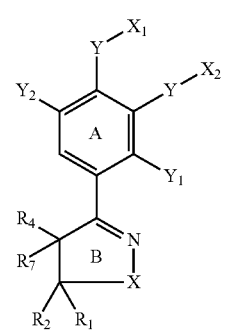

In particular, the following compounds are disclosed

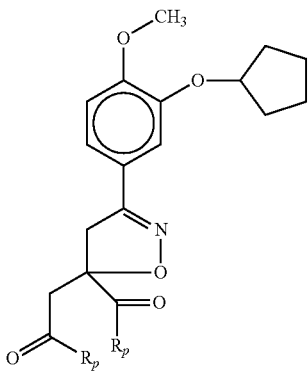

in which $R_p$ is a heterocyclyl or heteroaryl ring, in particular a pyrrolidinyl or piperidinyl ring.

SUMMARY OF THE INVENTION

The problem at the basis of the present invention has been to provide new compounds which are selective PDE4D inhibitors. These compounds are intended to find utility in preventing memory loss, which is one of the most severe disability in Alzheimer Disease (AD). In addition, the compounds provided by the present invention represent new pharmacological tools which could be of great relevance to increase the knowledge on the role of PDE4D isoforms in CNS functions, both under physiologic and pathologic conditions, particularly in AD.

The above-mentioned problem has been solved by compounds of the following formula (I),

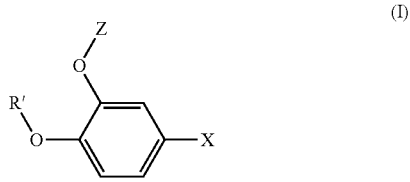

wherein:
Z=cyclopentyl, cyclopropylmethyl, —CH$_3$;
R'=—CH$_3$, CHF$_2$,
X=

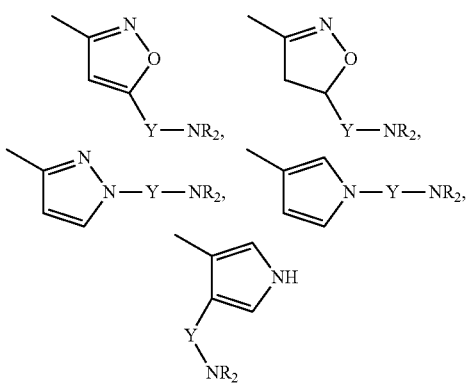

Y=—CO; —C=O(CH$_2$), —CH(OH)—CH$_2$, —CH$_2$—C=O, —CH$_2$—CH$_2$—C=O; —CH$_2$—CH(OH)—CH$_2$, —CH$_2$—CH(OCOR$_1$)—CH$_2$;
NR$_2$=—N(CH$_2$—CH$_2$OH)$_2$,

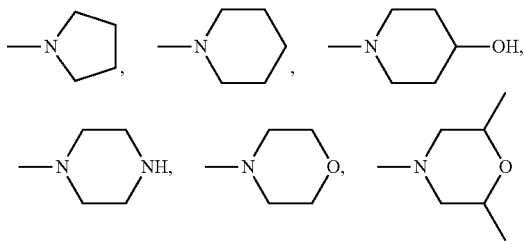

R$_1$=optionally substituted C$_1$-C$_8$ alkyl, optionally substituted aryl; optionally substituted aralkyl, preferably C$_1$-C$_3$ alkyl, more preferably CH$_3$;
with the proviso that, when Z=CH$_3$ and X=

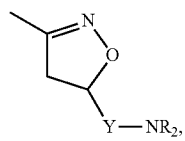

then Y is not —CO, and with the further proviso that, when Z=cyclopentyl and
X=

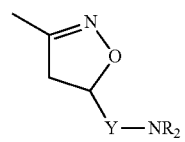

then Y—NR$_2$ is different from

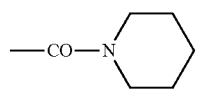

and by enantiomers, diastereoisomers and pharmaceutically acceptable salts thereof, The above-mentioned optionally substituted alkyl and aryl bear one or more substituents chosen from the group consisting of C$_1$-C$_3$ alkyl, halogen, C$_1$-C$_3$ alkoxy, hydroxy, SH, C$_1$-C$_3$alkylthio, nitro and haloalkyl.

C$_1$-C$_8$ alkyl indicates monovalent alkyl groups that have from one to eight carbon atoms; by way of example groups such as methyl, ethyl, n-propyl, isopropyl, n-butyl, isobutyl, terbutyl and the like are mentioned.

"Aryl" indicates aromatic carbocyclic groups having from 6 to 14 carbon atoms, with a single ring (e.g. phenyl) or with multiple condensed rings (e.g. naphthyl). Included among preferred aryls are phenyl, biphenyl, naphthyl, phenanthrenyl.

"Aralkyl" indicates an aryl as defined above bonded to an alkyl group having from 1 to 3 carbon atoms. Included among preferred aralkyls are benzyl, phenylethyl, naphthylmethyl, naphthylethyl.

Preferred are the compounds of formula (I) wherein:
Z=cyclopentyl
NR₂=

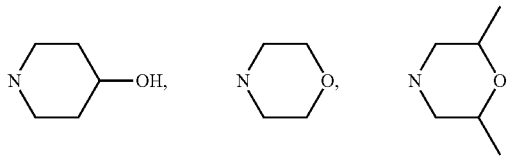

Particularly preferred are the compounds of formula (I) wherein:
Z=cyclopentyl
NR₂=

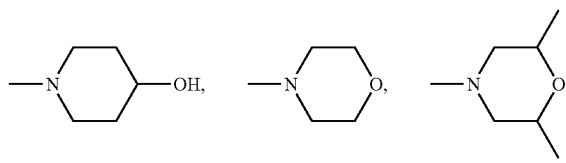

X=

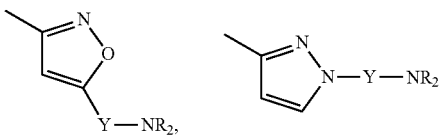

The most preferred compounds according to the present invention are those listed here below:
4-({3-[3-(Cyclopentyloxy)-4-methoxyphenyl]-4,5-dihydroisoxazol-5-yl}carbonyl)morpholine
4-({3-[3-(Cyclopentyloxy)-4-methoxyphenyl]-4,5-dihydroisoxazol-5-yl}carbonyl)-2,6-dimethylmorpholine
1-({3-[3-(Cyclopentyloxy)-4-methoxyphenyl]-4,5-dihydroisoxazol-5-yl}carbonyl)piperidin-4-ol
3-[3-(Cyclopentyloxy)-4-methoxyphenyl]-5-(pyrrolidin-1-ylcarbonyl)-4,5-dihydroisoxazole
3-[3-(Cyclopentyloxy)-4-methoxyphenyl]-N,N-bis(2-hydroxyethyl)-4,5-dihydroisoxazole-5-carboxamide
4-({3-[3-(Cyclopentyloxy)-4-methoxyphenyl]-4,5-dihydroisoxazol-5-yl}acetyl)morpholine
4-({3-[3-(Cyclopentiloxy)-4-methoxyphenyl]-4,5-dihydroisoxazol-5-yl}acetil) 2,6-dimethylmorpholine
1-({3-[3-(Cyclopentyloxy)-4-methoxyphenyl]-4,5-dihydroisoxazol-5-yl}acetyl)piperidin-4-ol
3-[3-(Cyclopentyloxy)-4-methoxyphenyl]-5-(2-oxo-2-pyrrolidin-1-ylethyl)-4,5-dihydroisoxazole
1-({3-[3-(Cyclopentyloxy)-4-methoxyphenyl]-4,5-dihydroisoxazol-5-yl}acetyl)piperidine
1-({3-[3-(Cyclopentyloxy)-4-methoxyphenyl]-4,5-dihydroisoxazol-5-yl}acetyl)piperazine
2-{3-[3-(Cyclopentyloxy)-4-methoxyphenyl]-4,5-dihydroisoxazol-5-yl}-N,N-bis(2-hydroxyethyl)acetamide
4-({3-[3-(Cyclopentyloxy)-4-methoxyphenyl]-4,5-dihydroisoxazol-5-yl}acetyl)morpholine
4-({3-[3-(Cyclopentyloxy)-4-methoxyphenil]-4,5-dihydroisoxazol-5-yl}acetil) 2,6-dimethylmorpholine
1-{3-[3-(Cyclopentyloxy)-4-methoxyphenyl]isoxazol-5-yl}-2-morpholin-4-ylethanone hydrochloride
1-{3-[3-(Cyclopentyloxy)-4-methoxyphenyl]isoxazol-5-yl}-2-(2,6-dimethylmorpholin-4-yl)ethanone hydrochloride
1-{3-[3-(Cyclopentyloxy)-4-methoxyphenyl]isoxazol-5-yl}-2-morpholin-4-ylethanol
1-{3-[3-(Cyclopentyloxy)-4-methoxyphenyl]isoxazol-5-yl}-2-(2,6-dimethylmorpholin-4-yl)ethanol
4-({3-[3-(Cyclopentyloxy)-4-methoxyphenyl]isoxazol-5-yl}carbonyl)morpholine
4-({3-[3-(Cyclopentyloxy)-4-methoxyphenyl]isoxazol-5-yl}carbonyl)-2,6-dimethylmorpholine
1-{3-[3-(Cyclopentyloxy)-4-methoxyphenyl]-1H-pyrazol-1-yl}-3-morpholin-4-ylpropan-2-ol dihydrocloride
1-{3-[3-(Cyclopentyloxy)-4-methoxyphenyl]-1H-pyrazol-1-yl}-3-(2,6-dimethylmorpholin-4-yl)propan-2-ol dihydrocloride
1-(3-(3-[3-(cyclopentyloxy)-4-methoxyphenyl]-1H-pyrazol-1-yl)-2-hydroxypropyl)piperidin-4-ol
2-{3-[3-(cyclopentyloxy)-4-methoxyphenyl]-1H-pyrazol-1-yl}-1-(morpholin-4-ylmethyl)ethyl acetate
4-({3-[3-(Cyclopentyloxy)-4-methoxyphenyl]-1H-pyrazol-1-yl}acetyl)morpholine
4-({3-[3-(Cyclopentyloxy)-4-methoxyphenyl]-1H-pyrazol-1-yl}acetyl)2,6-dimethylmorpholine
4-(3-{3-[3-(cyclopentyloxy)-4-methoxyphenyl]-1H-pyrazol-1-yl}propanoyl)molpholine
4-(3-{3-[3-(cyclopentyloxy)-4-methoxyphenyl]-1H-pyrazol-1-yl}propanoyl)2,6-dimethylmorpholine
4-(3-{3-[3-(cyclopentyloxy)-4-(difluoromethoxy)phenyl]-1H-pyrazol-1-yl}propanoyl)morpholine
1-(3-(3-(3-(cyclopentyloxy)-4-(difluoromethoxy)phenyl)-1H-pyrazol-1-yl)-2-hydroxypropyl)piperidin-4-ol
2-{3-[3-(cyclopentyloxy)-4-methoxy-phenyl]-pyrrol-1-yl}-1-morpholin-4-yl-ethanone
2-{3-[3-(Cyclopentyloxy)-4-methoxy-phenyl]-pyrrol-1-yl}-1-(2,6-dimethyl-morpholin-4-yl)-ethanone
2-{3-[3-(Cyclopentyloxy)-4-methoxy-phenyl]-pyrrol-1-yl}-1-(4-hydroxy-piperidin-1-yl)-ethanone
3-{3-[3-(cyclopentyloxy)-4-methoxy-phenyl]-pyrrol-1-yl}-1-morpholin-4-yl-propan-1-one
3-{3-[3-(Cyclopentyloxy)-4-methoxy-phenyl]-pyrrol-1-yl}-1-(4-hydroxy-piperidin-1-yl)-propan-1-one
1-{3-[3-(Cyclopentyloxy)-4-methoxy-phenyl]-pyrrol-1-yl}-3-morpholin-4-yl-propan-2-ol
1-{3-[3-(Cyclopentyloxy)-4-methoxy-phenyl]-pyrrol-1-yl}-3-(2,6-dimethyl-morpholin-4-yl)-propan-2-ol
1-(3-{3-[3-(cyclopentyloxy)-4-methoxy-phenyl]-pyrrol-1-yl}-2-hydroxy-propyl)-piperidin-4-ol
{4-[3-(Cyclopentyloxy)-4-methoxy-phenyl]-1H-pyrrol-3-yl}-morpholin-4-yl-methanone
{4-[3-(Cyclopentyloxy)-4-methoxy-phenyl]-1H-pyrrol-3-yl}-(2,6-dimethyl-morpholin-4-yl)-methanone
{4-[3-(Cyclopentyloxy)-4-methoxy-phenyl]-1H-pyrrol-3-yl}-(4-hydroxy-piperidin-1-yl)-methanone.

The present invention also provides compounds of of formula (I),

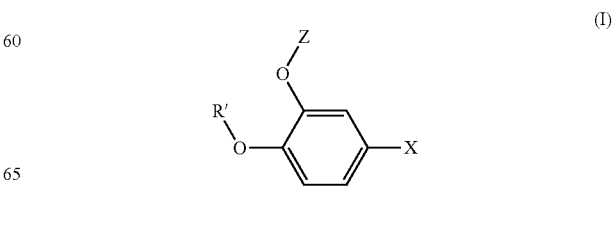

wherein:
Z=cyclopentyl, cyclopropylmethyl, —CH₃;
R'=—CH₃, CHF₂,
X=

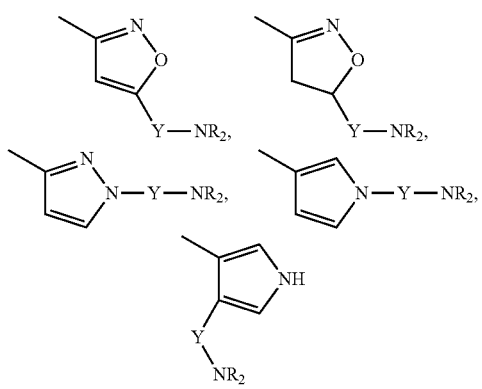

Y=—CO; —C=O(CH₂), —CH(OH)—CH₂, —CH₂—C=O, —CH₂—CH₂—C=O; —CH₂—CH(OH)—CH₂, —CH₂—CH(OCOR₁)—CH₂;
NR₂=—N(CH₂—CH₂OH)₂,

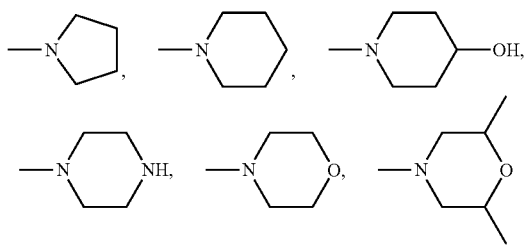

R₁=optionally substituted C₁-C₈ alkyl, optionally substituted aryl; optionally substituted aralkyl, preferably C₁-C₃ alkyl, more preferably CH₃;

and enantiomers, diastereoisomers and pharmaceutically acceptable salts thereof, for use as a medicament.

In particular the following compound is provided for use as a medicament:
1-({3-[3-(Cyclopentyloxy)-4-methoxyphenyl]-4,5-dihydroisoxazol-5-yl}carbonyl)piperidine.

The present invention also concerns a process for the production of the above-mentioned compounds of formula (I), in which Z=cyclopentyl,
X=

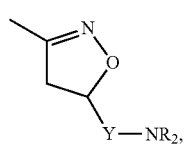

Y=—CH₂—C=O, and R', NR₂ and R₁ are as defined above, from now on identified as compounds of formula (Ia), comprising the reaction of a compound of formula (II)

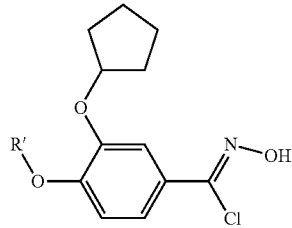

with a compound of formula (III):

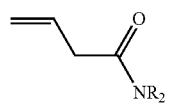

to yield the following compound of formula (Ia)

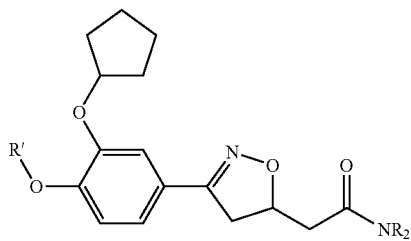

The present invention also relates to a process for the preparation of the above-mentioned compounds of formula (I), in which Z=cyclopentyl,
X=

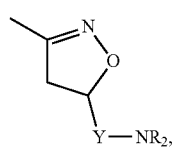

Y=—C=O, and R', NR₂ and R₁ are as defined above, from now on identified as compounds of formula (Ib), comprising the reaction of a compound of formula (IV):

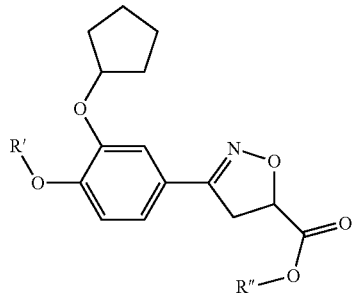

wherein R" is C₁-C₄ alkyl with R$_2$NH, wherein NR$_2$ is as defined above, to yield the following compound of formula (Ib));

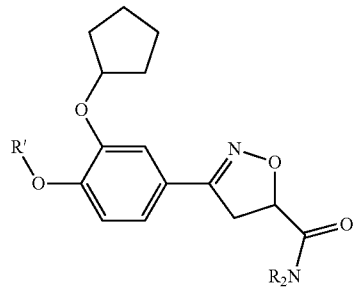
(Ib)

The present invention also concerns a process for the preparation of the above-mentioned compounds of formula (I), in which Z=cyclopentyl,
X=

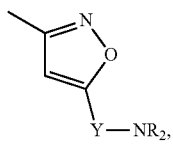

Y=—C=O, and R', NR$_2$ and R$_1$ are as defined above, from now on identified as compounds of formula (Ic), comprising the reaction of a compound of formula (V)

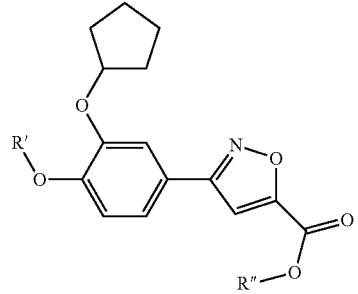
(V)

wherein R" is C$_1$-C$_4$ alkyl,
with R$_2$NH, wherein NR$_2$ is as defined above, to yield the following compound of formula (Ic)

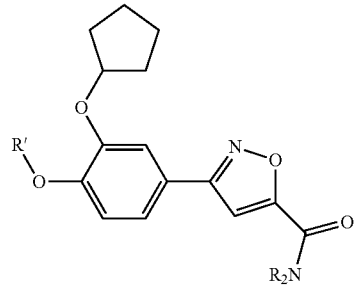
(Ic)

The present invention further concerns a process for the preparation of the above-mentioned compounds of formula (I), in which
Z=cyclopentyl, X=

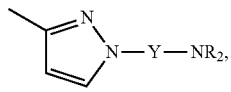

Y=—CH$_2$—CH(OH)—CH$_2$, and R', NR$_2$ and R$_1$ are as defined above, from now on identified as compounds of formula (Id), comprising the reaction of a compound of formula (VI):

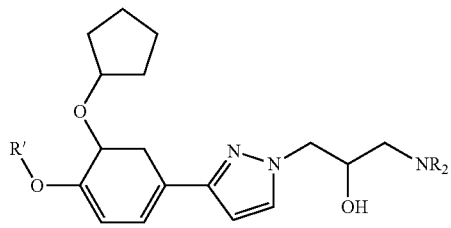
(VI)

with R$_2$NH, wherein NR$_2$ is as defined in claim 1, to yield the following compound of formula (Id)

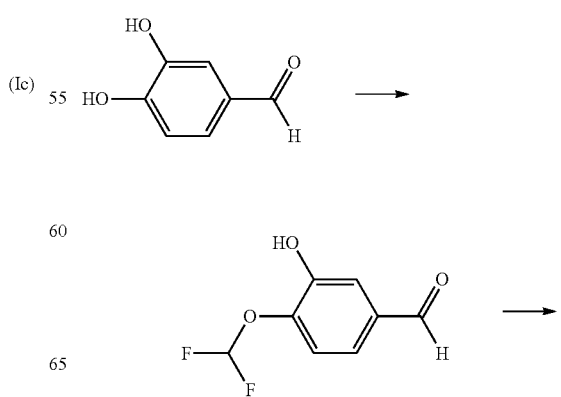
(Id)

In the latter process, for the case in which R' is —CHF$_2$, the relevant intermediate compound of formula (VIa) is prepared according to the following reaction scheme:

-continued

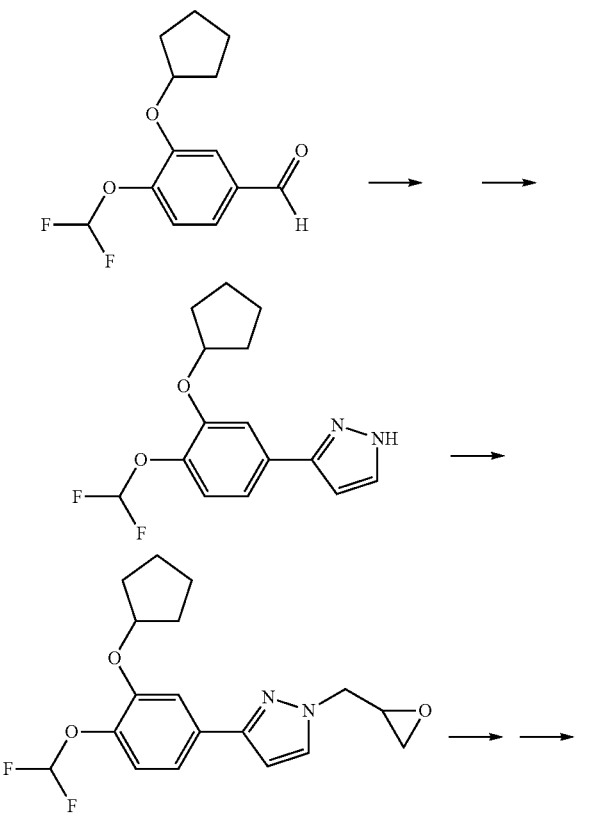

(VIa)

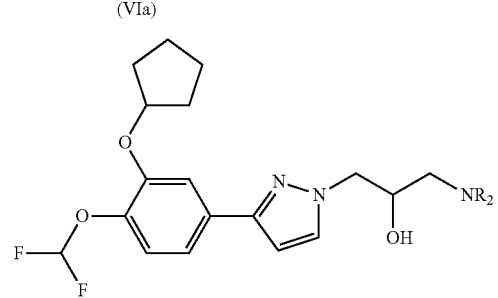

wherein the first step of converting 3,4-dihydroxybenzaldehyde into 4-(difluoromethoxy)-hydroxybenzaldehyde involves the reaction of 3,4-dihydroxybenzaldehyde with an ester of chlorodifluoroacetic acid, preferably methyl chlorodifluoroacetate in the presence of $Cs_2CO_3$ under irradiation with microwaves at a potency lower or equal to 300 W.

The present invention further concerns a process for the preparation of a compound according to any one of claims 1 to 5, in which Z=cyclopentyl, X=

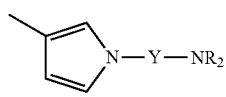

Y=—$CH_2$—C=O or —$CH_2$—$CH_2$—C=O, and R', $NR_2$ and $R_1$ are as defined in claim 1, comprising the reaction of a compound of formula (VII)

(VII)

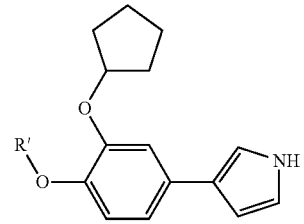

with a compound of formula J-$(CH_2)_m$—$CONR_2$, in which J=halogen, preferably Br or Cl, m=1 or 2 and $NR_2$ is as defined in claim 1, to yield the following compound of formula (XXIII) or (XXIV):

(XXIII) or (XXIV)

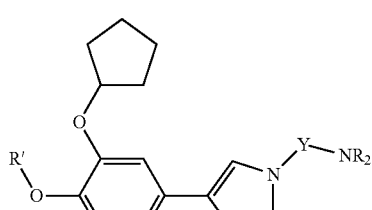

wherein R' and $NR_2$ are as defined in claim 1 and Y=—$CH_2$—C=O or —$CH_2$—$CH_2$—C=O.

The present invention also concerns a process for the preparation of a compound according to any one of claims 1 to 5, in which Z=cyclopentyl, X=

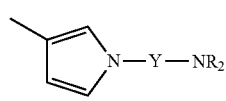

Y=$CH_2$—CH(OH)—$CH_2$, and R', $NR_2$ and $R_1$ are as defined in claim 1, comprising the reaction of a compound of formula (VIII):

(VIII)

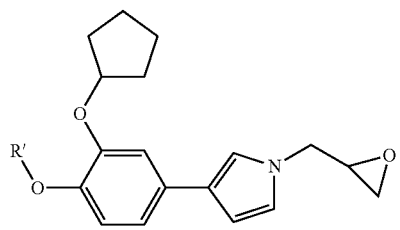

with $R_2NH$, wherein $NR_2$ is as defined in claim 1, to yield the following compound of formula (XXV):

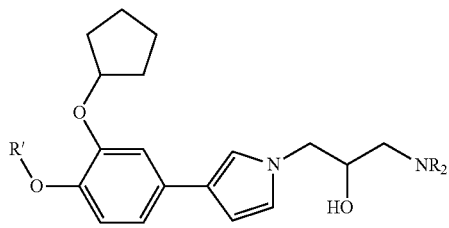

(XXV)

The present invention further concerns a process for the preparation of a compound according to any one of claims 1 to 5, in which
Z=cyclopentyl, X=

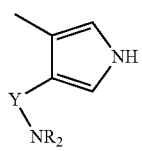

Y=—CO and R', $NR_2$ and $R_1$ are as defined in claim 1, comprising the reaction of a compound of formula (IX)

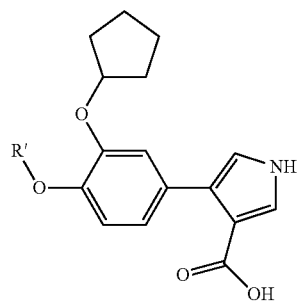

(IX)

with $R_2NH$, wherein $NR_2$ is as defined in claim 1, to yield the following compound of formula (XXVI)

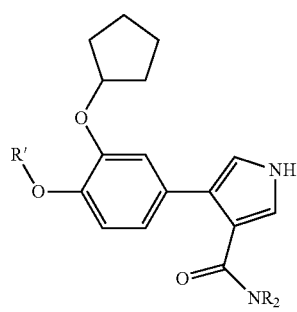

(XXVI)

The present invention further concerns the compounds of formula (I) as defined above and their enantiomers, diastereoisomers and pharmaceutically acceptable salts, for use as a medicament with PDE4D inhibiting activity.

The invention further concerns such compounds of formula (I) for use as a medicament for the treatment of dementia, in particular Alzheimer disease.

The invention further concerns such compounds of formula (I) for use as a medicament for enhancing memory.

The present invention further refers to a pharmaceutical composition comprising a compound of formula (I) as defined above or an enantiomer or diastereoisomer or pharmaceutically acceptable salt thereof and a pharmaceutically acceptable carrier.

Examples of pharmaceutically acceptable salts are those formed with organic acids such as oxalic, tartaric, maleic, succinic and citric and with inorganic acids such as nitric, hydrochloric, sulphuric and phosphoric.

The compounds according to the invention that have one or more asymmetric carbon atoms may exist as pure enantiomers, as pure diastereoisomers, as racemic mixtures of enantiomers, racemates and mixtures of racemates.

The compounds and compositions according to the invention may be administered with any available and efficient delivery system, comprising, but not limited to, oral, buccal, parenteral, inhalatory routes, topical application, by injection, by transdermic or rectal route (for ex. by means of suppositories) in dosage unit formulations containing conventional, pharmaceutically acceptable and non-toxic carriers, adjuvants and vehicles. The administration by parenteral route comprises subcutaneous, intravenous, intramuscular, intrasternal injection or infusion techniques.

The solid dosage forms for the administration by oral route comprise, for example, capsules, tablets, powders, granules and gels. In such solid dosage forms, the active compound may be mixed with at least one inert diluent such as, for example, sucrose, lactose or starch. These dosage forms normally also comprise additional substances different from the inert diluents, such as, for example, lubricating agents like magnesium stearate.

The injectable preparations, for example aqueous or oily sterile injectable solutions or suspensions, may be formulated according to the known technique and by optionally using appropriate dispersing, wetting and/or suspending agents.

The pharmaceutical preparations according to the present invention may be produced by using conventional pharmaceutical techniques, as described in the various pharmacopoeias or handbooks of the field such as, for example, "Remington's Pharmaceutical Sciences Handbook", Mack Publishing, New York, 18th Ed., 1990.

The average daily dosage of the compounds according to the present invention depends on many factors, such as, for example, the seriousness of the disease and the conditions of the patient (age, weight, sex): The dose may generally vary from 1 mg to 1500 mg per day of compound according to the invention, optionally divided into more administrations.

DETAILED DESCRIPTION

Figure 1:
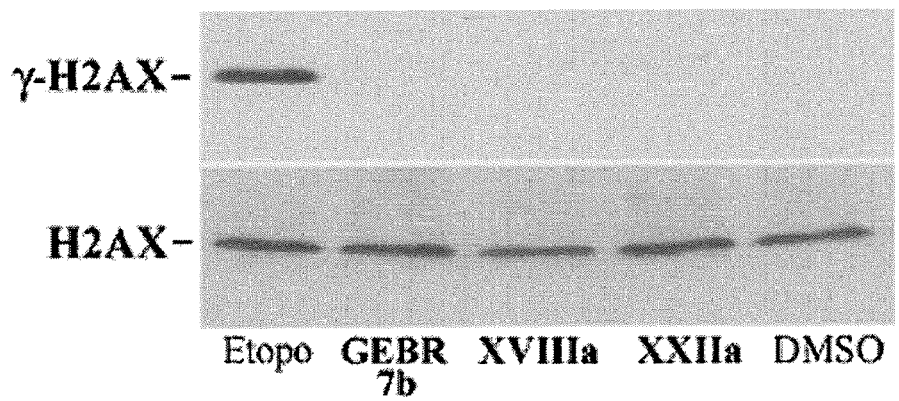
FIG. 1 is a Western blot analysis of γ-H2AX in HTLA cells treated with 100 μM etoposide, compounds XVIIIa and XXIIa according to the present invention, reference lead compound GEBR-7b, or an equal volume of solvent (DMSO).

The present invention will be further described by referring to some examples of preparation of compounds according to the invention and of evaluation of their activity.

Among the compounds according to the present invention, those indicated in the following table are mentioned in particular.

| | R' | X | Y | NR$_2$ |
|---|---|---|---|---|
| XIIIa | CH$_3$ | 4,5-dihydroisoxazol-5-yl (3-methyl), Y—NR$_2$ at 5-position | —C=O | morpholino |
| XIIIb | CH$_3$ | 4,5-dihydroisoxazol-5-yl (3-methyl), Y—NR$_2$ at 5-position | —C=O | 2,6-dimethylmorpholino |
| XIIIc | CH$_3$ | 4,5-dihydroisoxazol-5-yl (3-methyl), Y—NR$_2$ at 5-position | —C=O | 4-hydroxypiperidin-1-yl |
| XIIId | CH$_3$ | 4,5-dihydroisoxazol-5-yl (3-methyl), Y—NR$_2$ at 5-position | —C=O | pyrrolidin-1-yl |
| XIIIe | CH$_3$ | 4,5-dihydroisoxazol-5-yl (3-methyl), Y—NR$_2$ at 5-position | —C=O | piperidin-1-yl |
| XIIIf | CH$_3$ | 4,5-dihydroisoxazol-5-yl (3-methyl), Y—NR$_2$ at 5-position | —C=O | N,N-bis(2-hydroxyethyl)amino |
| XIVa | CH$_3$ | 4,5-dihydroisoxazol-5-yl (3-methyl), Y—NR$_2$ at 5-position | CH$_2$CO | morpholino |
| XIVb | CH$_3$ | 4,5-dihydroisoxazol-5-yl (3-methyl), Y—NR$_2$ at 5-position | CH$_2$CO | 2,6-dimethylmorpholino |

-continued

| | R' | X | Y | NR₂ |
|---|---|---|---|---|
| XIVc | CH₃ | 3-methylisoxazoline-5-yl-Y-NR₂ | CH₂CO | N-piperidinyl-4-OH |
| XIVd | CH₃ | 3-methylisoxazoline-5-yl-Y-NR₂ | CH₂CO | pyrrolidin-1-yl |
| XIVe | CH₃ | 3-methylisoxazoline-5-yl-Y-NR₂ | CH₂CO | piperidin-1-yl |
| XIVf | CH₃ | 3-methylisoxazoline-5-yl-Y-NR₂ | CH₂CO | piperazin-1-yl (4-NH) |
| XIVg | CH₃ | 3-methylisoxazoline-5-yl-Y-NR₂ | CH₂CO | —N(CH₂CH₂OH)₂ |
| XVa | CH₃ | 3-methylisoxazol-5-yl-Y-NR₂ | —C=O(CH₂) | morpholin-4-yl |
| XVb | CH₃ | 3-methylisoxazol-5-yl-Y-NR₂ | C=O(CH₂) | 2,6-dimethylmorpholin-4-yl |
| XVIa | CH₃ | 3-methylisoxazol-5-yl-Y-NR₂ | —CH(OH)CH₂ | morpholin-4-yl |
| XVIb | CH₃ | 3-methylisoxazol-5-yl-Y-NR₂ | —CH(OH)CH₂ | 2,6-dimethylmorpholin-4-yl |
| XVIIa | CH₃ | 3-methylisoxazol-5-yl-Y-NR₂ | —C=O | morpholin-4-yl |

-continued

| | R' | X | Y | NR₂ |
|---|---|---|---|---|
| XVIIb | CH₃ | 3-methylisoxazol-5-yl (Y—NR₂ at 5-position) | —C=O | 2,6-dimethylmorpholin-4-yl |
| XVIIIa | CH₃ | 3-methylpyrazol-1-yl (N—Y—NR₂) | CH₂CH(OH)CH₂ | morpholin-4-yl |
| XVIIIb | CH₃ | 3-methylpyrazol-1-yl (N—Y—NR₂) | CH₂CH(OH)CH₂ | 2,6-dimethylmorpholin-4-yl |
| XVIIIc | CH₃ | 3-methylpyrazol-1-yl (N—Y—NR₂) | CH₂CH(OH)CH₂ | 4-hydroxypiperidin-1-yl |
| XIX | CH₃ | 3-methylpyrazol-1-yl (N—Y—NR₂) | CH₂CH(OCOCH₃)CH₂ | morpholin-4-yl |
| XXa | CH₃ | 3-methylpyrazol-1-yl (N—Y—NR₂) | CH₂CO | morpholin-4-yl |
| XXb | CH₃ | 3-methylpyrazol-1-yl (N—Y—NR₂) | CH₂CO | 2,6-dimethylmorpholin-4-yl |
| XXIa | CH₃ | 3-methylpyrazol-1-yl (N—Y—NR₂) | CH₂CH₂CO | morpholin-4-yl |
| XXIb | CH₃ | 3-methylpyrazol-1-yl (N—Y—NR₂) | CH₂CH₂CO | 2,6-dimethylmorpholin-4-yl |
| XXIIa | CHF₂ | 3-(difluoromethyl)pyrazol-1-yl (N—Y—NR₂) | CH₂CH(OH)CH₂ | morpholin-4-yl |
| XXIIc | CHF₂ | 3-(difluoromethyl)pyrazol-1-yl (N—Y—NR₂) | CH₂CH(OH)CH₂ | 4-hydroxypiperidin-1-yl |
| XXIIIa | CH₃ | 4-methylpyrrol-1-yl (N—Y—NR₂) | CH₂CO | morpholin-4-yl |

-continued
| | R' | X | Y | NR₂ |
|---|---|---|---|---|
| XXIIIb | CH₃ | 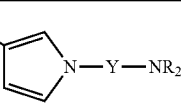 | CH₂CO | 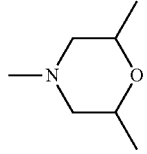 |
| XXIIIc | CH₃ | 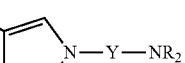 | CH₂CO | 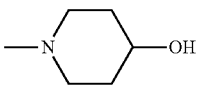 |
| XXIVa | CH₃ | 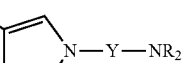 | CH₂CH₂CO | 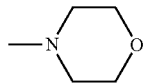 |
| XXIVc | CH₃ | 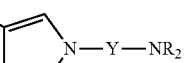 | CH₂CH₂CO | 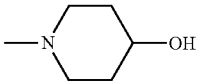 |
| XXVa | CH₃ | 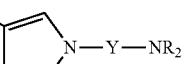 | CH₂CH(OH)CH₂ | 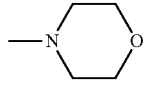 |
| XXVb | CH₃ | 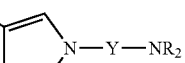 | CH₂CH(OH)CH₂ | 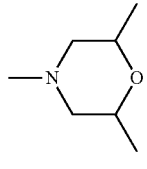 |
| XXVc | CH₃ | 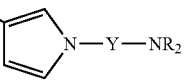 | CH₂CH(OH)CH₂ | 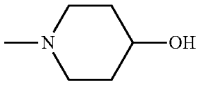 |
| XXVIa | CH₃ | 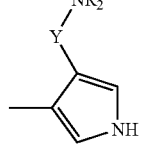 | —C=O | 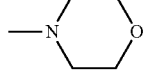 |
| XXVIb | CH₃ | 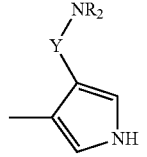 | —C=O | 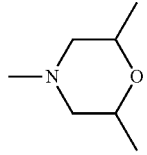 |
| XXVIc | CH₃ | 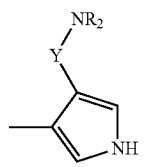 | —C=O | 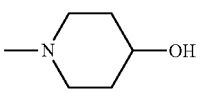 |

EXPERIMENTAL PROCEDURES FOR COMPOUNDS XIII-XXVI

The building blocks 4-(chloroacetyl)morpholine, 4-(chloroacetyl)-2,6-dimethylmorpholine, 4-(3-chloropropanoyl)morpholine and 1-(chloroacetyl)piperidin-4-ol have been already reported in the literature, while we prepared them by a new method not yet described, which was also used for the synthesis of the not yet reported 4-(3-chloropropanoyl)-2,6-dimethyl-morpholine, as described in the following scheme 1:

Scheme 1

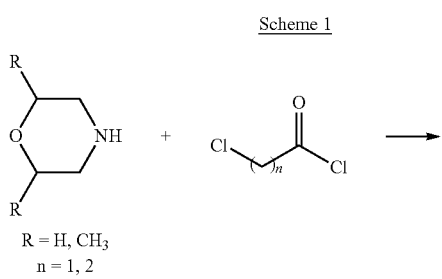

R = H, CH$_3$
n = 1, 2

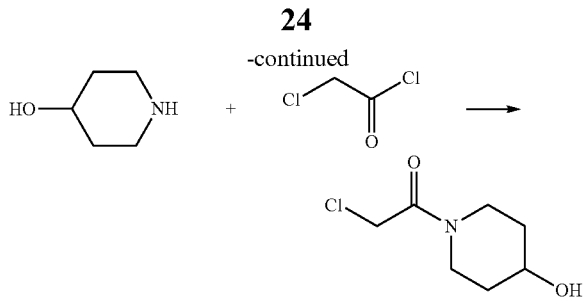

Compounds XIII were prepared by cyclization of 3-(cyclopentyloxy)-N-hydroxy-4-methoxybenzenecarboximidoyl chloride, obtained in turn from 3-(cyclopentyloxy)-4-methoxybenzaldehyde oxime with N-chlorosuccinimide, with ethylacrilate obtaining the intermediate dihydroisoxazole-5-carboxylate ethylester, which was in turn treated with the proper amine, as reported in the following scheme 2.

Compounds XIV were prepared by cyclization of 3-(cyclopentyloxy)-N-hydroxy-4-methoxybenzenecarboximidoyl chloride with 3-butenoic acid obtaining the intermediate dihydroisoxazol-5-acetic acid which was in turn treated with the proper amine in the presence of diphenylfosforylazide (DPPA), as reported in the following scheme 2 (method A):

Scheme 2

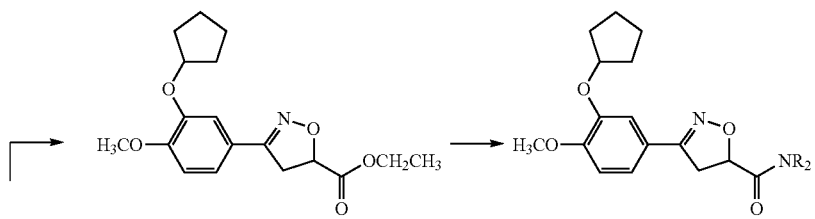

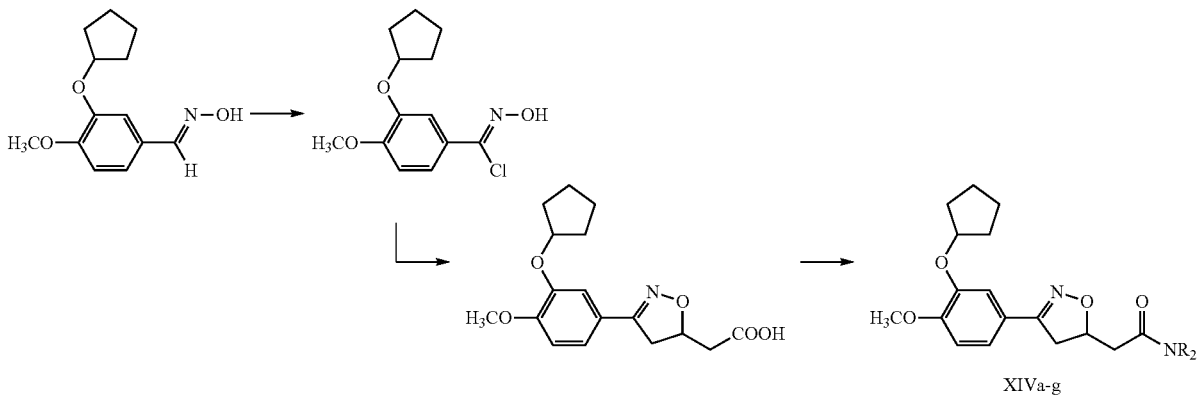

-continued

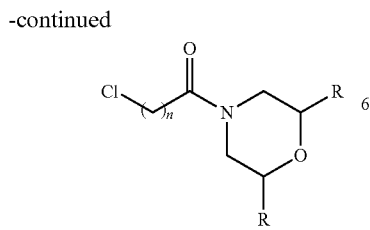

The starting 3-(cyclopentyloxy)-4-methoxybenzaldehyde oxime was obtained by reaction of 3-(cyclopentyloxy)-4-methoxybenzaldehyde with hydroxylamine in ethanol and 3-(cyclopentyloxy)-4-methoxybenzaldehyde was in turn obtained from isovanilline by alkylation with bromocyclopentane following a literature methods [M. J. Ashton, et al., J. Med. Chem. 1994, 37, 1696-1703].

Compounds XIVa-b have been prepared also by an alternative convergent synthetic strategy which involves the cyclization of 3-(cyclopentyloxy)-N-hydroxy-4-methoxybenzenecarboximidoyl chloride with the suitable 4-amine- 3-buten-1-one, which was in turn prepared by a simple, not yet reported, one-pot reaction, starting from 3-butenoic acid; the latter was firstly transformed in the corresponding acyl chloride which was subsequently condensed with the suitable cycloamine, as reported in the following scheme 3 (method B):

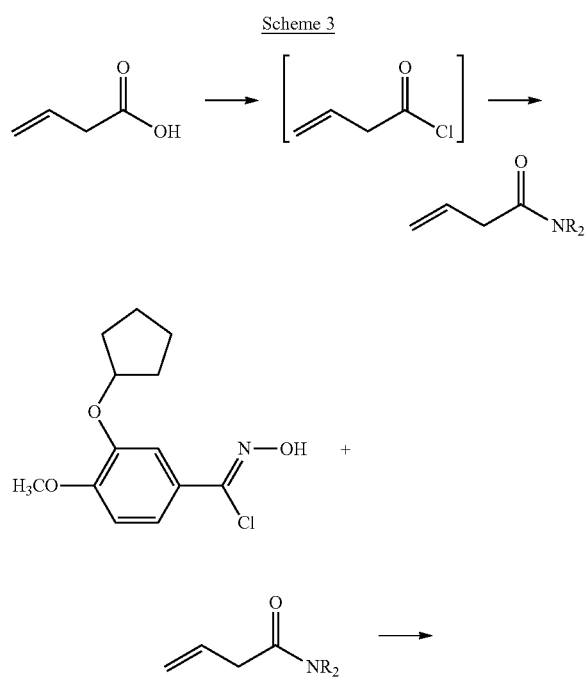

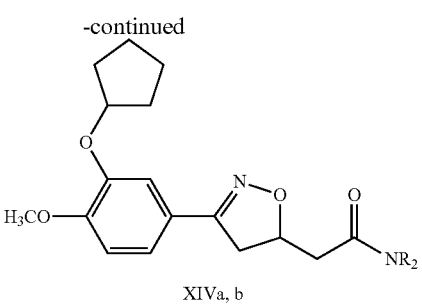

XIVa, b

Compounds XV, XVI and XVII were prepared by the procedure already reported in the literature for similar compounds [Kano H., Adachi 1 et al. *J. Med. Chem.*, 1967, 10, 411-418]. The isoxazole intermediate was obtained by a 1,3-dipolar addition of 3-(cyclopentyloxy)-N-hydroxy-4-methoxybenzenecarboximidoyl chloride with 3-butyn-2-ol. Then, the secondary alcohol group was oxidized to ketone with a mixture of acetic anhydride and dimethyl sulfoxide yielding the 1-{3-[3-(cyclopentyloxy)-4-methoxyphenyl]isoxazol-5-yl}ethanone which was brominated in the alpha position to the carbonyl. The bromo derivative was treated with two equivalents of the suitable cycloamine obtaining the amminoketons XVa,b which are immediately converted into their corresponding hydrochlorides to avoid the decomposition. The arninoalcohols XVIa,b were obtained by reduction of the corresponding aminoketons XVa,b with sodium borohydride and sodium methoxide in anhydrous methanol.

The cyclization of 3-(cyclopentyloxy)-N-hydroxy-4-methoxybenzenecarboximidoyl chloride with methylpropargyl ester gave the intermediate isossazole ester, which was in turn treated with an excess of the suitable cycloamine to give compounds XVII.

All the reaction are reported in the following scheme 4:

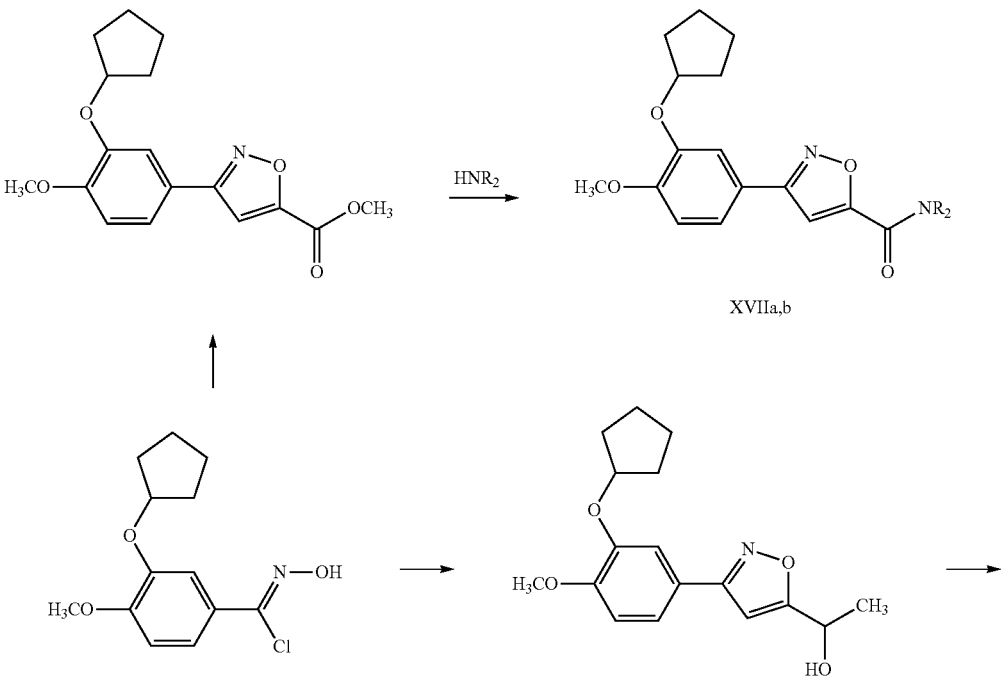

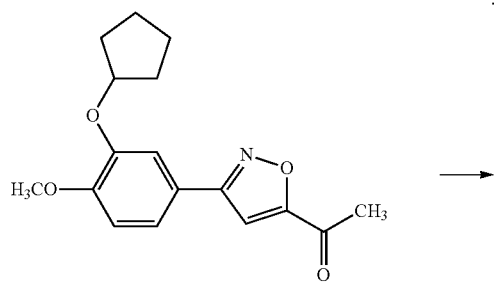

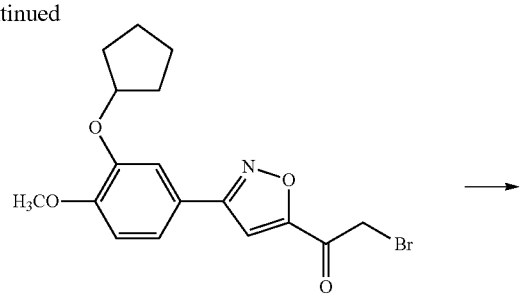

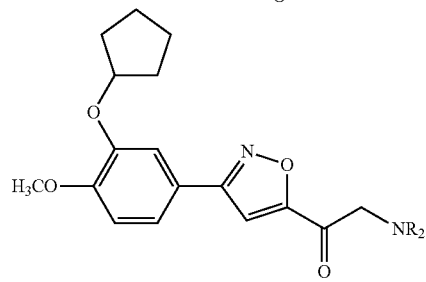

XVa,b

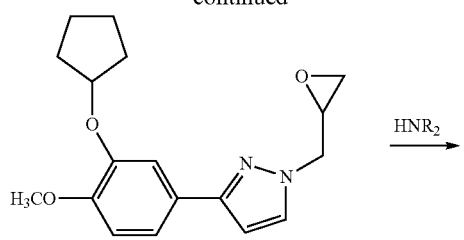

XVIa,b

For the synthesis of compounds XVIIIE-XXI we prepared firstly the starting compound 3-[3-(cyclopentyloxy)-4-methoxyphenyl]-1H-pyrazole by a 1,3-dipolar cycloaddition from the 3-(cyclopentyloxy)-4-methoxybenzaldehyde with p-toluenesulfonyl hydrazide, NaOH and 1-vinylimidazole in acetonitrile, as reported in the scheme 5 This technique was already reported in the literature for the one-pot preparation of pyrazoles [Aggarwal, V. K. et al., *J. Org. Chem.* 2003, 68, 5381-5383].

The pyrazole intermediate was treated with an excess of epichlorohydrin in the presence of TEA to afford the 1,3-disubstituted pyrazole as a single isomer. The structure of the epoxy derivative was identified by $^{13}$C and $^{1}$H NMR spectral data, as reported in detail below. The reaction between the epoxy derivative with an excess of the suitable cycloamine gave compounds XVIIIa-c in good yields. The acetyl derivative XIX was obtained from XVIIIa with acetic anhydride, as reported in the scheme 5:

Scheme 5

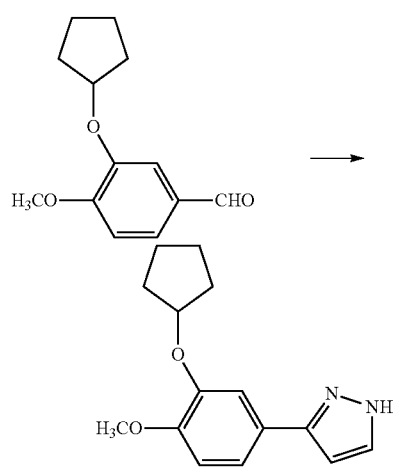

-continued

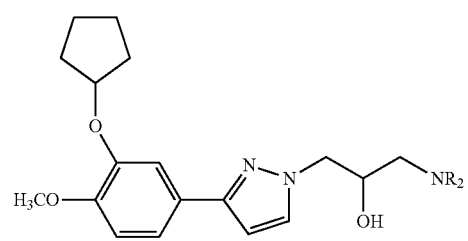

XVIIIa-c

XVIIIa

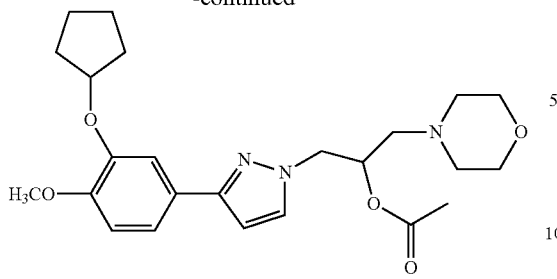

XIX

The treatment of the above pyrazole derivative with 4-(chloroacetyl)morpholine or 4-(chloroacetyl)-2,6-dimethylmorpholine in the presence of TEA afforded to the 4-({3-[3-(cyclopentyloxy)-4-methoxyphenyl]-1H-pyrazol-1-yl}acetyl)amines XXa,b, as reported in the scheme 6.

The same procedure was used to obtain the 4-(3-{3-[3-(cyclopentyloxy)-4-methoxypheny]-1H-pyrazol-1-yl}propanoyl)morpholine XXIa starting from the above pyrazole derivative and 4-(3-chloropropanoyl)morpholine as reported in the scheme 6.

Scheme 7

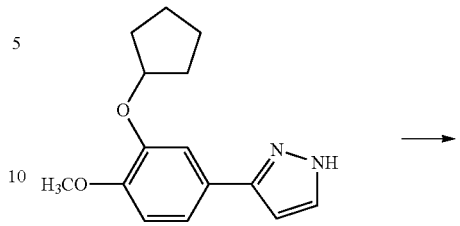

Scheme 6

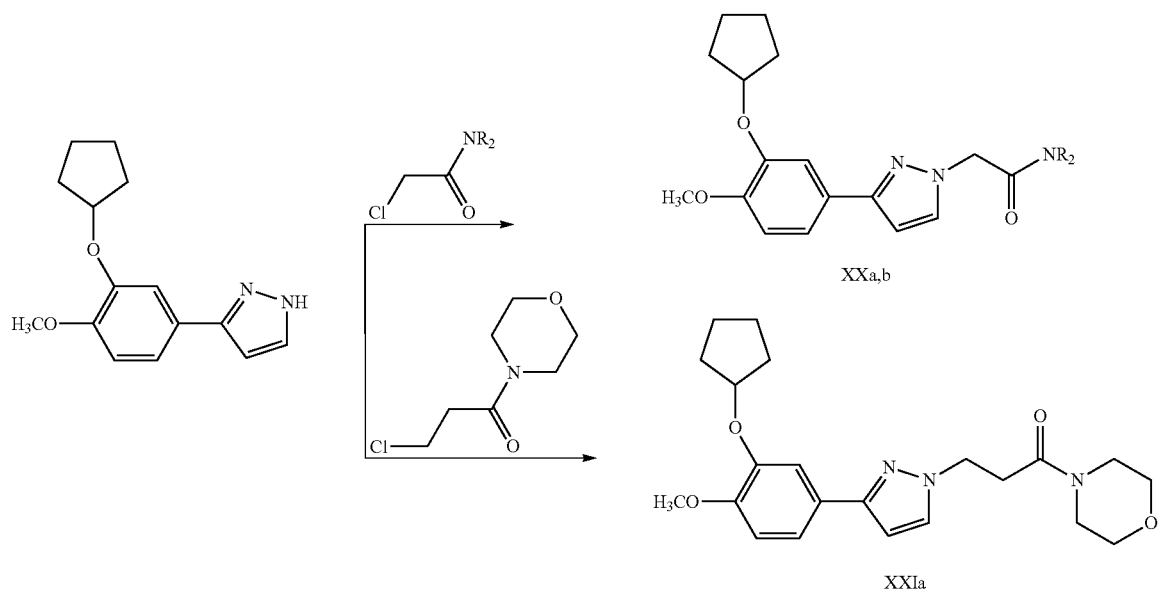

To obtain the 4-(3-{3-[3-(cyclopentyloxy)-4-methoxyphenyl]-1H-pyrazol-1-yl}propanoyl)2,6-dimethylmorpholine XXIb, the pyrazole derivative was treated with an excess of methyl 3-bromopropanoate yielding the methyl 3-{3-[3-(cyclopentyloxy)-4-methoxyphenyl]-1H-pyrazol-1-yl}-propanoate which was then hydrolized to the corresponding acid; the latter was treated with 2,6-dimethylmorpholine, in the presence of TEA and diphenylphosphorylazide, to afford the desired product as reported in the scheme 7.

-continued

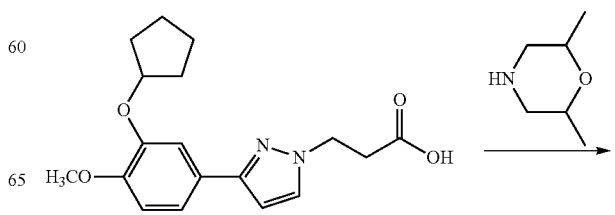

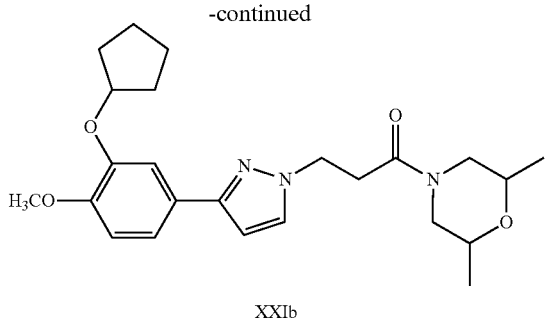

XXIb

To obtain compound XXIIa,c we prepared the starting product 4-(difluoromethoxy)-3-hydroxybenzaldehyde by using a new microwave assisted procedure with improved yield in respect to the numerous procedures reported in the literature. The 3-(cyclopentyloxy)-4-(difluoromethoxy)benzaldehyde was obtained by the literature method [A. Thomas et al. PCT Int. Appl., 2004, WO 2004016596], as well the 3-(cyclopentyloxy)-4-(difluoromethoxy)benzaldehyde oxime [Palle, Venkata P. et al., PCT Int. Appl. (2005), WO 2005051931] as reported in the scheme 8.

Scheme 8

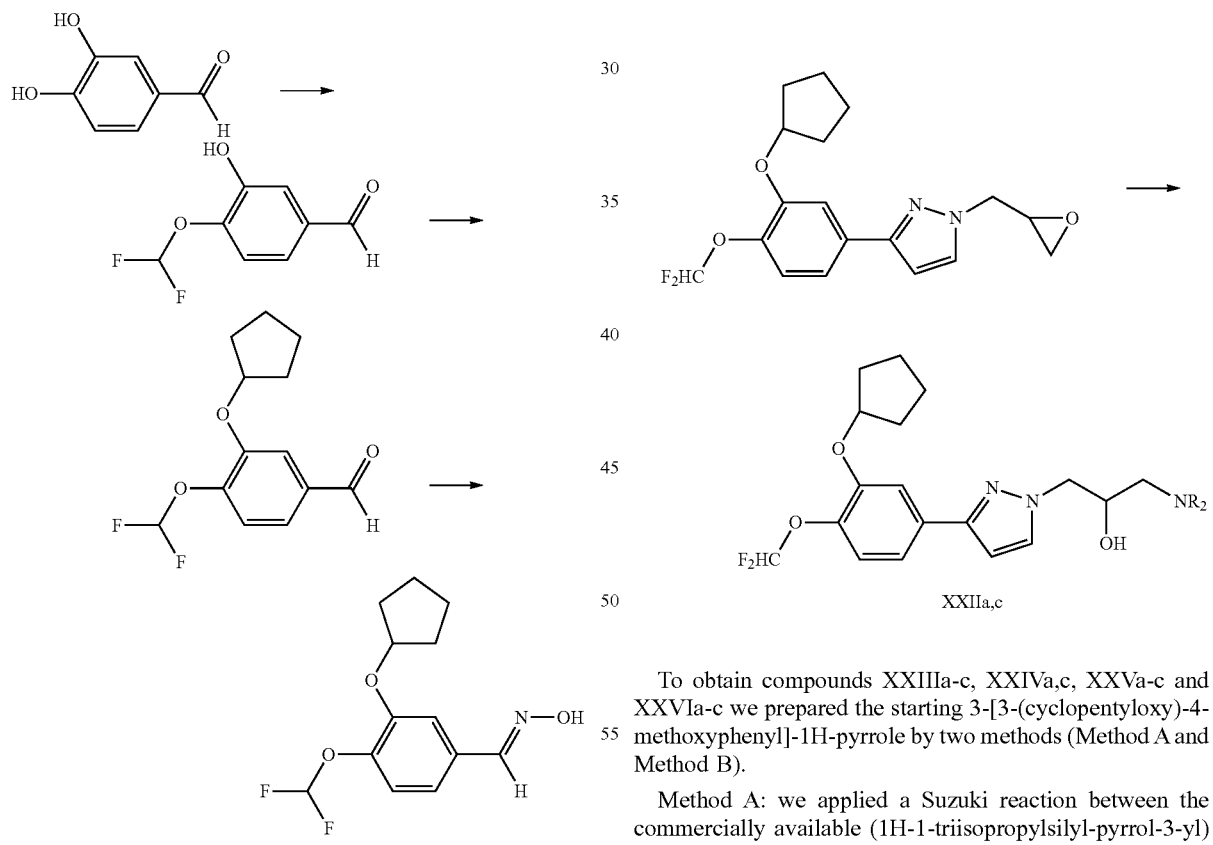

Then, we prepared the 3-[3-(cyclopentyloxy)-4-(difluoromethoxy)phenyl]-1H-pyrazole by a 1,3-dipolar cycloaddition from the 3-(cyclopentyloxy)-4-(difluoromethoxy)benzaldehyde with p-toluenesulfonyl hydrazide, NaOH and 1-vinylimidazole in acetonitrile.

The pyrazole intermediate was treated with an excess of epichlorohydrin in the presence of TEA to afford the 1,3-disubstituted pyrazole as a single isomer. The reaction between the epoxy derivative with an excess of morpholine solved in DMF gave compounds XXIIa, while compound XXIIc was obtained treating the epoxy derivative with 4-hydroxy-piperidine solved in DMF, as reported in the scheme 9.

Scheme 9

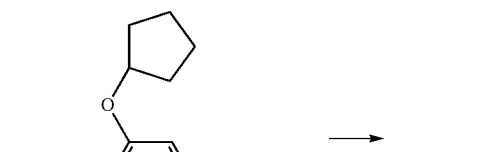

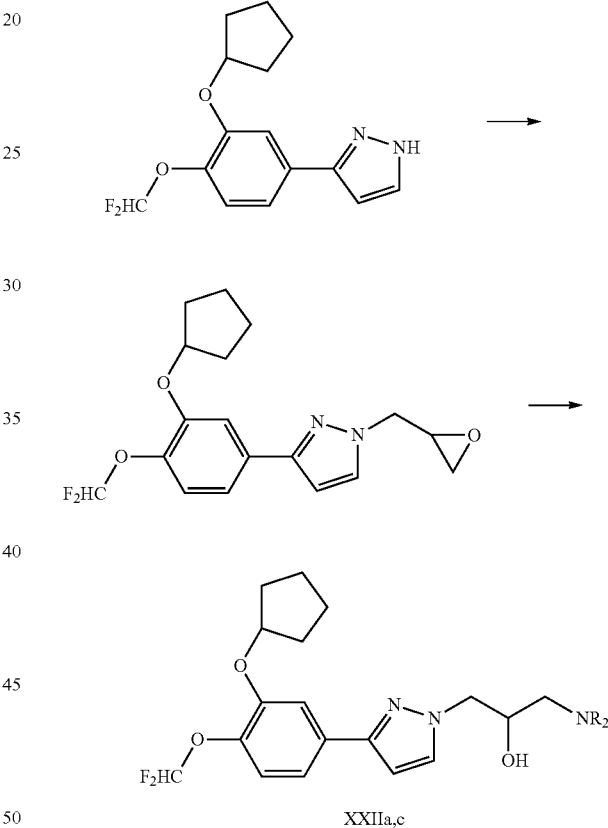

XXIIa,c

To obtain compounds XXIIIa-c, XXIVa,c, XXVa-c and XXVIa-c we prepared the starting 3-[3-(cyclopentyloxy)-4-methoxyphenyl]-1H-pyrrole by two methods (Method A and Method B).

Method A: we applied a Suzuki reaction between the commercially available (1H-1-triisopropylsilyl-pyrrol-3-yl) boronic acid and the 4-bromo-2-(cyclopentyloxy)-1-methoxybenzene prepared following the literature procedure [Diaz A., et al., Synthesis, 1997, 5: 559]. The reaction was done in a basic medium and in the presence of (triphenylphosphine)palladium(0) (TETRAKIS). The triisopropylsilyl group was removed by a 1M tetrabutylammonium fluoride obtaining the desired pyrrole derivative as reported in the scheme 10.

Scheme 10

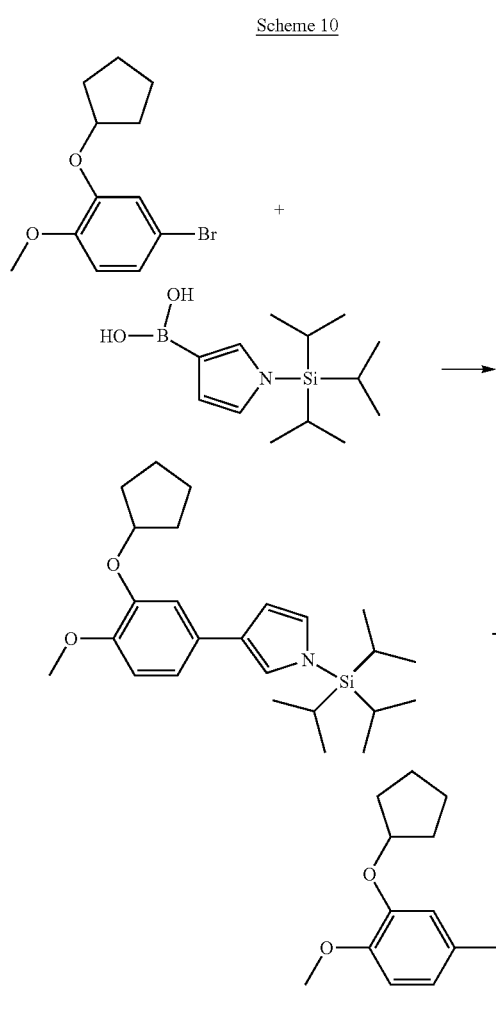

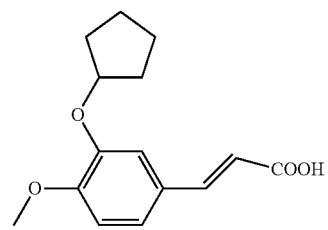

By a classic Fischer esterification we obtained the intermediate ester, which was then cyclized by p-toluenesulfonylmethyl isocianide (TOSMIC reagent), in the presence of sodium hydride, under nitrogen atmosphere, obtaining a 4-carboxyethyl-pyrrole. The 4-carboxyethyl group was hydrolyzed in basic condition giving the acid intermediate which was decarboxylated at high temperature obtaining the desired pyrrole derivative as reported in the scheme 12.

Scheme 12

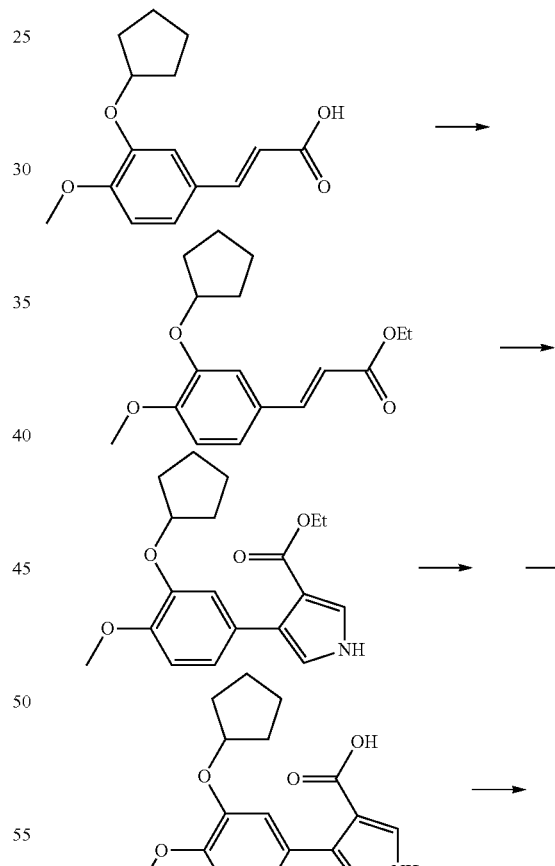

Method B: the starting product is the 3-cyclopentyloxy-4-methoxy trans cinnamic acid which is known in the literature [Itoh K., Kanemasa S. *J. Am. Chem. Soc.*, 2002, 124, 13394-13395; Roger M. Davey, N. Patrick J. Stamford, *Tetrahedron letters*, 2012, 53, 2537-2539] while we have prepared it by a different method, already reported for similar compounds. In detail, the 3-cyclopentyloxy-4-methoxybenzaldehyde was reacted with malonic acid in the presence of dimethylformamide dimethylacetal (DMFDMA) and triethylamine as reported in the scheme 11.

Scheme 11

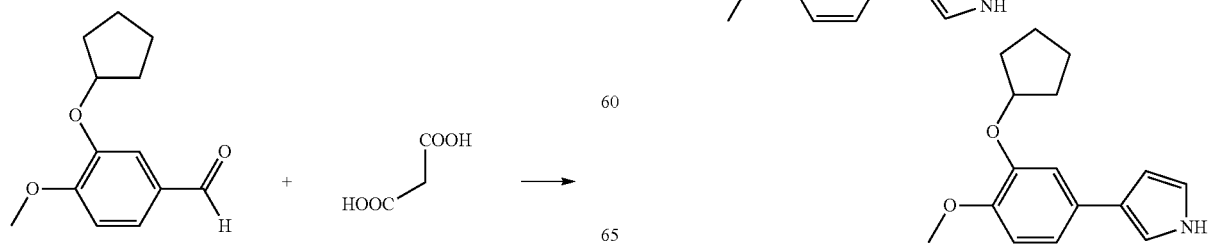

For the synthesis of compounds XXIIIa-c and XXIVa,c we applied a convergent synthetic strategy involving the 3-[3-(cyclopentyloxy)-4-methoxyphenyl]-1H-pyrrole and the suitable chloroacetylamines or chloropropionylamides (in turn prepared as reported in the scheme 1), in the presence of sodium hydride at 0° C., as reported in the scheme 13.

Scheme 13

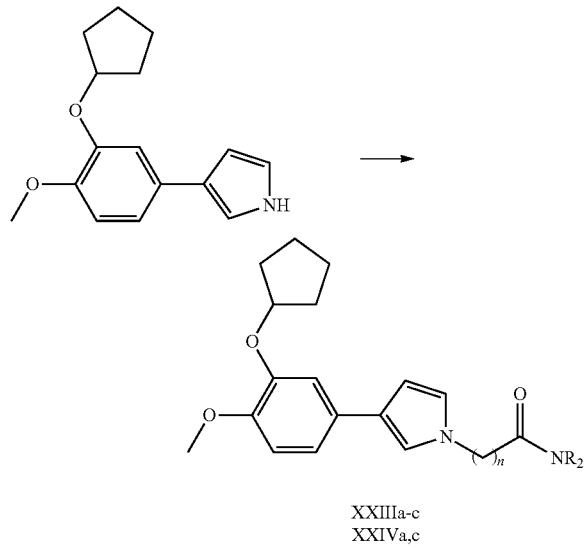

XXIIIa-c
XXIVa,c

For the synthesis of compounds XXVa-c the 3-[3-(cyclopentyloxy)-4-methoxyphenyl]-1H-pyrrole was reacted with epichlorohydrin giving the oxirane intermediate that was then treated with excess of morpholine or dimethyl-morpholine to obtain compounds XXVa,b or with 4-hydroxypiperidine, solved in anhydrous dimethylformamide, to obtain compound XXVc, as reported in Scheme 14.

Scheme 14

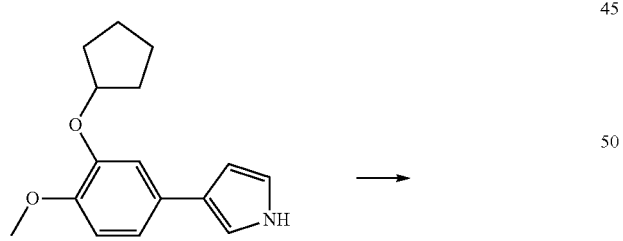

-continued

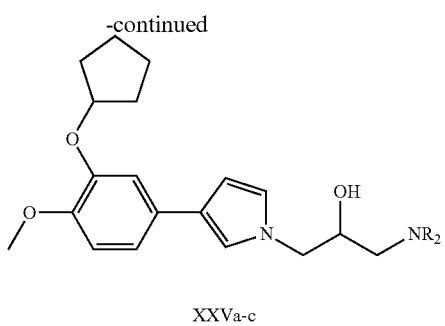

XXVa-c

Compounds XXVIa-c were prepared starting from 4-(3-(cyclopentyloxy)-4-methoxyphenyl)-1H-pyrrole-3-carboxylic acid by reaction with the suitable cycloamine in the presence of triethylamine and DPPA in anhydrous DMF (Scheme 15).

Scheme 15

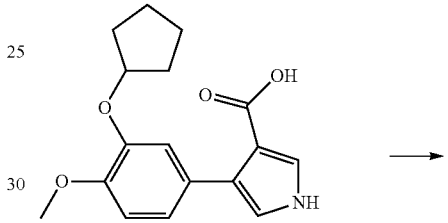

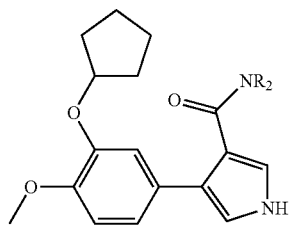

XXVIa-c

DETAILED DESCRIPTIONS

Synthesis of the Intermediate Chloroacetylamines and Cloropropanoylamines

To a solution of the suitable cycloanaine (23 mmol) in an. toluene (60 mL), an. $K_2CO_3$ (6.3 g, 45 mmol) and 2-chloroacetyl chloride or 3-chloropropanoyl chloride (23 mmol) were added; the mixture was heated at 60° C. for 2 h. After cooling to room temperature, the solids ($K_2CO_3$ and KCl) were filtered off and the solution was concentrated under reduced pressure obtaining crude oils which were purified by high vacuum distillation to afford final pure compounds as light yellow oils.

4-(Chloroacetyl)morpholine

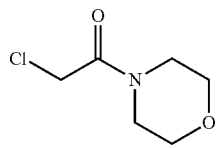

Yield: 72% (lett.: 17-100%). Bp: 110-120° C./0.6 mmHg.

4-(Chloroacetyl)-2,6-dimethylihnorpholine

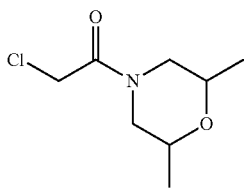

Yield: 82% (lett.: 48%). Bp: 110-120° C./0.6 mmHg.

4-(3-Chloropropanoyl)morpholine

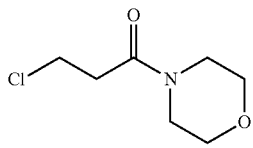 [SMILES: O=C(CCCl)N1CCOCC1]

Yield: 70 (lett.: 85%). Bp: 110° C./0.6 mmHg.

4-(3-Chloropropanoyl)-2,6-dimethylmorpholine

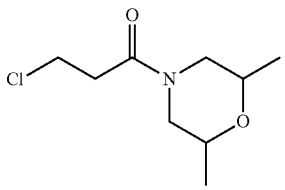

Yield: 80%. Bp: 118° C./0.6 mmHg.

Synthesis of 1-(chloroacetyl)piperidin-4-ol

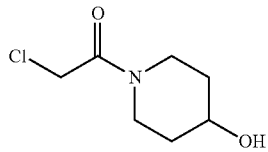 [SMILES: O=C(CCl)N1CCC(O)CC1]

Piperidin-1-01 (1 g, 10 mmol) was solved in a mixture of saturated $Na_2CO_3$ solution (75 mL) and ethyl acetate (150 mL) and chloroacetyl chloride (1.2 mL, 15 mmoli) was added. The reaction mixture was stirred at room temperature for 2 h. After separation in a glass funnel the organic phase was dried ($MgSO_4$) and evaporated under reduced pressure to afford a pure light yellow oil which was used without further purification.

Yield: 1.18 g, 66% (lett. 84%).

Synthesis of 3-(cyclopentyloxy)-N-hydroxy-4-methoxybenzenecarboximidoyl chloride

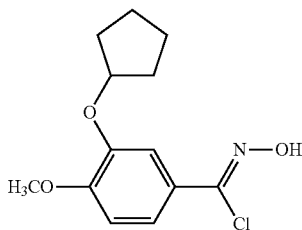 [SMILES: COc1ccc(/C(Cl)=N/O)cc1OC1CCCC1]

To a solution of 3-(cyclopentyloxy)-4-methoxybenzaldehyde oxime (1.72 g, 7.31 mmol) in an. DMF (10 mL), N-chlorosuccinimide (1.02 g, 7.67 mmol) was added and the mixture was stirred at 40-45° C. for 1 h. After cooling to room temperature, water (65 mL) was added and the solution was put for 12 h in a refrigerator; afterward the water was settled and the oil residue was solved in AcOEt (20 mL), the organic phase was washed with water (3×20 mL), dried ($MgSO_4$) and concentrated under reduced pressure yielding a light brown oil.

Yield: 65%. $^1$H-NMR ($CDCl_3$): δ 1.47-2.13 (m, 8H, $4CH_2$ cyclopent.), 3.87 (s, 3H, $OCH_3$), 4.71-4.89 (m, 1H, OCH cyclopent.), 6.84 (d, J=8.4 Hz, 1H, H-5 Ar), 7.35 (dd, J=8.4, 2.0 Hz, 1H, H-6 Ar), 7.38 (d, J=2.0 Hz, 1H, H-2 Ar). IR (film): $cm^{-1}$ 3000-3500 (OH). Anal. ($C_{13}H_{16}ClNO_3$) C, H, N. (% calculated/found) C: 57.89/57.67; H: 5.98/5.92; N: 5.19/5.29.

Synthesis of ethyl 3-[3-(cyclopentyloxy)-4-methoxyphenyl]-4,5-dihydroisoxazole-5-carboxylate

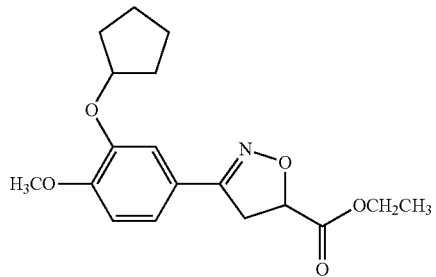 [SMILES: CCOC(=O)C1CC(c2ccc(OC)c(OC3CCCC3)c2)=NO1]

For the synthesis of ethyl 3-[3-(cyclopentyloxy)-4-methoxyphenyl]-4,5-dihydroisoxazole-5-carboxylate we applied the procedure already described in the literature (*Bioorg. Med. Chem.* 19, 2011, 7365-7373).

To a solution of 3-(cyclopentyloxy)-N-hydroxy-4-methoxybenzenecarboximidoyl chloride (2.85 g, 10.57 mmol) in dichloroethane (DCE) (16 mL) cooled at 0° C., under nitrogen atmosphere, ethyl acrylate (2.31 mL, 21.14 mmol) and triethylamine (TEA) (3.54 mL, 25.37 mmol) were added.

The yellow solution was stirred at 60° C. for 1 h and at r.t. for further 48 h. Water (20 mL) was added and the mixture was extracted with DCM (3×10 mL). The organic phases were washed with brine (3×10 mL), dried ($MgSO_4$) and concentrated under reduced pressure yielding an oil which was purified by silica gel (100-200 mesh) column chromatography using a mixture of diethyl ether/petroleum ether (boiling point 40-60° C.) (1:1) as the eluent. The final product crystallised as a light yellow solid which was recrystallized by diethyl ether.

Yield: 50% M.p.: 60° C. $^1$H-NMR ($CDCl_3$): δ 1.36 (t, 3H, $OCH_2\underline{CH_3}$), 1.50-2.10 (m, 8H, 4 $CH_2$ cyclopent.), 3.60-3.65 (m, 2H, $CH_2$ isoxaz.), 3.89 (s, 3H, $OCH_3$), 4.28 (q, 2H, O$\underline{CH_2}CH_3$), 4.78-4.90 (m, 1H, OCH cyclopent.), 5.16 (t, J=8.6 Hz 1H, H-5 isoxaz.), 6.86 (d, J=8.0 Hz, 1H, H-5 Ar), 7.05 (dd, J=8.2, 2.0 Hz, 1H, H-6 Ar), 7.37 (d, J=2.0 Hz, 1H, H-2 Ar). Anal. ($C_{18}H_{23}NO_5$) C, H, N. (% calculated/found) C: 64.85/64.76; H: 6.95/7.24; N: 4.20/4.14.

General procedure for 4-({3-[3-(cyclopentyloxy)-4-methoxyphenyl]-4,5-dihydroisoxazol-5-yl}carbonyl) amines XIII a-f A mixture of ethyl 3-[3-(cyclopentyloxy)-4-methoxyphenyl]-4,5-dihydroisoxazole-5-carboxylate and the suitable amine was heated at 60° C. overnight. If the amine was a solid the reaction was carried on in anhydrous DMF. After cooling to room temperature, the reaction mixture was poured into water (20 mL) yielding a crude solid which was filtered and recrystallized from diethyl ether. If no precipitate was formed, the water suspension was extracted with DCM (3×10 mL), washed with 1N HCl solution (10 mL) and brine (2×10 mL), dried ($MgSO_4$) and evaporated under reduced pressure. The solid obtained was recrystallized from diethyl ether.

4-({3-[3-(Cyclopentyloxy)-4-methoxyphenyl]-4,5-dihydroisoxazol-5-yl}carbonyl)morpholine XIIIa

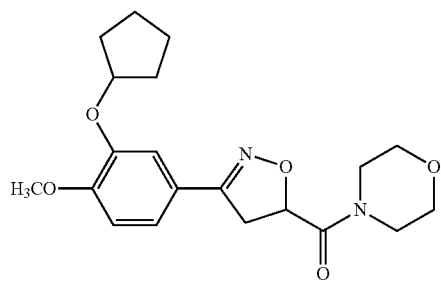 [SMILES: COc1ccc(C2=NOC(C(=O)N3CCOCC3)C2)cc1OC1CCCC1]

White solid. Yield: 76%. M.p.: 115-116° C. $^1$H-NMR ($CDCl_3$): δ 1.55-2.10 (m, 8H, $4CH_2$ cyclopent.), 3.30-4.30 (m, 13 H, $CH_2$ isoxazol.+$4CH_2$ morph.+$OCH_3$), 4.78-4.90 (m, 1H, OCH cyclopent.), 5.30-5.40 (m, 1H, H-5 isoxaz.), 6.88 (d, J=8.0 Hz, 1H, H-5 Ar), 7.13 (dd, J=6.6, 2.0 Hz, 1H, H-6 Ar), 7.37 (d, J=2.0 Hz, 1H, H-2 Ar). Anal. ($C_{20}H_{26}N_2O_5$) C, H, N. (% calculated/found) C: 64.16/64.27; H: 7.00/7.32; N: 7.48/7.31.

4-({3-[3-(Cyclopentyloxy)-4-methoxyphenyl]-4,5-dihydroisoxazol-5-yl}carbonyl)-2,6-dimethylmorpholine XIIIb

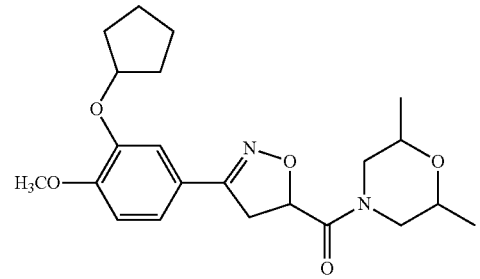 [SMILES: COc1ccc(C2=NOC(C(=O)N3CC(C)OC(C)C3)C2)cc1OC1CCCC1]

Pale yellow solid. Yield: 65%. M.p.: 127-129° C. $^1$H-NMR ($CDCl_3$): δ1.10-1.20 (m, 6H, $CH_3$), 1.60-2.10 (m, 8H, $4CH_2$ cyclopent.), 3.30-4.50 (m, 10H, $CH_2$ isoxaz.+$CH_2N$ morph.+CH morph.+$OCH_3$), 4.88-4.98 (m, 1H, OCH cyclopent.), 5.30-5.50 (m, 1H, H-5 isoxaz.), 6.90 (d, J=8.0 Hz, 1H, H-5 Ar), 7.15 (dd, J=6.6, 2.0 Hz, 1H, H-6 Ar), 7.20 (d, J=2.0 Hz, 1H, H-2 Ar). Anal. ($C_{22}H_{30}N_2O_5$) C, H, N. (% calculated/found) C: 65.65/65.44; H: 7.51/7.70; N: 6.96/6.90.

1-({3-[3-(Cyclopentyloxy)-4-methoxyphenyl]4,5-dihydroisoxazol-5-yl}carbonyl)piperidin-4-ol XIIIc

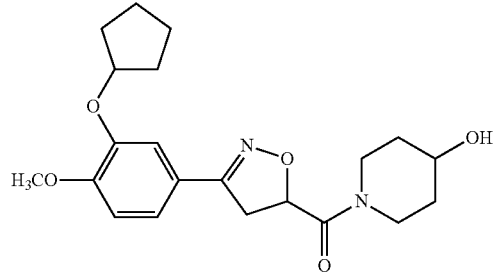 [SMILES: COc1ccc(C2=NOC(C(=O)N3CCC(O)CC3)C2)cc1OC1CCCC1]

White solid. Yield: 38%. M.p.: 134° C. $^1$H-NMR ($CDCl_3$): δ 1.45-2.20 (m, 12H, $4CH_2$ cyclopent.+$2CH_2$ pip.), 3.10-4.40 (m, 11H, $OCH_3$+$2CH_2N$ pip.+$CH_2$ isoxaz.+$\underline{CH}$-OH+OH, 1H disappears with $D_2O$), 4.80-4.90 (m, 1H, OCH cyclopent.), 5.30-5.50 (m, 1H, H-5 isoxaz.), 6.88 (d, J=8.3 Hz, 1H, H-5 Ar), 7.18 (dd, J=6, 1.6 Hz, 1H, H-6 Ar), 7.37 (d, J=2.0 Hz, 1H, H-2 Ar). Anal. ($C_{21}H_{28}N_2O_5$) C, H, N. (% calculated/found) C: 64.93/64.67; H: 7.27/7.48; N: 7.21/7.11.

3-[3-(Cyclopentyloxy)-4-methoxyphenyl]-5-(pyrrolidin-1-ylcarbonyl)-4,5-dihydroisoxazole XIIId

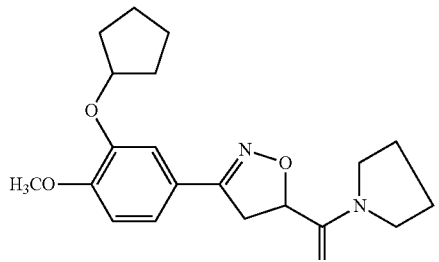

White solid. Yield: 84%. M.p.: 126-127° C. $^1$H-NMR (CDCl$_3$): δ 1.50-2.20 (m, 12H, 4CH$_2$ cyclopent.+2CH$_2$ pyrr.), 3.35-4.28 (m, 9H, CH$_2$ isoxaz.+2CH$_2$N pyrr+OCH$_3$), 4.80-4.95 (m, 1H, OCH cyclopent.), 5.20-5.40 (m, 1H, H-5 isoxaz.), 6.87 (d, J=8.0 Hz, 1H, H-5 Ar), 7.15 (dd, J=6.3, 1.6 Hz, 1H, H-6 Ar), 7.37 (d, J=2.0 Hz, 1H, H-2 Ar). Anal. (C$_{20}$H$_{26}$N$_2$O$_4$) C, H, N. (% calculated/found) C: 67.02/67.24; H: 7.31/7.52; N: 7.82/7.80.

1-({3-[3-(Cyclopentyloxy)-4-methoxyphenyl]-4,5-dihydroisoxazol-5-yl}carbonyl)piperidine XIIIe

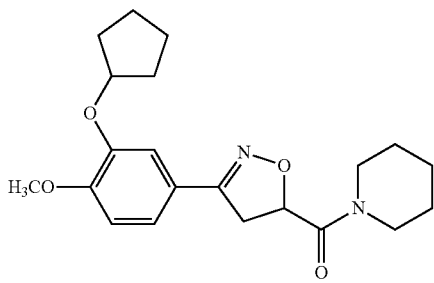 [SMILES: COc1ccc(C2=NOC(C(=O)N3CCCCC3)C2)cc1OC1CCCC1]

White solid. Yield: 22%. M.p.: 130° C. $^1$H-NMR (CDCl$_3$): δ 1.50-2.10 (m, 14H, 4CH$_2$ cyclopent.+3CH$_2$ pip.), 3.30-4.37 (m, 9H, CH$_2$ isoxaz.+2CH$_2$N pip.+OCH$_3$), 4.80-4.90 (m, 1H, OCH cyclopent.), 5.30-5.42 (m, 1H, H-5 isoxaz.), 6.90 (d, J=8.0 Hz, 1H, H-5 Ar), 7.17 (dd, J=6.6, 1.6 Hz, 1H, H-6 Ar), 7.38 (d, J=2, 1H, H-2 Ar). Anal. (C$_{21}$H$_{28}$N$_2$O$_4$) C, H, N. (% calculated/found) C: 67.72/67.57; H: 7.58/7.63; N: 7.52/7.41.

3-[3-(Cyclopentyloxy)-4-methoxyphenyl]-N,N-bis(2-hydroxyethyl)-4,5-dihydroisoxazole-5-carboxamide XIIIf

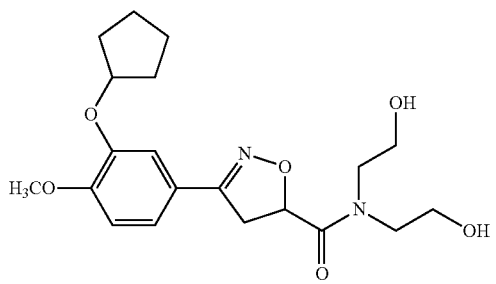 [SMILES: COc1ccc(C2=NOC(C(=O)N(CCO)CCO)C2)cc1OC1CCCC1]

White solid. Yield: 70%. M.p.: 85° C. $^1$H-NMR (CDCl$_3$): δ 1.55-2.10 (m, 8H, 4CH$_2$ cyclopent.), 3.30-4.20 (m, 15 H, CH$_2$ isoxaz.+2CH$_2$N+2CH$_2$OH+OCH$_3$+2OH, 2H disappear with D$_2$O), 4.77-4.84 (m, 1H, OCH cyclopent.), 5.30-5.50 (m, 1H, H-5 isoxaz.), 6.88 (d, J=8.3 Hz, 1H, H-5 Ar), 7.17 (dd, J=6.6, 2.0 Hz, 1H, H-6 Ar), 7.36 (d, J=2.0 Hz, 1H, H-2 Ar). Anal. (C$_{20}$H$_{28}$H$_2$O$_6$) C, H, N. (% calculated/found) C: 61.21/61.13; H: 7.19/6.93; N: 7.14/7.08.

Synthesis of {3-[3-(cyclopentyloxy)-4-methoxyphenyl]-4,5-dihydroisoxazol-5-yl}acetic acid

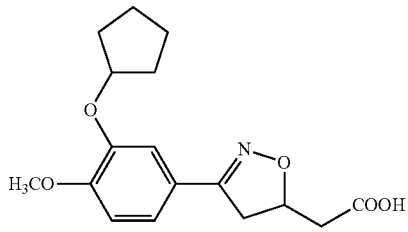 [SMILES: COc1ccc(C2=NOC(CC(=O)O)C2)cc1OC1CCCC1]

To a solution of 3-(cyclopentyloxy)-N-hydroxy-4-methoxybenzenecarboximidoyl chloride (7.9 g, 29.29 mmol) in DCE (46 mL) cooled at 0° C., under nitrogen atmosphere, 3-butenoic acid (5 mL, 58.58 mmol) and TEA (9.8 mL, 70 mmol) were added and the solution was stirred at 60° C. for 1.5 h and at r.t. for further 48 h. Water was added (20 mL) and the mixture was extracted with DCM (3×10 mL). The organic phases were washed with a NaHCO$_3$ saturated solution, then the aqueous phase was treated with 1N HCl solution until the precipitation of the final product as a white solid.

Yield: 35%. Mp: 126-128° C. $^1$H-NMR (CDCl$_3$): δ 1.50-2.10 (m, 8H, 4CH$_2$ cyclopent.), 2.65-3.05 (m, 2H, CH$_2$COOH), 3.05-3.65 (m, 2H, CH$_2$ isoxaz.), 3.90 (s, 3H, OCH$_3$), 4.78-4.95 (m, 1H, OCH cyclopent.), 5.05-5.20 (m, 1H, H-5 isoxaz.), 6.86 (d, J=8.0 Hz, 1H, H-5 Ar), 7.06 (dd, J=8.2, 2.0 Hz, 1H-6, Ar), 7.38 (d, J=2.0 Hz, 1H, H-2 Ar), 8.05 (br s, 1H, COOH, disappears with D$_2$O) Anal. (C$_{17}$H$_{21}$NO$_5$) C, H, N. (% calculated/found) C: 63.94/63.86; H: 6.63/6.67; N: 4.39/4.20.

General procedure for 4-({3-[3-(cyclopentyloxy)-4-methoxyphenyl]-4,5-dihydroisoxazol-5-yl}acetyl) amine XIVa-g (method A)

To a solution of {3-[3-(cyclopentyloxy)-4-methoxyphenyl]-4,5-dihydro isoxazol-5-yl}acetic acid (0.48 g, 1.5 mmol) in anhydrous DMF (4 mL)(mancano i mL), cooled in an ice-water bath, triethylamine (0.31 mL, 2.25 mmol), the suitable amine (3 mmol) and diphenylphosphorilazide (0.36 mL, 1.65 mmol) were added and the reaction mixture was heated at 80° C. for 24 hr. After cooling to room temperature, the reaction mixture was poured into water (50 mL), extracted with DCM (3×10 mL), washed with a NaHCO$_3$ saturated solution (10 mL), 1N HCl solution (10 mL) and brine (2×10 mL), dried (MgSO$_4$) and evaporated under reduced pressure. The solid obtained was purified by crystallization from diethyl ether.

4-({3-[3-(Cyclopentyloxy)-4-methoxyphenyl]-4,5-dihydroisoxazol-5-yl}acetyl)morpholine XIV a

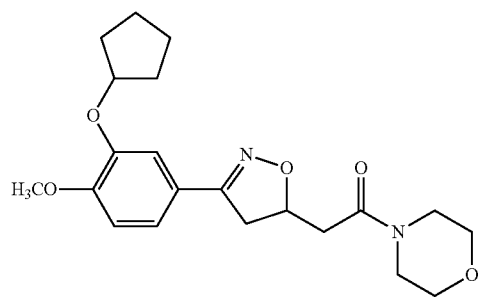 [SMILES: COc1ccc(C2=NOC(CC(=O)N3CCOCC3)C2)cc1OC1CCCC1]

White solid. Yield: 70%. Mp: 144-145° C. $^1$H-NMR (CDCl$_3$): δ 1.53-2.10 (m, 8H, 4CH$_2$ cyclopent.), 2.55-3.05 (m, 2H, CH$_2$CO), 3.08-3.21 and 3.42-3.80 (2m, 10H, CH$_2$ isoxaz.+4CH$_2$ morph.), 3.90 (s, 3H, OCH$_3$), 4.78-4.90 (m, 1H, OCH cyclopent.), 5.02-5.26 (m, 1H, H-5 isoxaz.), 6.87 (d, J=8.0 Hz, 1H, H-5 Ar), 7.08 (dd, J=8.2, 2.0 Hz, 1H, H-6 Ar), 7.37 (d, J=2.0 Hz, 1H, H-2 Ar). Anal. (C$_{21}$H$_{28}$N$_2$O$_5$) C, H, N. (% calculated/found) C: : 64.93/65.19; H: 7.27/7.44; N: 7.21/7.13.

4-({3-[3-(Cyclopentiloxy)-4-methoxyphenyl]-4,5-dihydroisoxazol-5-yl}acetil) 2,6-dimethylmorpholine XIVb

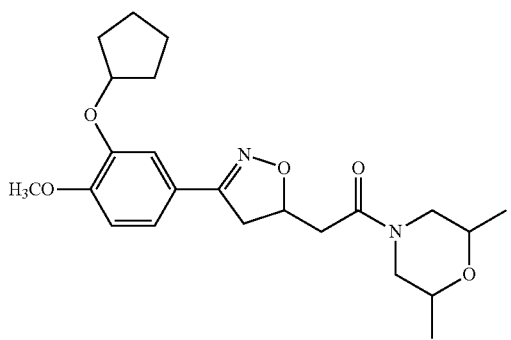 [SMILES: COc1ccc(C2=NOC(CC(=O)N3CC(C)OC(C)C3)C2)cc1OC1CCCC1]

White solid. Yield: 38%. Mp: 104-105° C. $^1$H-NMR (CDCl$_3$): δ 1.00-1.43 (m, 6H, 2CH$_3$ morph.), 1.48-2.13 (m, 8H, 4CH$_2$ cyclopent.), 2.20-4.20 (m, 10H, 2CHO morph.+ 2CH$_2$N morph.+CH$_2$ isoxaz.+CH$_2$CO), 3.90 (s, 3H, OCH$_3$), 4.65-4.96 (m, 1H, OCH cyclopent.), 5.05-5.28 (m, 1H, H-5 isoxaz.), 6.87 (d, J=8.0 Hz, 1H, H-5 Ar), 7.08 (dd, J=8.0, 2.0 Hz, 1H, H-6 Ar), 7.37 (d, J=1.6 Hz, 1H, H-2 Ar). Anal. (C$_{23}$H$_{32}$N$_2$O$_5$) C, H, N. (% calculated/found) C: 66.32/66.43; H: 7.74/7.94; N: 6.73/6.42.

1-({3-[3-(Cyclopentyloxy)-4-methoxyphenyl]-4,5-dihydroisoxazol-5-yl}acetyl)piperidin-4-ol XIVc

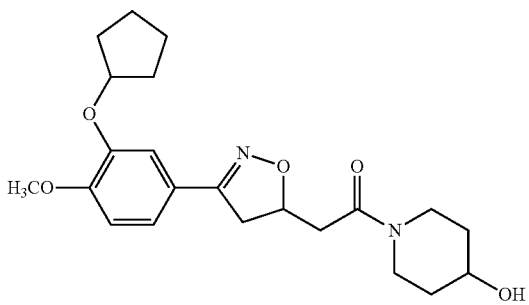 [SMILES: COc1ccc(C2=NOC(CC(=O)N3CCC(O)CC3)C2)cc1OC1CCCC1]

White solid. Yield: 21%. Mp: 134° C. $^1$H-NMR (CDCl$_3$): δ 1.40-2.20 (m, 12H, 4CH$_2$ cyclopent.+2CH$_2$ pip.), 2.55-4.20 (m, 12H, OCH$_3$+CH$_2$ isoxaz.+2CH$_2$N pip.+CH$_2$CO+ CH—OH+OH, 1H disappears with D$_2$O), 4.80-4.90 (m, 1H, OCH cyclopent.), 5.05-5.25 (m, 1H, H-5 isoxaz.), 6.87 (d, J=8.3 Hz, 1H, H-5 Ar), 7.14 (dd, J=7.0, 1.6 Hz, 1H, H-6 Ar), 7.33 (d, J=2.0 Hz, 1H, H-2 Ar). Anal. (C$_{22}$H$_{30}$N$_2$O$_5$) C, H, N. (% calculated/found) C: 65.65/65.83; H: 7.51/7.74; N: 6.96/6.94.

3-[3-(Cyclopentyloxy)-4-methoxyphenyl]-5-(2-oxo-2-pyrrolidin-1-ylethyl)-4,5-dihydroisoxazole XIVd

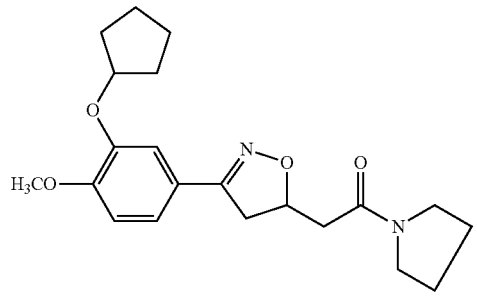 [SMILES: COc1ccc(C2=NOC(CC(=O)N3CCCC3)C2)cc1OC1CCCC1]

White solid. Yield: 36%. Mp: 148-149° C. $^1$H-NMR (CDCl$_3$): δ 1.58-2.10 (m, 12H, 4CH$_2$ cyclopent.+2CH$_2$ pyrr.), 2.60-3.30 (m, 4H, CH$_2$CO+CH$_2$isoxaz.), 3.40-3.60 (m, 4H, CH$_2$N pyrr.), 3.91 (s, 3H, OCH$_3$), 4.80-4.90 (m, 1H, OCH cyclopent.), 5.05-5.20 (m, 1H, H-5 isoxaz.), 6.93 (d, J=8.0 Hz, 1H, H-5 Ar), 7.10 (dd, J=8.0, 2.0 Hz, 1H, H-6 Ar), 7.38 (d, J=2.0 Hz, 1H, H-2 Ar). Anal. (C$_{23}$H$_{28}$H$_2$O$_4$) C, H, N. (% calculated/found) C: 67.72/67.57; H: 7.58/7.80; N: 7.52/7.31.

1-({3-[3-(Cyclopentyloxy)-4-methoxyphenyl]-4,5-dihydroisoxazol-5-yl}acetyl)piperidine XIVe

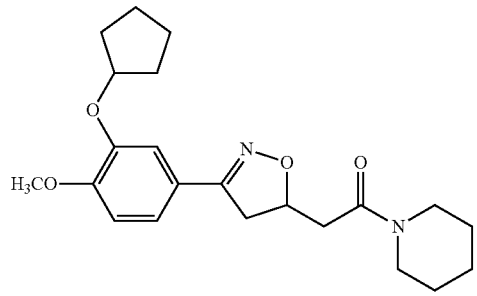 [SMILES: COc1ccc(C2=NOC(CC(=O)N3CCCCC3)C2)cc1OC1CCCC1]

Light brown solid. Yield: 64%. Mp: 104-106° C. $^1$H-NMR (CDCl$_3$): δ 1.50-2.10 (m, 14H, 4CH$_2$ cyclopent.+ 3CH$_2$ pip.), 2.57-3.20 (m, 4H, CH$_2$ isoxaz.+CH$_2$CO), 3.38-3.78 (m, 4H, 2CH$_2$N pip.), 3.90 (s, 3H, OCH$_3$), 4.80-4.90 (m, 1H, OCH cyclopent.), 5.07-5.25 (m, 1H, H-5 isoxaz.), 6.86 (d, J=8.3, 1H, H-5 Ar), 7.09 (dd, J=8.0, 1.6 Hz, 1H, H-6 Ar), 7.37 (d, J=1.6, 1H, H-2 Ar). Anal. (C$_{22}$H$_{30}$N$_2$O$_4$) C, H, N. (% calculated/found) C: 68.37/68.33; H: 7.82/7.53; N: 7.25/7.19.

1-({3-[3-(Cyclopentyloxy)-4-methoxyphenyl]-4,5-dihydroisoxazol-5-yl}acetyl)piperazine XIVf

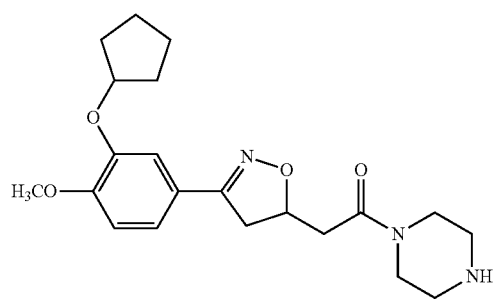 [SMILES: COc1ccc(C2=NOC(CC(=O)N3CCNCC3)C2)cc1OC1CCCC1]

Light brown solid. Yield: 43%. Mp: 108-111° C. $^1$H-NMR (CDCl$_3$): δ 1.50-2.10 (m, 8H, 4CH$_2$ cyclopent.), 2.78-3.30 (m, 4H, CH$_2$CO+CH$_2$isoxaz), 3.30-3.80 (m, 9H, 4CH$_2$ piperaz.+NH, 1H disappears with D$_2$O), 3.86 (s, 3H, OCH$_3$), 4.70-4.90 (m, 1H, OCH cyclopent.), 5.05-5.20 (m, 1H, H-5 isoxaz.), 6.85 (d, J=8.0 Hz, 1H, H-5 Ar), 7.08 (dd, J=8.0, 2.0 Hz, 1H, H-6 Ar), 7.34 (d, J=1.6 Hz, 1H, H-2 Ar). Anal. (C$_{21}$H$_{29}$N$_3$O$_4$) C, H, N. (% calculated/found) C: 65.10/65.06; H: 7.54/7.58; N: 10.84/10.66.

2-{3-[3-(Cyclopentyloxy)-4-methoxyphenyl]-4,5-dihydroisoxazol-5-yl}-N,N-bis(2-hydroxyethyl)acetamide XIVg

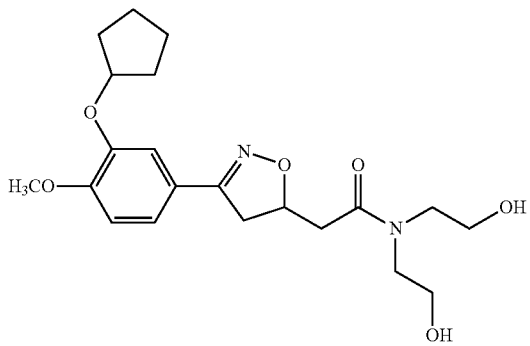 [SMILES: COc1ccc(C2=NOC(CC(=O)N(CCO)CCO)C2)cc1OC1CCCC1]

White solid. Yield: 41%. Mp: 136-138° C. $^1$H-NMR (CDCl$_3$): δ 1.55-2.10 (m, 8H, 4CH$_2$ cyclopent.), 2.10-2.70 (br s, 2H, 2OH, disappear with D$_2$O), 2.75-3.30 (m, 4H, CH$_2$CO+CH$_2$isoxaz.), 3.50-3.75 (m, 4H, 2CH$_2$N), 3.75-3.89 (m, 4H, 2CH$_2$O), 3.90 (s, 3H, OCH$_3$), 4.75-4.90 (m, 1H, OCH cyclopent.), 5.05-5.20 (m, 1H, H-5 isoxaz.), 6.85 (d, J=8.3 Hz, 1H, H-5 Ar), 7.07 (dd, J=8.0, 2.0 Hz, 1H, H-6 Ar), 7.34 (d, J=2.0 Hz, 1H, H-2 Ar). Anal. (C$_{21}$H$_{30}$N$_2$O$_6$) C, H, N. (% calculated/found) C: 62.05/62.29; H: 7.44/7.53; N: 6.89/6.92.

General procedure for 1-(4-morpholinyl)-3-buten-1-one and 1-(2,6-dimethyl-4-morpholinyl)-3-buten-1-one To the 3-butenoic acid (5 g, 58.08 mmol, 4.9 mL) cooled at 0° C., SOCl$_2$ (9.68 g, 81.31 mmol, 5.9 mL) was added dropwise. The mixture was refluxed for 30 minutes, then cooled at 0° C. The suitable cycloamine (114 mmol) solved in an. THF (25 mL) was added and the mixture was stirred at room temperature for 2 h. The solid was filtered off, washed with an. THF and the collected organic phases were evaporated under reduced pressure. To the residue NaHCO$_3$ saturated solution (100 mL) was added and the mixture was extracted with DCM (3×20 mL), the organic phase was washed with water (20 mL), dried (MgSO$_4$) and concentrated under reduced pressure. The crude was purified by high vacuum distillation (95° C./1 mmHg) to afford the pure products as a light yellow oil.

1-(4-Morpholinyl)-3-buten-1-one

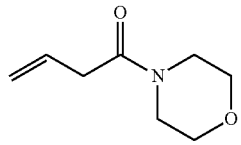

Yield: 67%. $^1$H-NMR (CDCl$_3$): δ 3.00-3.13 (m, 2H, CH$_2$CO), 3.30-3.65 (m, 8H, 4CH$_2$ morph.), 4.95-5.15 (m, 2H, CH$_2$=CH), 5.75-5.93 (m, 1H, CH$_2$=CH). IR (CHCl$_3$) cm$^{-1}$: 1633 (C=O). GC-MS m/z: 155 (M$^+$), 56, 70, 86, 114.

1-(2,6-Dimethyl-4-morpholinyl)-3-buten-1-one

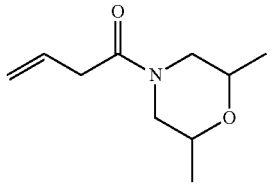

Yield: 72%. $^1$H-NMR (CDCl$_3$): δ 1.10-1.23 (d, J=6.2 Hz, 6H, CH$_3$ morph.), 2.13-2.37, 2.67-2.85, 3.35-3.64 and 4.30-4.51 (4 m, 6H, 2CH morph.+2CH$_2$ morph.), 5.00-5.22 (m, 2H, CH$_2$=CH), 5.75-6.05 (m, 1H, CH$_2$=CH). IR (CHCl$_3$) cm$^{-1}$: 1631 (C=O). GC-MS m/z: 183 (M$^+$), 41, 56, 69, 138, 142.

General procedure of 4-({3-[3-(cyclopentyloxy)-4-methoxyphenyl]-4,5-dihydroisoxazol-5-yl}acetyl) morpholine XIVa and 4-({3-[3-(cyclopentyloxy)-4-methoxyphenyl]-4,5-dihydroisoxazol-5-yl}acetil) 2,6-dimethylmorpholine XIVb (method B)

To a solution of 3-(cyclopentyloxy)-N-hydroxy-4-methoxybenzenecarboximidoyl chloride (2.97 g, 11 mmol) in an. DMF (20 mL) the suitable 1-amino-3-buten-1-one (22 mmol) solved in an. DMF (10 mL) was added; then, triethylamine (1.72 g, 17 mmol, 2.37 mL) was added dropwise at 0° C., under nitrogen atmosphere. The mixture was stirred at room temperature for 72 h, cooled to room temperature and poured into water (100 mL). The mixture was extracted with diethyl ether (3×20 mL), the organic phase was washed with brine (3×20 mL), dried (MgSO$_4$) and concentrated under reduced pressure. Compound XIVa was obtained as a yellow solid which was recrystallized by an. methanol. Compound XIVb was purified by silicagel (100-200 mesh) column chromatography using diethyl ether as the eluent to afford a pure product as a white solid.

4-({3-[3-(Cyclopentyloxy)-4-methoxyphenyl]-4,5-dihydroisoxazol-5-yl}acetyl)morpholine XIVa Yield: 41%. Mp: 144° C.

4-({3-[3-(Cyclopentyloxy)-4-methoxyphenyl]-4,5-dihydroisoxazol-5-yl}acetil) 2,6-dimethylmorpholine XIVb Yield: 40%. Mp: 104-105° C.

Synthesis of 1-{3-[3-(cyclopentyloxy)-4-methoxyphenyl]isoxazol-5-yl}ethanol

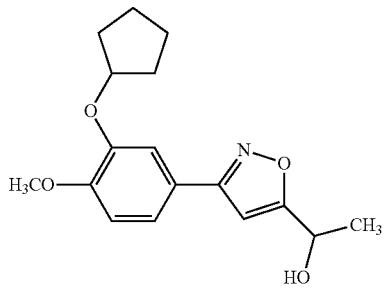 [SMILES: COc1ccc(-c2cc(C(C)O)on2)cc1OC1CCCC1]

To a solution of 3-(cyclopentyloxy)-N-hydroxy-4-methoxybenzenecarboximidoyl chloride (1.23 g, 4.56 mmol) in an. toluene (5 mL) at 0-5° C., 3-butyn-2-ol (0.36 mL, 4.56 mmol) and, subsequently, triethylamine (0.95 mL, 6.84 mmol) were added dropwise; then the mixture was heated at 60° C. for 18 h. After cooling to room temperature, the mixture was filtered and the solid obtained was washed with an. toluene (3×10 mL); the collected organic phases were washed with water (3×20 mL), dried (MgSO$_4$) and concentrated under reduced pressure yielding a yellow oil which was purified by Florisil (100-200 mesh) column chromatography using diethyl ether as the eluent. The crude crystallized as a white solid by addition of a mixture of diethyl ether/petroleum ether (boiling point 40-60° C.) (1:1).

Yield: 60%. Mp: 72-73° C. $^1$H-NMR (CDCl$_3$): δ 1.62 (d, J=6.6 Hz, 3H, CH$_3$), 1.75-2.10 (m, 8H, 4CH$_2$ cyclopent.), 2.02 (s, 1H, OH, disappears with D$_2$O), 3.87 (s, 3H, OCH$_3$), 4.75-4.91 (m, 1H, OCH cyclopent.), 4.95-5.11 (m, 1H, CH—OH), 6.44 (s, 1H, CH isox.), 6.88 (d, J=8.2 Hz, 1H, H-5 Ar), 7.24 (dd, J=8.2, 2.0 Hz, 1H, H-6 Ar), 7.37 (d, J=2.0 Hz, H-2 Ar). IR (KBr) cm$^{-1}$: 3398 (OH). Anal. (C$_{17}$H$_{21}$NO$_4$) C, H, N. (% calculated/found) C: 67.31/67.37; H: 6.98/7.35; N: 4.62/4.65.

Synthesis of 1-{3-[3-(cyclopentyloxy)-4-methoxyphenyl]isoxazol-5-yl}ethanone

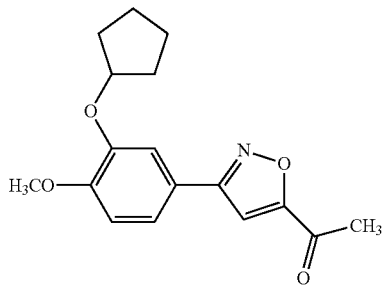 [SMILES: COc1ccc(-c2cc(C(C)=O)on2)cc1OC1CCCC1]

To 1-{3-[3-(cyclopentyloxy)-4-methoxyphenyl]isoxazol-5-yl}ethanol (4.18 g, 13.78 mmol) in dimethylsulfoxide (21 mL), acetic anhydride (13.78 mL) was added and the solution was stirred at room temperature for 24 h. Then water (230 mL) was added and the solid obtained was filtered and recrystallized by absolute ethanol yielding a white solid.

Yield: 80%. Mp: 121-122° C. $^1$H-NMR (CDCl$_3$): δ 1.42-2.10 (m, 8H, 4CH$_2$ cyclopent.), 2.63 (s, 3H, CH$_3$), 3.88 (s, 3H, OCH$_3$), 4.75-4.94 (m, 1H, OCH cyclopent.), 6.91 (d, J=8.2 Hz, 1H, Ar), 7.13 (s, 1H, CH isox.), 7.26 (dd, J=8.2, 2.0 Hz 1H, H-6 Ar), 7.39 (d, J=2.0 Hz, H-2 Ar). IR (KBr) cm$^{-1}$: 1696 (C=O). Anal. (C$_{17}$H$_{19}$NO$_4$) C, H, N. (% calculated/found) C: 67.76/67.95; H: 6.36/6.34; N: 4.65/5.00.

Synthesis of 2-bromo-1-{3-[3-(cyclopentyloxy)-4-methoxyphenyl]isoxazol-5-yl}ethanone

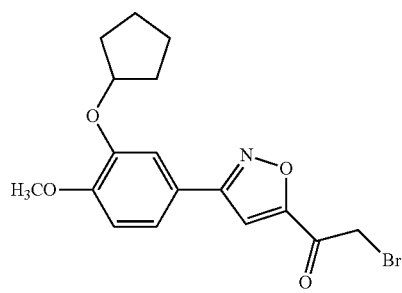 [SMILES: COc1ccc(-c2cc(C(=O)CBr)on2)cc1OC1CCCC1]

To a solution of 1-{3-[3-(cyclopentyloxy)-4-methoxyphenyl]isoxazol-5-yl}ethanone (0.56 g, 1.86 mmol) in CH$_2$Cl$_2$ (3 mL), glacial acetic acid (0.05 mL) was added and the reaction mixture was heated at 50° C. Afterward a solution of bromine (0.1 mL, 1.95 mmol) in CH$_2$Cl$_2$ (1 mL) was added dropwise and the mixture was heated at reflux for 1 h. After cooling to room temperature, the suspension was diluted with CH$_2$Cl$_2$ (20 mL), washed once with ice-water (20 mL), then with water (2×20 mL), dried (MgSO$_4$) and concentrated under reduced pressure yielding a yellow solid which was recrystallized by absolute ethanol to give the final product as a white solid.

Yield: 60%. Mp: 120-122° C. $^1$H-NMR (CDCl$_3$): δ 1.57-2.14 (m, 8H, 4CH$_2$ cyclopent.), 3.89 (s, 3H, OCH$_3$), 4.47 (s, 2H, CH$_2$Br), 4.78-4.93 (m, 1H, OCH cyclopent.), 6.93 (d, J=8.2 Hz, 1H, H-5 Ar), 7.20-7.37 (m, 2H, H-6 Ar+H isox.), 7.41 (d, J=1.8 Hz, H-2 Ar). IR (KBr) cm$^{-1}$: 1698 (C=O). Anal. (C$_{17}$H$_{18}$BrNO$_4$) C, H, N. (% calculated/found) C: 53.70/53.94; H: 4.77/5.10; N: 3.68/3.33.

General procedure for 1-{3-[3-(cyclopentyloxy)-4-methoxyphenyl]isoxazol-5-yl}-2-cycloaminoethanones XVa-b To a solution of 2-bromo-1-{3-[3-(cyclopentyloxy)-4-methoxyphenyl]isoxazol-5-yl}ethanone (0.54 g, 1.42 mmol) in CH$_2$Cl$_2$ (3 mL) cooled at −10° C. (for compound XVa) or at −30° C. (for compound XVb), the suitable cycloamine (2.91 mmol) was added. After a few minutes the reaction was completed and a saturated solution of anhydrous HCl in diethyl ether was immediately added to the reaction mixture yielding the hydrochloride salts of compounds XV as white solids.

1-{3-[3-(Cyclopentyloxy)-4-methoxyphenyl]isoxazol-5-yl}-2-morpholin-4-ylethanone hydrochloride XVa Yield: 72%. Mp: 175° C. (dec.). $^1$H-NMR (CDCl$_3$): δ 1.60-2.20 (m, 8H, 4CH$_2$ cyclopent.), 3.60-3.80 (m, 4H, 2CH$_2$—N morph.), 4.07 (s, 3H, OCH$_3$), 4.20-4.50 (m, 4H, 2CH$_2$O morph.), 4.27 (s, 2H, CH$_2$—N), 4.95-5.10 (m, 1H, OCH cyclopent.), 7.08 (d, J=2.0 Hz, 1H, H-5 Ar), 7.35-7.52 (m, 3H, H-2 Ar+H isox.+NH$^+$, 1H disappears with D$_2$O), 7.55 (d, J=2.0 Hz, 1H, H-6 Ar). IR (KBr) cm$^{-1}$: 1710 (C=O). Anal. (C$_{21}$H$_{26}$N$_2$O$_5$HCl) C, H, N. (% calculated/found) C: 59.64/59.63; H: 6.44/6.56; N: 6.62/6.69.

1-{3-[3-(Cyclopentyloxy)-4-methoxyphenyl]isoxazol-5-yl}-2-(2,6-dimethylmorpholin-4-yl)ethanone hydrochloride XVb Yield: 25%. Mp: 200° C. (dec.). $^1$H-NMR (CDCl$_3$): δ 1.41 and 1.44 (2 s, 6H, 2CH$_3$), 1.60-2.25 (2m, 8H, 4CH$_2$ cyclopent.), 3.05-3.22 and 3.65-3.87 (2 m, 4H, 2CH$_2$—N morph.), 4.06 (s, 3H, OCH$_3$), 4.45-4.68 (m, 2H, 2CHO morph.), 4.88 (s, 2H, CH$_2$—N), 4.95-5.10 (m, 1H, OCH cyclopent.), 7.08 (d, J=2.0 Hz, 1H, H-5 Ar), 7.47 (d, J=2.0 Hz, 1H, H-6 Ar), 7.55 (br s, 1H, H-2 Ar), 7.70 (s, 1H, H isox.). IR (KBr) cm$^{-1}$: 1711 (C=O). Anal. (C$_{23}$H$_{30}$N$_2$O$_5$.HCl) C, H, N. (% calculated/found) C: 60.99/61.08; H: 7.34/7.50; N: 6.18/6.20.

General procedure for 1-{3-[3-(cyclopentyloxy)-4-methoxyphenyl]isoxazol-5-yl}-2-cycloaminoethanols XVIa-b To a suspension of 1-{3-[3-(cyclopentyloxy)-4-methoxyphenyl]isoxazol-5-yl}-2-cycloaminoethanones hydrochloride XVa or XVb (1.1 mmol) in an. methanol, NaBH$_4$ (1.1 mmol, 41 mg) was added portionwise at room temperature; afterward a solution of CH$_3$ONa (60 mg, 1.1 mmol) in an. methanol (10 mL) was added dropwise and the mixture was stirred at room temperature for 3-4 h. Then, the methanol was removed under reduced pressure and the crude was solved in CH$_2$Cl$_2$ (20 mL), washed with water (3×20 mL), dried (MgSO$_4$) and concentrated under reduced pressure.

The morpholino derivative XVIa was obtained as a yellow solid which was washed with hot diethylic ether. The dimethylmorpholino derivative XVIb was obtained as an oil which was purified by Florisil (100-200 mesh) column chromatography eluting with diethyl ether. The solids obtained were further purified by preparative TLC (Silicagel) using diethyl ether as the eluent, yielding the final pure products as white solids.

1-{3-[3-(Cyclopentyloxy)-4-methoxyphenyl]isoxazol-5-yl}-2-morpholin-4-ylethanol XVIa Yield 65%. Mp: 136-137° C. $^1$H-NMR (CDCl$_3$): δ 1.70-2.30 (m, 8H, 4CH$_2$ cyclopent.), 2.55-2.75 (m, 2H, CH$_2$—N), 2.80-3.00 (m, 4H, 2CH$_2$—N morph.), 3.85-4.10 (m, 5H, 2CH$_2$—O morph.+OH, 1H disappears with D$_2$O), 4.05 (s, 3H, OCH$_3$), 4.85-5.15 (2m, 2H, OCH cyclopent.+CH—OH), 6.71 (s, 1H, H isox.), 7.08 (d, J=2.0 Hz, 1H, H-5 Ar), 7.24 (d, J=2.0 Hz, 1H, H-6 Ar), 7.35 (s, 1H, H-2 Ar) IR (KBr) cm$^{-1}$: 3125 (OH). Anal. (C$_{21}$H$_{28}$N$_2$O$_5$) C, H, N. (% calculated/found) C: 64.93/65.10; H: 7.27/7.50; N: 7.21/7.39.

1-{3-[3-(Cyclopentyloxy)-4-methoxyphenyl]isoxazol-5-yl}-2-(2,6-dimethylmorpholin-4-yl)ethanol XVIb Yield 30%. Mp: 92-94° C. $^1$H-NMR (CDCl$_3$) δ 1.30-1.42 (m, 6H, 2CH$_3$ morph.), 1.68-2.40 (m, 8H, 4CH$_2$ cyclopent.), 2.73-3.12 (m, 6H, 2CH$_2$ morph.+CH$_2$—N morph.), 3.65-4.00 (m, 2H, 2CH morph.), 4.05 (s, 3H, OCH$_3$), 4.95-5.20 (2 m, 2H, OCH cyclopent.+C<u>H</u>—OH), 7.05-7.13 (d, J=1.6 Hz, 1H, H-5 Ar), 7.43 (s, 1H, CH isox.), 7.46 (dd, J=1.6, 0.4Hz, 1H, H-6 Ar), 7.66 (d, J=0.4 Hz, 1H, H-2 Ar). IR (KBr) cm$^{-1}$: 3423 (OH). Anal. (C$_{23}$H$_{32}$N$_2$O$_5$) C, H, N. (% calculated/found) C: 66.32/66.16; H: 7.74/7.46; N: 6.73/6.74.

Synthesis of methyl 3-[3-(cyclopentyloxy)-4-methoxyphenyl]isoxazole-5-carboxylate

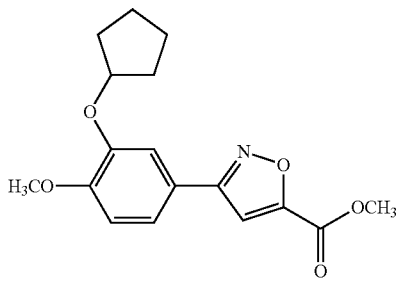 [SMILES: COC(=O)c1cc(-c2ccc(OC)c(OC3CCCC3)c2)no1]

To a suspension of 3-(cyclopentyloxy)-N-hydroxy-4-methoxybenzenecarboximidoyl chloride (2.33 g, 8.64 mmol) and methyl propiolate (0.73 g, 8.64 mmol, 0.71 mL) in an. toluene (10 mL), a solution of triethylamine (0.87 g, 8.64 mmol, 1.16 mL) in an. toluene (15 mL) was added dropwise (30 min) and the mixture was stirred at 60° C. for 12 h. After cooling to room temperature the solid residue was filtered off and washed with an. toluene. Then, the collected organic phases were dried (MgSO$_4$), and concentrated under reduced pressure yielding a light brown oil which crystallized after addition of a mixture of diethyl ether/petroleum ether (boiling point 40-60° C.) (1:1) and standing overnight in a refrigerator.

Yield: 33%. Mp: 126-127° C. $^1$H-NMR (CDCl$_3$): δ 1.55-2.15 (m, 8H, 4CH$_2$ cyclopent.), 3.93 (s, 3H, OCH$_3$ Ar), 4.02 (s, 3H, OCH$_3$ ester), 4.82-4.96 (m, 1H, OCH cyclopent.), 6.96 (d, J=8.2 Hz, 1H, H-5 Ar), 7.23 (s, 1H, H isox.), 7.30 (dd, J=8.2, 2.2 Hz, 1H, H-6 Ar), 7.45 (d, J=2.2 Hz, 1H, H-2 Ar). IR (KBr) cm$^{-1}$: 1744 (C=O). Anal. (C$_{17}$H$_{19}$NO$_5$) C, H, N. (% calculated/found) C: 64.34;/64.18; H: 6.03/6.36; N: 4.41/4.56.

General procedure for 4-({3-[3-(cyclopentyloxy)-4-methoxyphenyl]isoxazol-5-yl}carbonyl)cycloamines XVIIa-b A suspension of methyl 3-[3-(cyclopentyloxy)-4-methoxyphenyl]isoxazole-5-carboxylate (0.96 g, 2.90 mmol) and an excess of the proper cycloamine (41.6 mmol) was stirred for 12 h at 60° C. After cooling to room temperature, water (30 mL) was added and the product crystallized after standing overnight in a refrigerator. The white solid obtained was filtered and recrystallised by ethanol.

4-({3-[3-(Cyclopentyloxy)-4-methoxyphenyl]isoxazol-5-yl}carbonyl)morpholine XVIIa

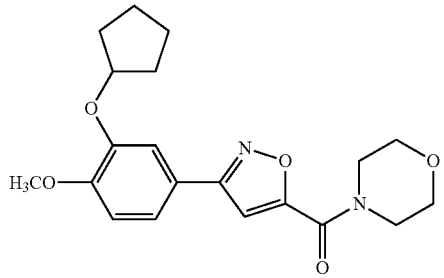 [SMILES: COc1ccc(-c2cc(C(=O)N3CCOCC3)on2)cc1OC1CCCC1]

Yield: 53%. Mp: 100-101° C. $^1$H-NMR (CDCl$_3$): δ 1.55-2.21 (m, 8H, 4CH$_2$ cyclopent.), 3.92 (s, 3H, OCH$_3$), 3.65-3.97 (m, 8H, 4CH$_2$ morph.), 4.80-4.92 (m, 1CH, OCH cyclopent.), 6.96 (d, J=8 Hz, 1H, H-5 Ar), 7.09 (s, 1H, H isox.), 7.03-7.38 (dd, J=8.0, 1.8 Hz, 1H, H-6 Ar), 7.42 (d, J=1.8 Hz, 1H, H-2 Ar). IR (KBr) cm$^{-1}$: 1636 (C=O). Anal. (C$_{20}$H$_{24}$N$_2$O$_5$) C, H, N. (% calculated/found) C: 64.50/65.25; H: 6.50/6.87; N: 7.52/7.86.

4-({3-[3-(Cyclopentyloxy)-4-methoxyphenyl]isoxazol-5-yl}carbonyl)-2,6-dimethylmorpholine XVIIb

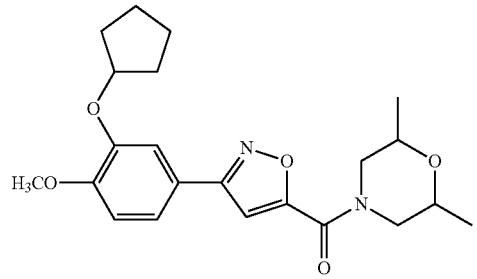 [SMILES: COc1ccc(-c2cc(C(=O)N3CC(C)OC(C)C3)on2)cc1OC1CCCC1]

Yield: 69%. Mp: 152-153° C. $^1$H-NMR (CDCl$_3$): δ 1.13-1.35 (m, 6H, 2CH$_3$ morph.), 1.55-2.12 (m, 8H, 4CH$_2$ cyclopent.), 2.45-2.70, 2.90-3.15, 3.50-3.80, 4.00-4.28 and 4.40-4.60 (5 m, 6H, 2CH morph.+2CH$_2$—N morph.) 3.93 (s, 3H, OCH$_3$), 4.75-4.93 (m, 1 CH, OCH cyclopent.), 6.96 (d, J=11.4 Hz, 1H, H-5 Ar), 7.09 (s, 1H, H isox.), 7.31 (dd, J=11.4, 2.0 Hz, 1H, H-6 Ar), 7.44 (d, J=2.0 Hz, 1H, H-2 Ar). IR (KBr) cm$^{-1}$: 1633 (C=O). Anal. (C$_{22}$H$_{28}$N$_2$O$_5$) C, H, N. (% calculated/found) C: 65.98/65.96; H: 7.05/6.86; N: 7.00/7.34.

Synthesis of 3-[3-(cyclopentyloxy)-4-methoxyphenyl]-1H-pyrazole

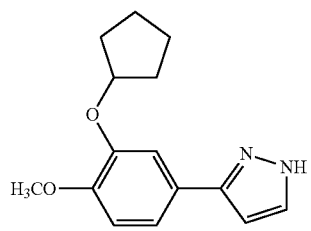 [SMILES: COc1ccc(-c2cc[nH]n2)cc1OC1CCCC1]

This compound has been already reported [Hopper, Allen et al. PCT Int. Appl., 2004094411, 04 Nov. 2004]. We describe below our different method for its preparation.

To a solution of p-toluenesulfonyl hydrazide (3.3 g, 17.74 mmol) in an. acetonitrile (20 mL) 3-(cyclopentyloxy)-4-methoxybenzaldehyde (3.90 g, 17.74 mmol) solved in an. acetonitrile (10 mL) was added and the mixture was stirred at room temperature for 1 h. Then, 5N NaOH solution (3.55 mL, 17.75 mmol) was added and the mixture, which became coloured in red, was stirred at room temperature for 20 min. Afterward, 1-vinylimidazole (8.34 g, 88.77 mmol, 8.03 mL) was slowly added and the mixture was heated at 50° C. for 48 h. After cooling to room temperature, the solvent was removed under reduced pressure and the crude was solved in ethylacetate (20 mL); the organic phase was washed with brine (2×20 mL), 1N HCl solution (20 mL), water (3×20 mL), dried (MgSO$_4$), and concentrated under reduced pressure to afford a light yellow oil which crystallized by addition of methanol. The pure product is obtained as a light yellow solid.

Yield: 65%. Mp: 80-82° C. $^1$H-NMR (CDCl$_3$): δ 1.49-2.19 (m, 8H, 4CH$_2$ cyclopent.), 3.87 (s, 3H, OCH$_3$), 4.72-4.97 (m, 1H, OCH cyclopent.), 6.53 (d, J=2.2 Hz, 1H, H-4 pyraz.), 6.84-7.38 (m, 3H, 3H Ar), 7.59 (d, J=2.2 Hz, 1H, H-5 pyraz.). IR (KBr) cm$^{-1}$: 3562 (NH). Anal. (C$_{15}$H$_{18}$N$_2$O$_2$) C, H, N. (% calculated/found) C: 69.74/69.74; H: 7.02/6.84; N: 10.84/10.73.

Synthesis of 3-[3-(cyclopentyloxy)-4-methoxyphenyl]-1-(oxiran-2-ylmethyl)-1H-pyrazole

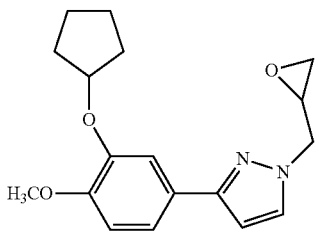 [SMILES: COc1ccc(-c2ccn(CC3CO3)n2)cc1OC1CCCC1]

A mixture of 3-[3-(cyclopentyloxy)-4-methoxyphenyl]-1H-pyrazole (0.77 g, 2.98 mmol) and epichlorohydrin (3 mL, 38.26 mmol) was cooled at 5° C.; then, triethylamine (4.47 mmol, 0.62 mL,) was added dropwise and the reaction mixture was stirred until the temperature became 25° C., then was heated at 70° C. for 3 h. After cooling to room temperature, the mixture was poured into water (100 mL), the aqueous phase was extracted with CH$_2$Cl$_2$ (2×20 mL); the organic phase was washed with water (20 mL) until the pH of washing solution became neutral, dried (MgSO$_4$) and concentrated under reduced pressure yielding an oil which was purified by silicagel (100-200 mesh) column chromatography using diethyl ether as the eluent. The desired compound crystallized standing in a refrigerator after addition of diethyl ether.

The reaction between 3-[3-(cyclopentyloxy)-4-methoxyphenyl]-1H-pyrazole and epichlorohydrin could lead to 1-5 and/or 1-3 disubstituted isomers. From the $^1$H and $^{13}$C-NMR spectra resulted that the purified compound was a single isomer and C and H assignments were made on the basis of spin-spin decoupling, COSY, HSQC and HMBC experiments. Furthermore a clear long range correlation δ$_C$=131.4 (C-5 pyrazole)/δ$_H$=4.19 and 4.48 (N—CH$_2$—) in the HMBC spectrum clearly showed a 1,3-disubstituted pyrazole structure for the synthesized compound.

Yield: 73%. Mp: 53-55° C. $^1$H-NMR (CDCl$_3$): δ 1.50-2.04 (m, 8H, 4CH$_2$ cyclopent.), 2.53 (dd, J=4.7, 2.6 Hz, 1H, H$_A$ of CH$_2$ epox.), 2.85 (dd, J=4.7, 4.3 Hz, 1H, H$_B$ of CH$_2$ epox.), 3.34-3.40 (m, 1H, CHO epox.), 3.86 (s, 3H, OCH$_3$), 4.19 (dd, J=4.6, 5.6 Hz, 1H, H$_A$ of CH$_2$), 4.48 (dd, J=14.6, 3.1 Hz, 1H, H$_B$ of CH$_2$), 4.84-4.94 (m, 1H, OCH cyclopent.), 6.49 (d, J=2.4 Hz, 1H, H-4 pyraz.), 6.88 (d, J=8.3 Hz, 1H, H-5 Ar), 7.29 (dd, J=8.3, 2.0 Hz, 1H, H-6 Ar), 7.36 (d, J=2.0 Hz, 1H, H-2 Ar), 7.46 (d, J=2.4 Hz, 1H, H-5 pyraz.). $^{13}$C-NMR (CDCl$_3$): 24.2 (2CH$_2$ cyclopent.), 32.9 (2CH$_2$ cyclopent.), 45.5 (2CH$_2$ cyclopent. epox.), 50.8 (CH epox.), 53.8 (CH$_2$N), 56.1 (OCH$_3$), 80.5 (OCH cyclopent.), 103.0 (C-4 pyraz.), 112.0 (C-5 Ar), 112.7 (C-2 Ar), 118.3 (C-6 Ar), 126.5 (C-1 Ar), 131.4 (C-5 pyraz.), 147.8 (C-3 Ar), 150.0 (C-4 Ar), 151.8 (C-3 pyraz.). Anal. (C$_{18}$H$_{22}$N$_2$O$_3$) C, H, N. (% calculated/found) C: 68.77/68.58; H: 7.05/6.68; N: 8.91/8.84.

General procedure for 3-[3-(cyclopentyloxy)-4-methoxyphenyl]-1H-pyrazol-1-yl]-3-cycloaminopropan-2-ols XVIIIa,b To 3-[3-(cyclopentyloxy)-4-methoxyphenyl]-1-(oxiran-2-ylmethyl)-1H-pyrazole (1 g, 3.15 mmol) an excess of the suitable amine (2 mL) was added and the mixture was heated at 50-60° C. for 18 h. After cooling to room temperature, the mixture was diluted with diethyl ether (20 mL), then the organic phase was washed with water (20 mL), dried (MgSO$_4$) and concentrated under reduced pressure. The crude was purified by Florisil (100-200 mesh) column chromatography using diethyl ether as the eluent. The desired compounds were obtained as yellow oils which was then treated with a HCl saturated ethanol solution to afford the corresponding hydrochloride salts as white solids.

1-{3-[3-(Cyclopentyloxy)-4-methoxyphenyl]-1H-pyrazol-1-yl}-3-morpholin-4-ylpropan-2-ol dihydrochloride XVIIa

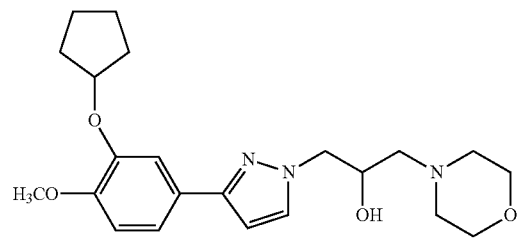 [SMILES: COc1ccc(-c2ccn(CC(O)CN3CCOCC3)n2)cc1OC1CCCC1]

Yield: 51%. Mp: 162-163° C. $^1$H-NMR (CDCl$_3$): δ 1.70-2.40 (m, 8H, 4CH$_2$ cyclopent.), 3.20-3.60, 3.74-4.00, 4.10-4.25 and 4.25-4.50 (4m, 10H, 4CH$_2$ morph.+CH$_2$N), 4.05 (s, 3H, OCH$_3$), 4.80-5.35 (m, 5H, OCH cyclopent.+CH—OH+CH$_2$N pyraz.+OH, 1H disappears with D$_2$O), 6.85 (br s, 1H, H-4 pyraz.), 7.09 (d, J=8.2 Hz, 1H, H-5 Ar), 7.60 (d, J=8.2 Hz, 1H, H-6 Ar), 7.75 (s, 1H, H-2 Ar), 8.24 (s, 1H, H-5 pyraz.), 11.70-11.95 (br s, 1H, NH$^+$ disappears with D$_2$O). Anal. (C$_{22}$H$_{31}$N$_3$O$_4$.2HCl.2H$_2$O) C, H, N. (% calculated/found) C: 51.77/51.43; H: 7.31/6.86; N: 8.23/8.26.

1-{3-[3-(Cyclopentyloxy)-4-methoxyphenyl]-1H-pyrazol-1-yl}-3-(2,6-dimethylmorpholin-4-yl)propan-2-ol dihydrocloride XVIIIb

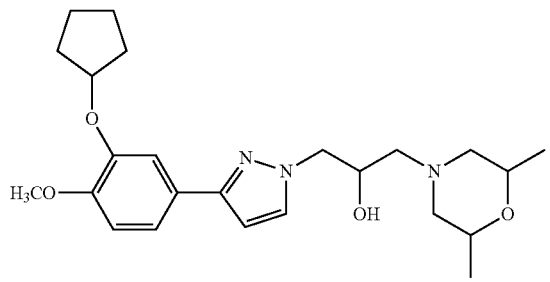 [SMILES: COc1ccc(-c2ccn(CC(O)CN3CC(C)OC(C)C3)n2)cc1OC1CCCC1]

Yield: 61%. Mp: 188-189° C. ¹H-NMR (CDCl₃): δ 1.17-1.40 (m, 6H, 2CH₃), 1.55-2.20 (m, 8H, 4CH₂ cyclopent.), 2.50-2.80 (m, 2H, CH₂N morph.), 3.00-3.40 (m, 2H, CH₂N), 3.45-3.80 (m, 3H, CH₂N morph.+CHO morph.), 3.80-4.00 (m, 4H, OCH₃+CHO morph.), 4.20-4.55 (m, 2H, CH₂N pyraz.), 4.80-5.20 (m, 3H, OCH cyclopent.+CH—OH+OH, 1H disappears with D₂O), 6.72 (near d, 1H, H-4 pyraz.), 6.96 (d, J=8.4 Hz, 1H, H-5 Ar), 7.48 (dd, J=8.4, 2 Hz, 1H, H-6 Ar), 7.61 (d, J=2 Hz, 1H, H-2 Ar), 8.18 (near d, 1H, H-5 pyraz.), 11.55 (br s, 2H, 2NH⁺, 2H disappear with D₂O). Anal. (C₂₄H₃₅N₃O₄.2HCl.H₂O) C, H, N. (% calculated/found) C: 55.38/55.67; H: 7.55/7.46; N: 8.07/8.16.

Synthesis of 1-(3-{3-[3-(cyclopentyloxy)-4-methoxyphenyl]4H-pyrazol-1-yl}-2-hydroxypropyl)piperidin-4-ol c

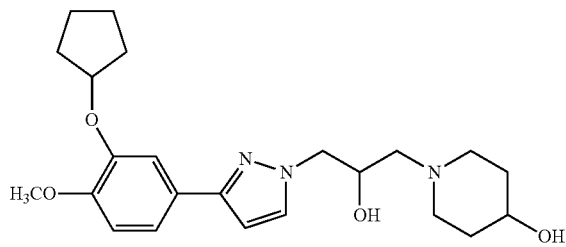 [SMILES: COc1ccc(-c2ccn(CC(O)CN3CCC(O)CC3)n2)cc1OC1CCCC1]

To a solution of 3-[3-(cyclopentyloxy)-4-methoxyphenyl]-1-(oxiran-2-ylmethyl)-1H-pyrazole (0.38 g, 1.21 mmol) in an. DMF (2 mL), piperidin-4-ol (0.25 g, 2.5 mmol) was added. The mixture was stirred at 50-60° C. for 18 h. After cooling to room temperature, the solvent was removed under reduced pressure. The residue was dissolved in diethyl ether (20 mL) and the organic phase was washed with water (20 mL), dried (Na₂SO₄), and concentrated under reduced pressure. The crude was purified by silicagel (100-200 mesh) column chromatography using as eluent firstly a mixture of diethyl ether/methanol (9:1), then a mixture of dichloromethane/methanol (7:3) obtaining a pure product as a light yellow oil.

Yield: 40%. ¹H-NMR (CDCl₃): δ 1.30-2.03 (m, 12H, 4CH₂ cyclopent.+2CH₂ pip.), 2.03-2.99 (m, 8H, 3CH₂N+2OH, 2H disappear with D₂O), 3.60-3.80 (m, 1H, CH—OH pip.), 3.88 (s, 3H, OCH₃), 4.04-4.28 (m, 3H, CH₂N pyraz.+CH—OH), 4.78-4.98 (m, 1H, OCH cyclopent.), 6.49 (d, J=2 Hz, 1H, H-4 pyraz.), 6.82-7.48 (2m, 3H, H-6+H-5+H-2 Ar), 7.52 (d, J=2.0 Hz, 1H, H-5 pyraz.). IR (KBr) cm⁻¹: 3413 (OH). Anal. (C₂₃H₃₃N₃O₄) C, H, N. (% calculated/found) C: 66.48/66.09; H: 8.00/8.29; N: 10.11/10.00.

Synthesis of 2-{3-[3-(cyclopentyloxy)-4-methoxyphenyl]-1H-pyrazol-1-yl}-1-(morpholin-4-ylmethyl)ethyl acetate XIX

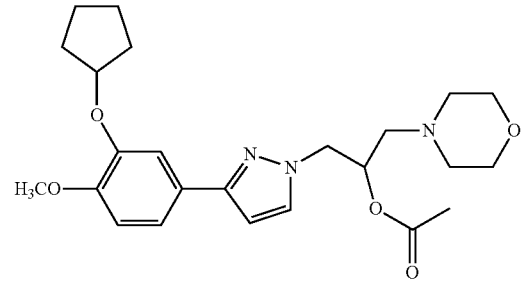 [SMILES: COc1ccc(-c2ccn(CC(CN3CCOCC3)OC(C)=O)n2)cc1OC1CCCC1]

A mixture of 1-{3-[3-(cyclopentyloxy)-4-methoxyphenyl]-1H-pyrazol-1-yl}-3-morpholin-4-ylpropan-2-ol (0.60 g, 1.63 mmol) and sodium acetate (0.2 g, 2.4 mmol) in acetic anhydride (5 mL) was heated at 40-50° C. for 5 h. After cooling to room temperature, the mixture was poured into water (100 mL), extracted with diethyl ether (3×10 mL), the organic phase was washed with water (3×20 mL), brine (3×20 mL), dried (MgSO₄) and concentrated under reduced pressure. The pure product was obtained as a yellow oil.

Yield: 52%. ¹H-NMR (CDCl₃): δ 1.56-2.06 (m, 8H, 4CH₂ cyclopent.), 2.12 (s, 3H, CH₃), 2.61-2.92 (m, 6H, 2CH₂N morph.+CH₂N), 3.70-4.00 (m, 7H, OCH₃+2 CH₂O morph.), 4.32-4.58 (m, 2H, CH₂N pyraz.), 4.81-4.99 (m, 1H, OCH cyclopent.), 5.40-5.57 (m, 1H, CHOAc), 6.50 (d, J=1.6 Hz, 1H, H-4 pyraz.), 6.84-7.60 (m, 4H, H-6+H-5+H-2 Ar+H-5 pyraz.). Anal. (C₂₄H₃₃N₃O₅) C, H, N. (% calculated/found) C: 64.99/64.93; H: 7.50/7.79; N: 9.47/9.10.

General procedure for 4-({3-[3-(cyclopentyloxy)-4-methoxyphenyl]4H-pyrazol-1-yl}acetyl)amines XXa,b To a solution of 3-[3-(cyclopentyloxy)-4-methoxyphenyl]-1H-pyrazole (0.52 g, 2 mmol) in an. DMF (3 mL) the suitable chloroacetylamine (15 mmol) was added. Then, triethylamine (1 mL, 0.73 g, 7.19 mmol) was added dropwise and the mixture was heated at 100° C. for 18 h. After cooling to room temperature, the mixture was poured into water (100 mL) and extracted with diethyl ether (3×25 mL), the organic phase was dried (MgSO₄) and concentrated under reduced pressure. The crude crystallized by addition of a mixture of diethyl ether/petroleum ether (boiling point 40-60° C.) (1:1) to afford the desired compounds as white solids, which were recrystallized by absolute ethanol (XXa) or diethyl ether (XXb).

4-({3-[3-(Cyclopentyloxy)-4-methoxyphenyl]-1H-pyrazol-1-yl}acetyl)morpholine XXa

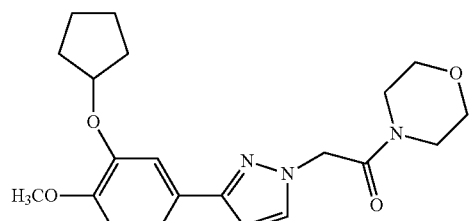

Yield: 58%. Mp: 131-132° C. $^1$H-NMR (CDCl$_3$): δ 1.60-2.12 (m, 8H, 4CH$_2$ cyclopent.), 3.60-4.00 (m, 11H, OCH$_3$+4CH$_2$ morph.), 4.83-5.10 (m, 3H, CH$_2$CO+OCH cyclopent.), 6.76 (d, J=2.8 Hz, 1H, H-4 pyraz.), 6.96 (d, J=8.2 Hz, 1H, H-5 Ar), 7.47 (dd, J=8.2, 1.6 Hz, 1H, H-6 Ar), 7.68 (d, J=1.6 Hz, 1H, H-2 Ar), 7.84 (d, J=2.8 Hz, 1H, H-5 pyraz.). IR (KBr) cm$^{-1}$: 1663 (C=O). Anal. (C$_{21}$H$_{27}$N$_3$O$_4$) C, H, N. (% calculated/found) C: 65.44/65.60; H: 7.06/7.44; N: 10.90/10.81.

4-({3-[3-(Cyclopentyloxy)-4-methoxyphenyl]-1H-pyrazol-1-yl}acetyl)2,6-dimethylmorpholine XXb

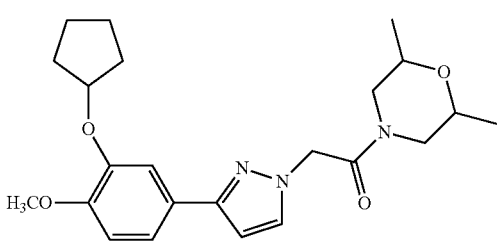 [SMILES: COc1ccc(-c2ccn(CC(=O)N3CC(C)OC(C)C3)n2)cc1OC1CCCC1]

Yield: 53%, Mp: 99-100° C. $^1$H-NMR (CDCl$_3$): δ 1.10-1.28 (m, 6H, 2CH$_3$ morph.), 1.52-2.06 (m, 8H, 4CH$_2$ cyclopent.), 2.18-2.52, 2.79-2.98 and 3.12-3.61 (3m, 4H, CH$_2$ morph.), 3.65-3.80 (m, 1H, CHO morph.), 3.82-4.00 (m, 4H, OCH$_3$+CHO morph.), 4.91 (s, 2H, CH$_2$CO), 5.00-5.19 (m, 1H, OCH cyclopent.), 6.55 (d, J=2.4 Hz, 1H, H-4 pyraz.), 6.90 (d, J=8.4 Hz, 1H, H-5 Ar), 7.25-7.42 (m, 2H, H-6+H-2 Ar), 7.56 (d, J=2.4 Hz, 1H, H-5 pyraz.). IR (KBr) cm$^{-1}$: 1665 (C=O). Anal. (C$_{23}$H$_{31}$N$_3$O$_4$) C, H, N. (% calculated/found) C: 66.81/66.81; H: 7.56/7.85; N: 10.16/10.21.

Synthesis of 4-(3-{3-[3-(cyclopentyloxy)-4-methoxyphenyl]-1H-pyrazol-1-yl}propanoyl)morpholine XXIa

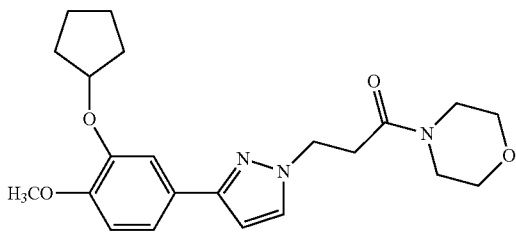 [SMILES: COc1ccc(-c2ccn(CCC(=O)N3CCOCC3)n2)cc1OC1CCCC1]

To a solution of 3-[3-(cyclopentyloxy)-4-methoxyphenyl]-1H-pyrazole (0.77 g, 3 mmol) in an. DMF (5 mL) 4-(3-chloropropanoyl)morpholine (3.20 g, 18 mmol) solved in an. DMF (6 mL) was slowly added at 0° C. Then, triethylamine (0.80 g, 7.91 mmol, 1.1 mL) was added dropwise and the mixture was heated at 120° C. for 48 h. After cooling to room temperature, the mixture was poured into water (100 mL) and extracted with diethyl ether (3×25 mL), the organic phase was dried (MgSO$_4$) and concentrated under reduced pressure. The crude was purified by silicagel (100-200 mesh) column chromatography using a gradient elution from diethyl ether alone to diethyl ether/methanol (1:1). The pure product was obtained as a light yellow oil.

Yield: 38%. $^1$H-NMR (CDCl$_3$): δ 1.54-2.07 (m, 8H, 4CH$_2$ cyclopent.), 2.91-3.00 (m, 2H, CH$_2$CO), 3.32-3.67 (m, 8H, 4CH$_2$ morph.), 3.89 (s, 3H, OCH$_3$), 4.52 (t, J=6.4 Hz, 2H, CH$_2$N), 4.89-5.00 (m, 1H, OCH cyclopent.), 6.44 (d, J=2.4 Hz, 1H, H-4 pyraz.), 6.92 (d, J=8.2 Hz, 1H, H-5 Ar), 7.22-7.40 (m, 2H, H-6+H-2 Ar), 7.49 (d, J=2.4 Hz, 1H, H-5 pyraz.). IR (film) cm$^{-1}$: 1654 (C=O). Anal. (C$_{22}$H$_{29}$N$_3$O$_4$) C, H, N. (% calculated/found) C: 66.14/66.07; H: 7.32/7.04; N: 10.52/10.46.

Synthesis of methyl 3-{3-[3-(cyclopentyloxy)-4-methoxyphenyl]4H-pyrazol-1-yl}-propanoate

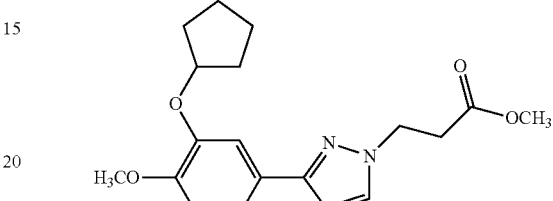

To a solution of 3-[3-(cyclopentyloxy)-4-methoxyphenyl]-1H-pyrazole (0.6 g, 2.25 mmol) in an. acetonitrile (15 mL) methyl-3-bromopropionate (1.91 g, 11.45 mmol) and triethylamine (1 mL, 0.73 g, 7.19 mmoli) were added dropwise at 0° C.; then, the mixture was heated at reflux for 48 h. After cooling to room temperature, the solvent was removed under reduced pressure and the crude was solved in diethyl ether (30 mL), the organic phase was washed with water (3×20 mL), 4N NaOH solution (2×20 mL), brine (2×20 mL), dried (MgSO$_4$), and concentrated under reduced pressure. The obtained oil was purified by silicagel (100-200 mesh) column chromatography, using diethyl ether as the eluent to afford the pure product as a light yellow oil.

Yield: 67%. $^1$H-NMR (CDCl$_3$): δ 1.50-2.18 (m, 8H, 4CH$_2$ cyclopent.), 3.00 (t, J=6.0 Hz, 2H, CH$_2$CO), 3.73 (s, 3H, OCH$_3$), 3.90 (s, 3H, OCH$_3$—Ar), 4.49 (t, J=6.0 Hz, 2H, CH$_2$N), 4.77-5.08 (m, 1H, OCH cyclopent.), 6.45 (d, J=3.0 Hz, 1H, H-4 pyraz.), 6.95 (d, J=6.8 Hz, 1H, H-5 Ar), 7.20-7.50 (m, 3H, H-6+H-2 Ar+H-5 pyraz.). IR (CHCl$_3$) cm$^{-1}$: 1735 (C=0). Anal. (C$_{19}$H$_{24}$N$_2$O$_4$) C, H, N. (% calculated/found) C: 66.26/66.24; H: 7.02/7.33; N: 8.13/7.90.

Synthesis of 3-{3-[3-(cyclopentyloxy)-4-methoxyphenyl]-1H-pyrazol-1-yl}-propanoic acid

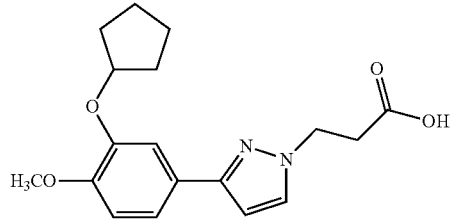 [SMILES: COc1ccc(-c2ccn(CCC(=O)O)n2)cc1OC1CCCC1]

To a solution of methyl 3-{3-[3-(cyclopentyloxy)-4-methoxyphenyl]-1H-pyrazol-1-yl}-propanoate (1 g, 3 mmol) in 96% ethanol (3 mL) NaOH (0.2 g, 5.0 mmol) was added and the mixture was heated at 60° C. for 4 h. Then, the solvent was removed under reduced pressure, the crude was solved in water (20 mL) and a 1N HCl solution was slowly added until pH became=1. The light yellow solid obtained was filtered, washed with water and recrystallized by a mixture of diethyl ether/dichlorometane (1:1).

Yield: 74%. Mp: 131-133° C. $^1$H-NMR (CDCl$_3$): δ 1.52-2.11 (m, 8H, 4CH$_2$ cyclopent.), 3.02-3.10 (m, 2H, CH$_2$), 3.91 (s, 3H, OCH$_3$), 4.42-4.54 (m, 2H, CH$_2$N pyraz.), 4.86-5.02 (m, 1H OCH cyclopent.), 6.54 (d, J=2.3 Hz, 1H, H-4 pyraz.), 6.93 (d, J=8.4 Hz, 1H, H-5 Ar), 7.21-7.41 (m, 2H, H-6+H-2 Ar), 7.52 (d, J=2.3 Hz, 1H, H-5 pyraz.). IR (CHCl$_3$) cm$^{-1}$: 1721 (C=O), 3515 (OH). Anal. (C$_{18}$H$_{22}$N$_2$O$_4$) C, H, N. (% calculated/found) C: 65.44/65.62; H: 6.71/6.45; N: 8.48/8.48.

Synthesis of 4-(3-{3-[3-(cyclopentyloxy)-4-methoxyphenyl]-1H-pyrazol-1-yl}propanoyl)2,6-dimethylmorpholine XXIb

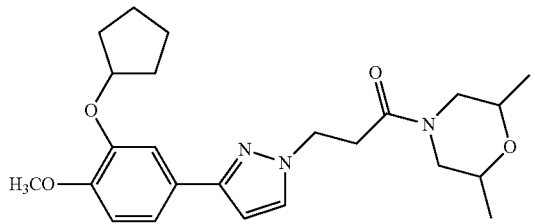 [SMILES: COc1ccc(-c2ccn(CCC(=O)N3CC(C)OC(C)C3)n2)cc1OC1CCCC1]

To a solution of 3-{3-[3-(cyclopentyloxy)-4-methoxyphenyl]-1H-pyrazol-1-yl}-propanoic acid (0.67 g, 2 mmol) in an. DMF (5 mL), triethylamine (0.30 g, 6 mmol, 0.4 mL), 2,6-dimethylmorpholine (0.50 mL, 4 mmol) and diphenylphosphorylazide (0.69 g, 2.5 mmol) were added at 0° C. Then, the mixture was heated at 80° C. for 15 h. After cooling to room temperature, the mixture was poured into water (100 mL) and extracted with diethyl ether (3×25 mL), the organic phase was dried (MgSO$_4$) and concentrated under reduced pressure. The crude was purified by silicagel (100-200 mesh) column chromatography using diethyl ether as the eluent to afford the pure product as a light yellow oil.

Yield: 71%. $^1$H-NMR (CDCl$_3$): δ 1.08 (d, J=6.2 Hz, 3H, CH$_3$ morph), 1.18 (d, J=6.2 Hz, 3H, CH$_3$ morph.), 1.60-2.06 (m, 8H, 4CH$_2$ cyclopent.), 2.23-2.39, 2.62-2.7, 2.82-3.19 and 3.23-3.70 (4 m, 8H, 2CH$_2$ morph.+CH$_2$CO+2CH morph.), 3.89 (s, 3H, OCH$_3$), 4.50-4.59 (m, 2H, CH$_2$N pyraz.), 4.86-4.97 (m, 1H, CHO cyclopent.), 6.43 (d, J=2.2 Hz, 1H, H-4 pyraz.), 6.93 (d, J=8.4 Hz, 1H, H-5 Ar), 7.33-7.41 (m, 2H, H-6+H-2 Ar), 7.48 (d, J=2.2 Hz, 1H, H-5 pyraz.). IR (CHCl$_3$) cm$^{-1}$: 1671 (C=O). Anal. (C$_{24}$H$_{33}$N$_3$O$_4$) C, H, N. (% calculated/found) C: 67.42/67.15; H: 7.78/8.11; N: 9.83/9.84.

Synthesis of 4-(difluoromethoxy)-3-hydroxybenzaldehyde

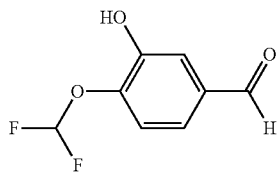 [SMILES: O=Cc1ccc(OC(F)F)c(O)c1]

The 4-(difluoromethoxy)-3-hydroxybenzaldehyde was prepared with improved yield by the following microwave assisted procedure.

To a solution of 3,4-dihydroxybenzaldehyde (0.415 g, 3 mmol) in an. DMF (5 mL), Cs$_2$CO$_3$ (0.975 g, 3 mmol) and methyl chlorodifluoroacetate (0.520 g, 3.6 mmol) were added; then the mixture was irradiated with microwaves, under pressure, increasing the potency until 300 W in 2 minutes and cooling by compressed air to avoid the temperature increasing over 90° C.; the irradiation was carried on for further 3 minutes and then the mixture was cooled to room temperature, with compressed air, in 1 minute. The cycle was repeated five time for a total reaction time of 30 minutes. The mixture was poured into water (100 mL) and extracted with ethyl acetate (3×20 mL); the organic phase was washed with water (20 mL), brine (20 mL), dried (MgSO$_4$) and concentrated under reduced pressure, yielding a brown oil which was purified by silicagel (100-200 mesh) column chromatography eluting with an ethylacetate/exane mixture (15:85). The pure product was obtained as a light grey solid.

Yield: 57% (lit.: 15-30%). Mp: 86-88° C. $^1$H-NMR (CDCl$_3$): δ 6.05 (br s, 1H, OH, 1H disappears with D$_2$O), 6.65 (t, J=72.6 Hz, OCHF$_2$), 7.26 (d, J=8.2 Hz, 1H, H-5 Ar), 7.45 (dd, J=8.2, 2.0 Hz, 1H, H-6 Ar), 7.12 (d, J=2.0 Hz, H-2 Ar), 9.90 (s, 1H, CH=N). IR (KBr)(cm$^{-1}$): 1687 (C=O), 3305 (OH). Anal. (C$_8$H$_6$F$_2$O$_3$) C, H. (% calculated/found) C: 51.07/50.96; H: 3.21/3.31.

Synthesis of 3-[3-(cyclopentyloxy)-4-(difluoromethoxy)phenyl]-1H-pyrazole

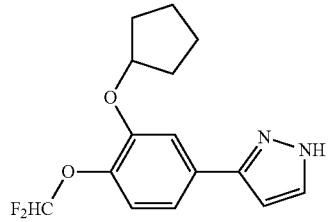

To a solution of p-toluenesulfonyl hydrazide (1.2 g, 6.45 mmol) in an. acetonitrile (7 mL) 3-(cyclopentyloxy)-4-(difluoromethoxy)benzaldehyde (1.65 g, 6.45 mmol) solved in an. acetonitrile (2 mL) was added and the mixture was stirred at room temperature for 1 h. Then, 5N NaOH solution (1.29 mL, 6.45 mmol) was added and the mixture, which became coloured in red, was stirred at room temperature for 20 min. Afterward, 1-vinylimidazole (3.04 g, 32.25 mmol, 2.92 mL) was slowly added and the mixture was heated at 50° C. for 48 h. After cooling to room temperature, the solvent was removed under reduced pressure and the crude was solved in ethylacetate (10 mL); the organic phase was washed with brine (2×10 mL), 1N HCl solution (10 mL), water (3×10 mL), dried (MgSO$_4$), and concentrated under reduced pressure to afford a light yellow oil which was purified by flash Silicagel column chromatography using CH$_2$Cl$_2$ as eluent. The pure product is obtained as a light yellow oil.

Yield: 45%. $^1$H-NMR (CDCl$_3$): δ 1.52-1.94 (m, 8H, 4CH$_2$ cyclopent.), 4.80-5.00 (m, 1H, OCH cyclopent.), 6.55-7.70 (m, 7H,-3H Ar+H-5 pyraz.+H-4 pyraz+OCHF$_2$+NH pyraz.).

Anal. (C₁₅H₁₆N₂O₂F₂) C, H, N. (% calculated/found) C: 61.22/61.32; H: 5.48/5.71; N: 9.52/9.59.

Synthesis of 3-[3-(cyclopentyloxy)-4-(difluoromethoxy)phenyl]-1-(oxiran-2-ylmethyl)-1H-pyrazole

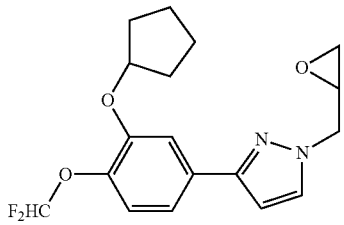 [SMILES: FC(F)Oc1ccc(-c2ccn(CC3CO3)n2)cc1OC1CCCC1]

A mixture of 3-[3-(cyclopentyloxy)-4-methoxyphenyl]-1H-pyrazole (1.3 g, 4.42 mmol) and epichlorohydrin (4.5 mL, 57.77 mmol) was cooled at 5° C.; then, triethylamine (6.63 mmol, 0.92 mL,) was added dropwise and the reaction mixture was stirred until the temperature became 25° C., then was heated at 70° C. for 6 h. After cooling to room temperature, the mixture was poured into water (100 mL), the aqueous phase was extracted with CH₂Cl₂ (2×20 mL); the organic phase was washed with water (20 mL) until the pH of washing solution became neutral, then with brine (3×20 mL), dried (MgSO₄) and concentrated under reduced pressure yielding an oil which was purified by silicagel (100-200 mesh) column chromatography using diethyl ether as the eluent. The pure product is obtained as a light yellow oil.

Yield: 58%. ¹HNMR (CDCl₃): δ 1.58-2.04 (m, 8H, 4CH₂ cyclopent.), 2.53-2.61 (m, 1H, H$_A$ of CH₂ epox.), 2.83-2.94 (m, 1H, H$_B$ of CH₂ epox.), 3.36-3.48 (m, 1H, CHO epox.), 4.13-4.28 and 4.52-4.65 (m, 2H, CH₂N pyraz), 4.93-5.03 (m, 1H, OCH cyclopent.), 6.56 (d, J=2.4 Hz, 1H, H-4 pyraz.), 6.58 (t, J=75.6, 1H, OCHF₂), 7.19 (d, J=8.0 Hz, 1H, H-5 Ar), 7.29 (dd, J=8.0, 2.0 Hz, 1H, H-6 Ar), 7.48 (d, J=2.0 Hz, 1H, H-2 Ar), 7.53 (d, J=2.4 Hz, 1H, H-5 pyraz.). Anal. (C₁₈H₂₀N₂O₃F₂) C, H, N. (% calculated/found) C: 61.71/61.86; H: 5.75/5.99; N: 8.00/8.07.

1-{3-[3-(cyclopentyloxy)-4-(difluoromethoxy)phenyl]-1H-pyrazol-1-yl}-3-morpholin-4-ylpropan-2-ol XXIIa

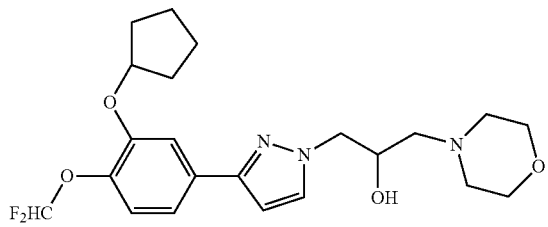 [SMILES: OC(CN1CCOCC1)Cn1ccc(-c2ccc(OC(F)F)c(OC3CCCC3)c2)n1]

To 3-[3-(cyclopentyloxy)-4-(difluoromethoxy)phenyl]-1-(oxiran-2-ylmethyl)-1H-pyrazole (0.37 g, 1.06 mmol) an excess of morpholine (1 mL) was added and the mixture was heated at 50-60° C. for 18 h. After cooling to room temperature, the mixture was diluted with diethyl ether (20 mL), then the organic phase was washed with water (20 mL), dried (MgSO₄) and concentrated under reduced pressure. The crude was purified by Silicagel column chromatography using as the eluent firstly diethyl ether, then a mixture of CH₂Cl₂/CH₃OH 9:1 to afford a pure product as light yellow oil.

Yield: 56%. ¹H-NMR (CDCl₃): δ 1.60-2.07 (m, 8H, 4CH₂ cyclopent.), 2.44-2.84, 3.63-3.93 (2m, 10H, 4CH₂ morph.+CH₂N), 4.13-4.40 (m, 3H, CH₂N pyraz.+C_H—OH), 4.82-4.92 (m, 1H, OCH cyclopent), 6.54 (d, J=2.4, 1H, H-4 pyraz.), 6.58 (t, J=75.6 Hz, 1H, OCHF₂), 7.18 (d, J=8.0 Hz, 1H, H-5 Ar), 7.28 (d, J=8.0 Hz, 1H, H-6 Ar), 7.44 (s, 1H, H-2 Ar), 7.56 (d, J=2.4, 1H, H-5 pyraz.). Anal. (C₂₂H₂₉N₃O₄F₂) C, H, N. (% calculated/found) C: 60.40/60.40; H: 6.68/6.81; N: 9.61/9.24.

1-(3-{3-[3-(cyclopentyloxy)-4-difluoromethoxyphenyl]-pyrazol-1-yl}-2-hydroxy-propyl)-piperidin-4-ol XXIIc

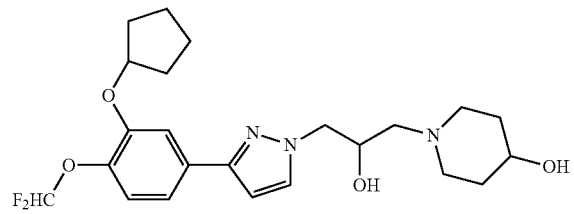

To 3-[3-(cyclopentyloxy)-4-(difluoromethoxy)phenyl]-1-(oxiran-2-ylmethyl)-1H-pyrazole (0.37 g, 1.06 mmol) solved in an. DMF (2 mL) piperidin-4-ol (202 mg, 2 mmol)) was added and the mixture was heated at 50-60° C. for 18 h. After cooling to room temperature, the mixture was diluted with diethyl ether (20 mL), then the organic phase was washed with water (20 mL), dried (MgSO₄) and concentrated under reduced pressure. The crude was purified by Silicagel column chromatography using diethyl ether, then a mixture of CH₂Cl₂/CH₃OH (8:2), as the eluent to afford a pure product as light yellow oil.

Yield: 55%. ¹H-NMR (CDCl₃): δ 1.20-2.00 (m, 8H, 4CH₂ cyclopent.), 2.10-2.30 (m, 1H, OH, which disappears with D₂O), 2.31-2.44 (2 m, 3H, C_HOH pip+CH₂N), 2.62-2.98 (m, 4H, 2CH₂), 3.55-4.31 (m, 4H, 2CH₂N pip.) 4.01-4.32 (m, 3H, CH₂N pyraz.+C_HOH), 4.80-5.00 (m, 1H, OCH cyclopent), 6.48 (d, J=2.2, 1H, H-4 pyraz.), 6.56 (t, J=74.0 Hz, 1H, OCHF₂), 7.13 (d, J=8.1 Hz, 1H, H-5 Ar), 7.27 (d, J=8.1 Hz, 1H, H-6 Ar), 7.41 (s, 1H, H-2 Ar), 7.53 (d, J=2.2, 1H, H-5 pyraz.). IR (CHCl₃) cm⁻¹: 3600-3000 (OH). Anal. (C₂₃H₃₁N₃O₄F₂) C, H, N. (% calculated/found) C: 61.18/61.00; H: 6.92/6.08; N: 9.31/9.22.

Synthesis of 3-[3-(cyclopentyloxy)-4-methoxyphenyl]-1-(triisopropylsilyl)-1H-pyrrole

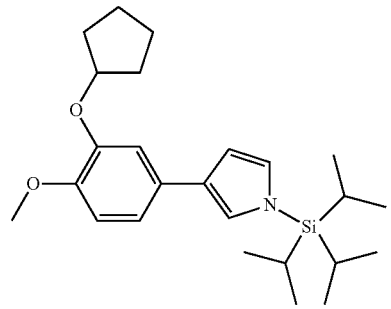 [SMILES: COc1ccc(-c2ccn([Si](C(C)C)(C(C)C)C(C)C)c2)cc1OC1CCCC1]

To a solution of 1-(triisopropylsilyl)-1H-pyrrol-3-ylboronic acid (0.25 g, 0.94 mmol) and 4-bromo-2-(cyclopentyloxy)-1-methoxybenzene (0.26 g, 0.94 mmol) in a mixture of toluene/methanol (1:1) (1 mL), a 2 M sodium carbonate solution (50 µL) was added. The resulting mixture was stirred under nitrogen atmosphere and then TETRAKIS (0.01 g, 0.01 mmol) was added. The reaction was stirred at 80° C. for 4 hs. After cooling at room temperature the mixture was diluted with ethylacetate (10 mL) and filtered on celite to remove inorganic palladium residues. The organic phase was evaporated in vacuo and solved in DCM (15 mL), washed with water (3×7.5 mL), dried (MgSO$_4$), and concentrated under reduced pressure to give an oil that was further purified by silicagel column chromatography, using a mixture of diethyl ether/petroleum ether (b.p. 40-60° C.) (1:1) as eluent, obtaining the product as a colourless oil.

Yield: 44%. $^1$H-NMR (CDCl$_3$): δ 0.96-1.23 (m, 18H, 6CH$_3$ isoprop.), 1.37-2.06 (m, 11H, 4CH$_2$ cyclopent.+3CH isoprop.), 3.88 (s, 3H, OCH$_3$), 4.82-4.96 (m, 1H, OCH cyclopent.), 6.57 (d, J=1.2 Hz, 1H, H$_2$' pyrrole), 6.79-6.93 (m, 2H, H$_3$'+H$_5$' pyrrole), 6.95-7.17 (m, 3H, H$_2$+H$_5$+H$_6$ Ar). IR (CHCl$_3$) cm$^{-1}$: 1507 (C—N). Anal. (C$_{25}$H$_{39}$NO$_2$Si) C, H, N. (% calculated/found) C: 72.59/72.82; H: 9.50/9.22; N 3.39/3.21.

Synthesis of 3-[3-(cyclopentyloxy)-4-methoxyphenyl]acrylic acid

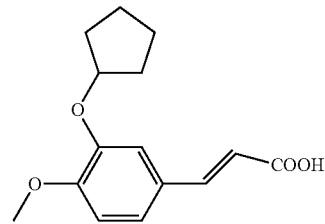 [SMILES: COc1ccc(/C=C/C(=O)O)cc1OC1CCCC1]

To a suspension of 3-(cyclopentyloxy)-4-methoxybenzaldehyde (0.44 g, 2 mmol) and malonic acid (0.83 g, 8 mmol) in toluene (10 mL), triethylamine (1.01 g, 10 mmol) and dimethylformamidedimethylacetal (DMFDMA) (0.36 g, 3 mmol) were added. The mixture was heated at reflux for 4 hs. The solvent was evaporated under reduced pressure and the crude was solved in dichloromethane (20 mL). The organic phase was extracted with NaHCO$_3$ saturated solution (2×10 mL) and then with a 1M NaOH solution (1×10 mL). The aqueous phases were acidified with 1N HCl solution and the obtained yellow solid was filtered and washed with water.

Yield: 90%. M.p.: 194-195° C.

Synthesis of ethyl 3-[3-(cyclopentyloxy)-4-methoxyphenyl]acrylate

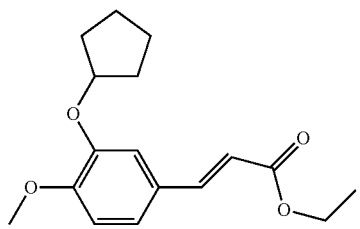 [SMILES: CCOC(=O)/C=C/c1ccc(OC)c(OC2CCCC2)c1]

To a solution of 3-[3-(cyclopentyloxy)-4-methoxyphenyl]acrylic acid (0.39 g, 1.5 mmol) in absolute ethanol (5 mL) concentrated sulphuric acid (0.1 mL) was added. The mixture was heated at reflux temperature for 4 hs. Ethanol was evaporated under reduced pressure and the obtained crude oil was dissolved in dichloromethane (20 mL), washed with NaHCO$_3$ saturated solution (2×10 mL), dried (MgSO$_4$), and concentrated under reduced pressure to obtain an oil that was used as crude in the next step.

Yield: 100%. IR (CHCl$_3$) cm$^{-1}$: 1700 (C=O). $^1$H-NMR (CDCl$_3$): δ 1.27 (t, J=7.2 Hz, 3H, CH$_3$), 1.43-2.02 (m, 8H, 4 CH$_2$ cyclopent.), 4.19 (q, J=7.2 Hz, 2H, CH$_2$), 4.65-4.83 (m, 1H, OCH cyclopent.), 6.24 (d, Jtrans=16 Hz, 1H, C̲H̲CO), 6.72-6.91 (m, 1H, H$_5$ Ar), 6.97-7.20 (m, 2H, H$_6$+H$_2$ Ar), 7.57 (d, Jtrans=16 Hz, 1H, C̲H̲=CHCO). Anal. (C$_{17}$H$_{22}$O$_4$) C, H, N. (% calculated/found) C: 74.68/74.51; H: 7.44/7.33.

Synthesis of ethyl 4-[3-(cyclopentyloxy)-4-methoxy-phenyl]-1H-pyrrole-3-carboxylate

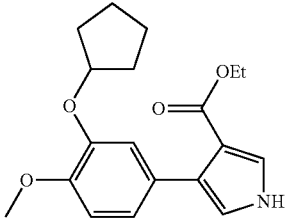 [SMILES: CCOC(=O)c1c[nH]cc1-c1ccc(OC)c(OC2CCCC2)c1]

To a suspension of sodium hydride (60% dispersion in mineral oil) (0.21 g, 5 mmol) in anhydrous diethylether (5 mL), under nitrogen atmosphere, a solution of ethyl 3-[3-(cyclopentyloxy)-4-methoxyphenyl]acrylate (0.58 g, 2 mmol) and p-toluenesulfonylmethyl isocyanide (0.42 g, 2 mmol) solved in anhydrous dimethylsulfoxide (2.5 mL) and anhydrous diethyl ether (5 mL) was added dropwise. The mixture was stirred at room temperature for 2 hs. Then the mixture was poured into water (20 mL) and extracted with ethyl acetate (3×10 mL). The organic phases were washed with brine (3×10 mL), dried (MgSO$_4$), and concentrated under reduced pressure to obtain an oil that was purified by silicagel column chromatography using dichloromethane as eluent to obtain an oil that crystallized with diethyl ether.

Yield: 46%. M.p.: 109-111° C. IR (CHCl$_3$) cm$^{-1}$: 3470 (NH), 1706 (C=O). $^1$H-NMR (CDCl$_3$): δ 1.29 (t, J=7.2 Hz, 3H, CH$_3$), 1.52-2.08 (m, 8H, 4CH$_2$ cyclopent.), 3.89 (s, 3H, OCH$_3$), 4.25 (q, J=7.2 Hz, 2H, CH$_2$), 4.78-4.90 (m, 1H, OCH cyclopent.), 6.77 (t, J=2.4 Hz, 1H, H$_2$' pyrrole), 6.82-7.18 (m, 3H, H$_2$+H$_5$+H$_6$ Ar), 7.50 (t, J=2.4 Hz, 1H, H$_5$' pyrrole), 8.62 (br s., 1H, NH which disappears with D$_2$O). Anal. (C$_{19}$H$_{23}$NO$_4$) C, H, N. (% calculated/found) C: 69.28/69.29; H: 7.04/7.56; N 4.25/4.00.

Synthesis of 4-[3-(cyclopentyloxy)-4-methoxy-phenyl]-1H-pyrrole-3 carboxylic acid

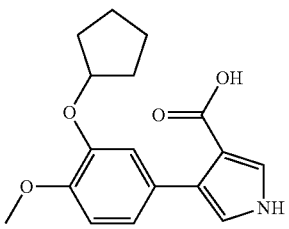

To a solution of ethyl 4-[3-(cyclopentyloxy)-4-methoxyphenyl]-1H-pyrrole-3-carboxylate (0.33 g, 1 mmol) in absolute ethanol (3 mL), 2 M NaOH solution (3 mL) was added. The mixture was heated at 120° C. for 4 hs. After cooling to room temperature, ethanol was evaporated under reduced pressure and the obtained solution was diluted with water (10 mL) and made acid with 6M HCl solution (2 mL), giving the desired compound as a grey solid.

Yield: 100% M.p.: 196-198° C. IR (CHCl$_3$) cm$^{-1}$: 3288 (OH), 1666 (C=O), $^1$H-NMR (CDCl$_3$): δ 1.50-2.08 (m, 8H, 4CH$_2$ cyclopent.), 3.89 (s, 3H, OCH$_3$), 4.75-4.90 (m, 1H, OCH cyclopent.), 6.78-7.20 (m, 5H, H$_2$'+H$_5$' pyrrole and H$_2$+H$_5$+H$_6$ Ar) 8.60 (br s, 1H, NH which disappears with D$_2$O). Anal. (C$_{17}$H$_{19}$NO$_4$) C, H, N. (% calculated/found) C: 67.76/67.71; 11:6.36/6.23; N 4.65/4.35.

Synthesis of 3-[3-(cyclopentyloxy)-4-methoxyphenyl]-1H-pyrrole (Method A)

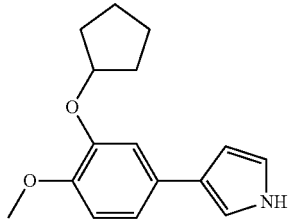 [SMILES: COc1ccc(-c2cc[nH]c2)cc1OC1CCCC1]

To a solution of 3-[3-(cyclopentyloxy)-4-methoxyphenyl]-1-(triisopropylsilyl)-1H-pyrrole (0.5 g, 1.21 mmol) in anhydrous THF (2 mL), 1 M solution of tetrabutylammonium fluoride (1.2 mL) was added dropwise. The reaction was stirred at room temperature for 5 min. THF was evaporated in vacuo and the residue was solved in diethyl ether (15 mL), washed with water (3×7.5 mL), dried (MgSO$_4$), and concentrated under reduced pressure to give an oil that crystallized from petroleum ether (b.p. 40-60° C.) as a yellow solid.

Yield: 48% m.p.: 117-120° C. IR (CHCl$_3$) cm$^{-1}$: 3482 (NH). $^1$H-NMR (CDCl$_3$): δ 1.52-2.08 (m, 8H, 4CH$_2$ cyclopent.), 3.90 (s, 3H, OCH$_3$), 4.78-4.96 (m, 1H, OCH cyclopent.), 6.51 (t, J=2.8 Hz, 1H, H$_2$' pyrrole), 6.80-6.96 (m, 2H, H$_3$'+H$_5$' pyrrole), 6.81-7.18 (m, 3H, H$_2$+H$_5$+H$_6$ Ar), 8.34 (brs., 1H, NH which disappears with D$_2$O). Anal. (C$_{16}$H$_{19}$NO$_2$) C, H, N. (% calculated/found) C: 74.68/74.51; H: 7.44/7.33; N 5.44/5.23.

(Method B)
4-[3-(cyclopentyloxy)-4-methoxyphenyl]-1H-pyrrole-3-carboxylic acid (0.3 g, 1 mmol) was heated at 200° C. until complete development of CO$_2$. Then the residue was dissolved in ethylacetate (15 mL). The organic phase was washed with 1 M NaOH (2×7.5 mL) and with water (2×7.5 mL), dried (MgSO$_4$), and concentrated under reduced pressure to obtain a crude oil that was purified by silicagel column chromatography using a mixture of petroleum ether (bp 40-60° C.) and diethylether (1:1) as the eluent, giving the desired product as a green solid.

Yield: 40%. M.p.: 115-120° C. IR (CHCl$_3$) cm$^{-1}$: 3482 (NH). $^1$H-NMR (CDCl$_3$): δ 1.52-2.08 (m, 8H, 4CH$_2$ cyclopent.), 3.90 (s, 3H, OCH$_3$), 4.78-4.96 (m, 1H, OCH cyclopent.), 6.51 (t, J=2.8 Hz, 1H, H$_2$' pyrrole), 6.80-6.96 (m, 2H, H$_3$'+H$_5$' pyrrole), 6.81-7.18 (m, 3H, H$_2$+H$_5$+H$_6$ Ar), 8.34 (br s., 1H, NH which disappears with D$_2$O). Anal. (C$_{16}$H$_{19}$NO$_2$) C, H, N. (% calculated/found) C: 74.68/74.51; H: 7.44/7.33; N 5.44/5.23.

Synthesis of 2-[3-(3-cyclopentyloxy-4-methoxyphenyl]-pyrrol-1-yl)-acetamide XXIIIa-c

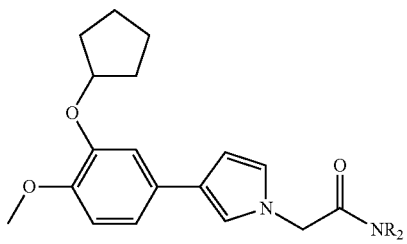

To a solution of 3-[3-(cyclopentyloxy)-4-methoxyphenyl]-1H-pyrrole (0.26 g, 1 mmol) in anhydrous DMF (2 mL) at 0° C., sodium hydride (60% dispersion in mineral oil) (100 mg, 2.5 mmol) was added. The mixture was stirred at 0° C. for 4 hs, then the suitable chloroacetamide was added (1 mmol) and the mixture was stirred at room temperature for 18 hs. The reaction mixture was poured into water (20 mL), extracted with ethyl acetate (3×10 mL) and washed with brine (3×10 mL), dried (MgSO$_4$), and concentrated under reduced pressure. Compound XXIIIa was crystallized by absolute ethanol, compound XXIIIb was crystallized by a mixture of petroleum ether/diethyl ether (bp 40-60° C.) (1:1), while compound XXIIIc was purified by silicagel column chromatography using diethyl ether, then a diethylether/methanol (9:1) mixture as eluent.

2-{3-[3-(cyclopentyloxy)-4-methoxy-phenyl]-pyrrol-1-yl}-1-morpholin-4-yl-ethanone XXIIIa

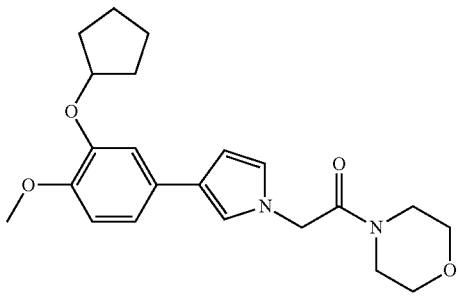 [SMILES: COc1ccc(-c2ccn(CC(=O)N3CCOCC3)c2)cc1OC1CCCC1]

White solid. Yield: 88%. M.p.: 169-171° C. IR (KBr) cm$^{-1}$ 1663 (CO). $^1$H-NMR (CDCl$_3$): δ 1.52-2.08 (m, 8H, 4CH$_2$ cyclopent.), 3.40-3.56 (m, 2H, 1CH$_2$N morph.), 3.57-3.79 (m, 6H, 1 CH$_2$N+2CH$_2$O morph.), 3.88 (s, 3H, OCH$_3$), 4.75 (s, 2H, CH$_2$C=O), 4.80-4.94 (m, 1H, OCH cyclopent.), 6.47 (d, J=2.6 Hz, 1H, H$_5$' pyrrole), 6.69 (d, J=2.8 Hz, 1H, H$_4$' pyrrole), 6.80-6.98 (m, 2H, H$_2$' pyrrole+H$_2$ Ar), 7.00-7.15 (m, 2H, H$_5$+H$_6$ Ar). Anal. (C$_{22}$H$_{28}$N$_2$O$_4$) C, H, N. (% calculated/found) C: 68.73/68.96; H: 7.34/7.61; N 7.29/6.99.

2-{3-[3-(Cyclopentyloxy)-4-methoxy-phenyl]-pyrrol-1-yl}-1-(2,6-dimethyl-morpholin-4-yl)-ethanone XXIIIb

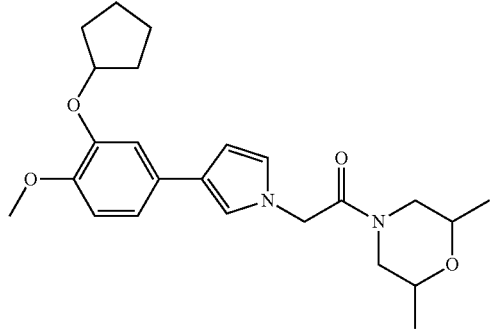

Grey solid. Yield: 61%. M.p.: 108-112° C. IR (KBr) cm$^{-1}$ 1660 (CO). $^1$H-NMR (CDCl$_3$): δ 0.92-1.33 (m, 6H, 2CH$_3$ morph.), 1.42-2.08 (m, 8H, 4CH$_2$ cyclopent.), 2.32-2.52 (m, 1H, CH$_2$N morph.), 2.72-2.97 (m, 1H, CH$_2$N morph.), 3.35-3.62 (m, 2H, CH$_2$N morph.), 3.67-3.85 (m, 1H, OCH morph.), 3.88 (s, 3H, OCH$_3$), 4.32-4.55 (m, 1H, OCH morph.), 4.74 (s, 2H, CH$_2$C=O), 4.79-4.92 (m, 1H, OCH cyclopent.), 6.46 (d, J=2.6 Hz, 1H, H$_5$' pyrrole), 6.69 (d, J=2.8 Hz, 1H, H$_4$' pyrrole), 6.77-7.13 (m, 4H, H$_2$' pyrrole+H$_2$+H$_5$+H$_6$ Ar). Anal. (C$_{24}$H$_{32}$N$_2$O$_4$) C, H, N. (% calculated/found) C: 69.88/70.03; H, 7.82/8.12; N, 6.79/6.48.

2-{3-[3-(Cyclopentyloxy)-4-methoxy-phenyl]-pyrrol-1-yl}-1-(4-hydroxy-piperidin-1-yl)-ethanone XXIIIc

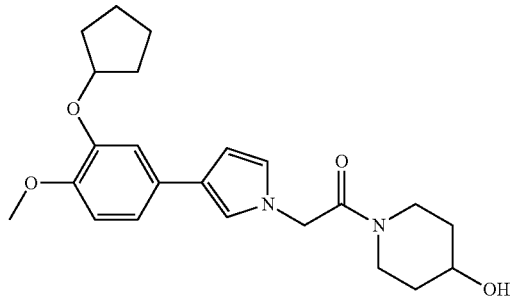 [SMILES: COc1ccc(-c2ccn(CC(=O)N3CCC(O)CC3)c2)cc1OC1CCCC1]

Yellow solid. Yield: 38%. M.p.: 156-158° C. IR (KBr) cm$^{-1}$ 3460 (OH), 1647 (CO). $^1$H-NMR (CDCl$_3$): δ 1.35-2.04 (m, 12H, 4CH$_2$ cyclopent.+2CH$_2$ pip.), 3.15-3.47 (m, 2H, CH$_2$N pip.), 3.87 (s, 3H, OCH$_3$), 3.89-4.18 (m, 3H, CH$_2$N+CH—OH pip.), 4.74 (s, 2H, CH$_2$C=O), 4.80-4.93 (m, 1H, OCH cyclopent.), 6.45 (d, J=2.5 Hz, 1H, H$_5$' pyrrole), 6.68 (d, J=2.6 Hz, 1H, H$_4$' pyrrole), 6.81-6.93 (m, 2H, H$_2$' pyrrole+H$_2$ Ar), 7.00-7.10 (m, 2H, H$_5$+H$_6$ Ar). Anal. (C$_{23}$H$_{30}$N$_2$O$_4$) C, H, N. (% calculated/found) C: 69.32/69.15; H: 7.59/7.63; N, 7.03/7.32.

Synthesis of 2-[3-(3-cyclopentyloxy-4-methoxyphenyl)-pyrrol-1-yl]-propionylamide XXIVa,c

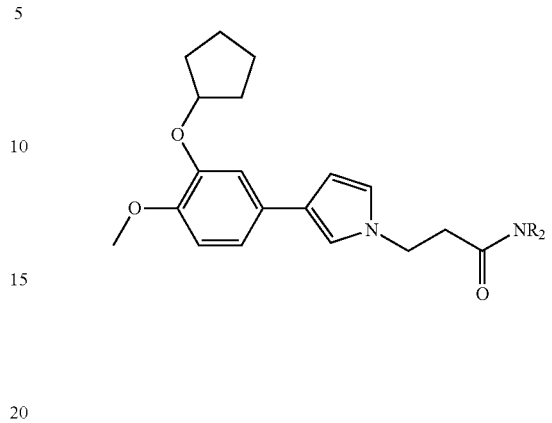

To a solution of 3-[3-(cyclopentyloxy)-4-methoxyphenyl]-1H-pyrrole (0.26 g, 1 mmol) in anhydrous dimethylformamide (2 mL) at 0° C. sodium hydride (60% dispersion in mineral oil) (100 mg, 2.5 mmol) was added. The mixture was stirred at 0° C. for 4 hs, then the suitable chloropropionylamide (1 mmol) was added and the mixture was stirred at room temperature for 18 hs. The reaction mixture was poured into water (20 mL), extracted with ethyl acetate (3×10 mL) and washed with brine (3×10 mL), dried (MgSO$_4$), and concentrated under reduced pressure. Compound XXIVa was crystallized by diethyl ether, while compound XXIVc was purified by silicagel column chromatography using diethylether, then a mixture of diethylether/methanol (9:1) as the eluent.

3-{3-[3-(cyclopentyloxy)-4-methoxy-phenyl]-pyrrol-1-yl}-1-morpholin-4-yl-propan-1-one XXIVa

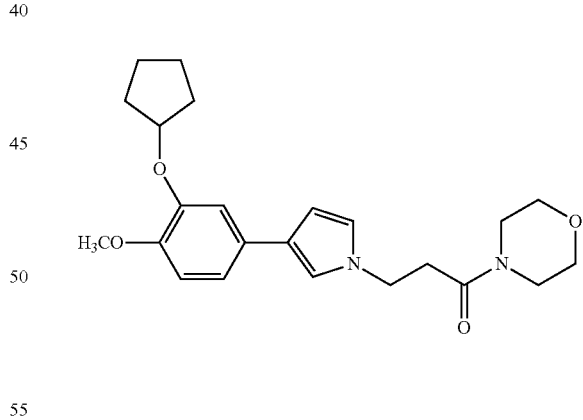

Yellow solid. Yield: 30%. M.p.: 110-112° C. IR (KBr) cm$^{-1}$ 1638 (CO). $^1$H-NMR (CDCl$_3$): δ 1.48-2.04 (m, 8H, 4CH$_2$ cyclopent.), 2.81 (t, J=6.8 Hz, 2H, CH$_2$C=O), 3.23-3.43 (m, 2H, CH$_2$N morph.), 3.50-3.78 (m, 6H, 2 CH$_2$O+CH$_2$N morph.), 3.87 (s, 3H, OCH$_3$), 4.31 (t, J=6.8 Hz, 2H, CH$_2$CH$_2$C=O), 4.79-4.94 (m, 1H, OCH cyclopent.), 6.40 (d, 0.1=2 Hz, 1H, H$_5$' pyrrole), 6.71 (d, J=2 Hz, 1H, H$_4$' pyrrole), 6.81-6.96 (m, 2H, H$_2$ Ar+H$_2$' pyrrole), 7.00-7.18 (m, 2H, H$_5$+H$_6$ Ar+H$_2$' pyrrole). Anal. (C$_{23}$H$_{30}$N$_2$O$_4$) C, H, N. (% calculated/found) C: 69.32/69.28; H: 7.59/7.96; N 7.03/6.63.

3-{3-[3-(Cyclopentyloxy)-4-methoxy-phenyl]-pyrrol-1-yl}-1-(4-hydroxy-piperidin-1-yl-propan-1-one XXIVc

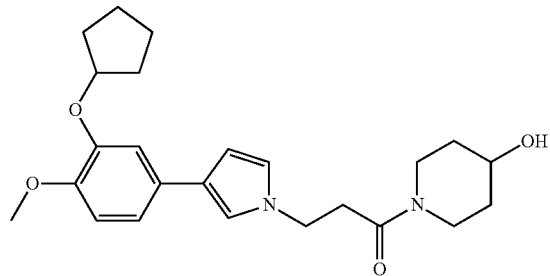 [SMILES: COc1ccc(-c2ccn(CCC(=O)N3CCC(O)CC3)c2)cc1OC1CCCC1]

White solid. Yield: 30%. M.p.: 110-112° C. IR (KBr) cm$^{-1}$ 3438 (OH), 1631 (CO). (CO). $^1$H-NMR (CDCl$_3$): δ 1.28-2.14 (m, 12H, 4CH$_2$ cyclopent.+2CH$_2$ pip.), 2.82 (t, J=8 Hz, 2H, CH$_2$C=O), 3.05-3.37 (m, 2H, CH$_2$N pip.), 3.50-3.72 (m, 1H, CH$_2$N pip.), 4.00-4.18 (m, 1H, CH$_2$N pip.), 3.87 (s, 3H, OCH$_3$), 4.30 (t, J=8 Hz, 2H, CH$_2$CH$_2$C=O), 4.80-4.95 (m, 1H, OCH cyclopent.), 6.40 (d, J=2 Hz, 1H, H$_5$ pyrrole), 6.72 (d, J=2 Hz, 1H, H$_4$' pyrrole), 6.80-6.98 (m, 2H, H$_2$Ar+H$_2$' pyrrole), 7.00-7.10 (m, 2H, H$_5$+H$_6$ pyrrole). Anal. (C$_{24}$H$_{32}$N$_2$O$_4$) C, H, N. (% calculated/found) C: 69.88/69.79; H: 7.82/8.21; N 6.79/6.99.

Synthesis of 3-[3-(cyclopentyloxy)-4-methoxy-phenyl]-1-oxiranylmethyl-1H-pyrrole

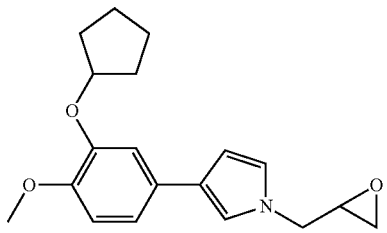 [SMILES: COc1ccc(-c2ccn(CC3CO3)c2)cc1OC1CCCC1]

To a solution of 3-[3-(cyclopentyloxy)-4-methoxyphenyl]-1H-pyrrole (0.75 g, 2.91 mmol) in anhydrous DMF (6 mL) at 0° C., sodium hydride (60% dispersion in mineral oil) (300 mg, 7.5 mmol) was added. The mixture was stirred at 0° C. for 4 hs, then epichlorohydrin (0.5 mL, 6.4 mmol) was added and the mixture was stirred at 50-60° C. for 18 hs. The reaction mixture was poured into water (30 mL), extracted with diethyl ether (3×10 mL) and washed with brine (3×10 mL), dried (MgSO$_4$), and concentrated under reduced pressure to obtain a crude oil that was purified by Silicagel column chromatography using diethylether as eluent. The desired product was obtained as a yellow oil.

Yield:71%. IR (CHCl$_3$) cm$^{-1}$: 1506 (C=O). H$^1$-NMR (CDCl$_3$): δ 1.47-2.04 (m, 8H, 4CH$_2$ cyclopent.), 2.50-2.58, 2.81-2.92 (2 m, 2H, CH$_2$O epox.), 3.23-3.35 (m, 1H, OCH epox.), 3.65-4.00 (m, 5H, OCH$_3$+CH$_2$N), 4.75-4.90 (m, 1H, OCH cyclopent.), 6.42 (d, J=1.6 Hz, 1H, H$_5$' pyrrole), 6.72 (d, J=1.8 Hz, 1H, H$_4$' pyrrole), 6.81-6.99 (m, 2H, H$_2$' pyrrole+H$_2$ Ar), 7.01-7.12 (m, 2H, H$_5$+H$_6$ Ar). Anal. (C$_{19}$H$_{23}$NO$_3$) C, H, N. (% calculated/found) C: 72.82/72.54; H: 7.40/7.50; N 4.47/4.72.

Synthesis of 1{3-[3-(cyclopentyloxy)-4-methoxy-phenyl]-pyrrol-1-yl}-3-morpholin-4-yl-propan-2-ol XXVa and 1-{3-[3-(cyclopentyloxy)-4-methoxy-phenyl]-pyrrol-1-yl}-3-(2,6-dimethyl-morpholin-4-yl)-propan-2-ol XXVb To 3-[3-(cyclopentyloxy)-4-methoxy-phenyl]-1-(oxiran-2-ylmethyl)-1H-pyrrole (0.44 g, 1.4 mmol) an excess of the suitable cycloamine (1 mL) was added. Then the mixture was stirred at 50-60° C. for 18 hs. After cooling to room temperature, the mixture was poured into water (30 mL), extracted with ethyl acetate (3×10 mL), washed with brine (3×10 mL), dried (MgSO$_4$), and concentrated under reduced pressure to obtain a crude oil that was purified by silicagel column chromatography using as the eluent firstly diethylether, then a mixture 9:1 of diethylether/methanol giving the desired products as yellow oils.

1-{3-[3-(Cyclopentyloxy)-4-methoxy-phenyl]-pyrrol-1-yl}-3-morpholin-4-yl-propan-2-ol XXVa

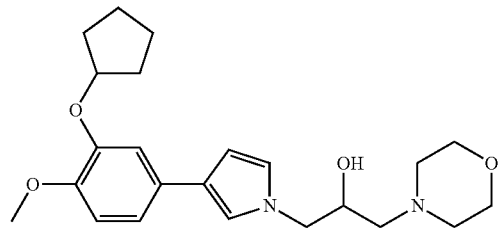 [SMILES: COc1ccc(-c2ccn(CC(O)CN3CCOCC3)c2)cc1OC1CCCC1]

Yellow oil. Yield: 46%. IR (CHCl$_3$) cm$^{-1}$: 3438 (OH). $^1$H-NMR (CDCl$_3$): δ 1.50-2.08 (m, 8H, 4CH$_2$ cyclopent.), 2.32-3.00 (m, 6H, 2CH$_2$N morph.+CH$_2$N chain), 3.02-3.38 (m, 2H, CH$_2$O morph.), 3.60-4.07 (m, 7H, CH$_2$O morph.+CH$_2$N pyrrole+OCH$_3$), 4.10-4.30 (m, 1H, CH—OH), 4.78-4.95 (m, 1H, OCH cyclopent.), 6.40 (s, 1H, H$_5$' pyrrole), 6.71 (s, 1H, H$_4$' pyrrole), 6.80-6.99 (m, 2H, H$_2$ Ar+H$_2$' pyrrole), 7.00-7.15 (m, 2H, H$_5$+H$_6$ pyrrole). Anal. (C$_{23}$H$_{32}$N$_2$O$_4$) C, H, N. (% calculated/found) C: 68.97/69.13; H: 8.05/8.27; N 6.99/6.66.

1-{3-[3-(Cyclopentyloxy)-4-methoxy-phenyl]-pyrrol-1-yl}-3-(2,6-dimethyl-morpholin-4-yl)-propan-2-ol XXVb

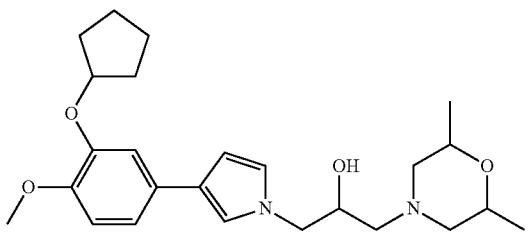

Yellow oil. Yield: 25%. IR (CHCl$_3$) cm$^{-1}$ 3437 (OH). $^1$H-NMR (CDCl$_3$): δ 0.99-1.28 (m, 6H, 2CH$_3$ morph.), 1.55-2.05 (m, 8H, 4CH$_2$ cyclopent.), 2.40 (d, J=5.8 Hz, 2H, CH$_2$N pyrrole), 2.60-3.18 (m, 2H, 2 CHO morph), 3.63-3.85 (m, 3H, CH$_2$N morph.+CHOH), 3.89 (s, 3H, OCH$_3$), 3.92-4.20 (m, 4H, CH$_2$N morph.+CH$_2$N chain), 4.79-4.93 (m, 1H, OCH cyclopent.), 6.41 (d, J=1.6 Hz, 1H, H$_5$' pyrrole), 6.72 (d, J=2.6 Hz, 1H, H$_4$' pyrrole), 6.82-6.99 (m, 2H, H$_2$' pyrrole+H$_2$ Ar), 7.02-7.15 (m, 2H, H$_5$+H$_6$ Ar). Anal. (C$_{25}$H$_{36}$N$_2$O$_4$) C, H, N. (% calculated/found) C: 70.06/69.97; H: 8.47/8.66; N 6.54/6.20.

Synthesis of 1-(3-{3-[3-(cyclopentyloxy)-4-methoxy-phenyl]-pyrrol-1-yl}-2-hydroxy-propyl)-piperidin-4-ol XXVc

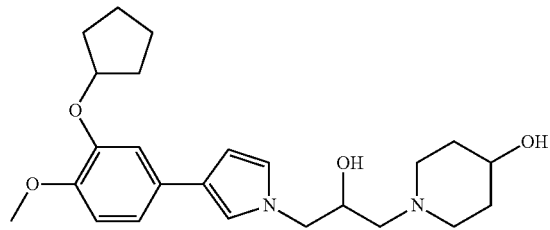 [SMILES: COc1ccc(-c2ccn(CC(O)CN3CCC(O)CC3)c2)cc1OC1CCCC1]

To a solution of 3-[3-(cyclopentyloxy)-4-methoxy-phenyl]-1-(oxiran-2-ylmethyl)-1H-pyrrole (0.44 g, 1.4 mmol) solved in anhydrous DMF (2 mL). 4-hydroxypiperidine (0.29 g, 2.8 mmol) was added at small portion. Then the mixture was stirred at 50-60° C. for 18 hs. After cooling to room temperature, the mixture was poured into water (30 mL), extracted with ethyl acetate (3×10 mL), washed with brine (3×10 mL), dried (MgSO$_4$), and concentrated under reduced pressure to obtain a crude oil that was purified by silicagel column chromatography using diethylether, then a mixture of diethylether/methanol (9:1) as the eluent giving the desired product as yellow oil.

Yield: 31%. IR (CHCl$_3$) cm$^{-1}$ 3358 (OH). $^1$H-NMR (CDCl$_3$): δ 1.45-2.08 (m, 12H, 4CH$_2$ cyclopent.+2CH$_2$ pip.), 2.21-2.67 (m, 4H, CH$_2$N pip.+2OH disappears with D$_2$O), 2.72-3.10 (m, 2H, CH$_2$N pip.), 3.20-3.40 (m, 2H, CH$_2$N chain), 3.72-4.00 (m, 6H, OCH$_3$+C̲H̲—OH pip.+CH$_2$N pyrr.), 4.02-4.20 (m, 1H, C̲H̲—OH chain), 4.78-4.93 (m, 1H, OCH cyclopent.), 6.39 (d, J=1.6 Hz, 1H, H$_5$' pyrrole), 6.71 (d, J=1.6 Hz, 1H, H$_4$' pyrrole), 6.80-6.99 (m, 2H, H$_2$' pyrrole+H$_2$ Ar), 7.01-7.17 (m, 2H, H$_5$+H$_6$ Ar).

Synthesis of 4-[3-(cyclopentyloxy)-4-methoxyphenyl]-1H-pyrrole-3-carboxylic acid amides XXVIa-c

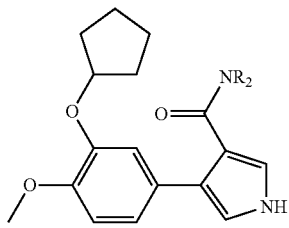

To a solution of 4-[3-(cyclopentyloxy)-4-methoxyphenyl]-1H-pyrrole-3-carboxylic acid (0.34 g, 1.13 mmol) in anhydrous dimethylformamide (3 mL) at 0° C., triethylamine (0.23 mL, 1.66 mmol), the suitable cycloamine (2.26 mmol) and diphenylphosphoryl azide (0.3 mL, 1.13 mmol) were slowly added. The mixture was heated at 70-80° C. for 18 hs. After coiling to room temperature, the mixture was poured into ice water (10 mL) and extracted with dichloromethane (3×5 mL). The organic phase was then washed with 1M NaOH (5 mL), with brine (2×5 mL), dried (MgSO$_4$) and concentrated under reduced pressure to obtain an oil that was purified by silicagel column chromatography using diethylether, then a diethylether/methanol mixture (9:1) as the eluent.

{4-[3-(Cyclopentyloxy)-4-methoxy-phenyl]-1H-pyrrol-3-yl}-morpholin-4-yl-methanone XXVIa

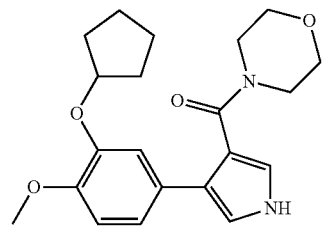 [SMILES: COc1ccc(-c2c[nH]cc2C(=O)N2CCOCC2)cc1OC1CCCC1]

Brown solid. Yield: 60%. M.p.: 126-128° C. IR (KBr) cm$^{-1}$: 3473 (NH), 1608 (CO). $^1$H-NMR (CDCl$_3$): δ 1.45-2.03 (m, 8H, 4CH$_2$ cyclopent.), 2.38-2.65 (m, 2H, 1CH$_2$N morph.), 3.02-3.80 (m, 6H, 1CH$_2$N+2CH$_2$O morph.), 3.89 (s, 3H, OCH$_3$), 4.66-4.88 (m, 1H, OCH cyclopent.), 6.72-6.95 (m, 4H, H$_2$+H$_5$+H$_6$ Ar+H$_2$' pyrrole), 6.98-7.07 (m, 1H, H$_5$' pyrrole), 9.22 (br s, 1H, NH which disappears with D$_2$O). Anal. (C$_{21}$H$_{26}$N$_2$O$_4$) C, H, N. (% calculated/found) C:68.09/68.48; H: 7.07/7.24; N 7.56/7.38.

{4-[3-(Cyclopentyloxy)-4-methoxy-phenyl]-1H-pyrrol-3-yl}-(2,6-dimethyl-morpholin-4-yl)-methanone XXVIb

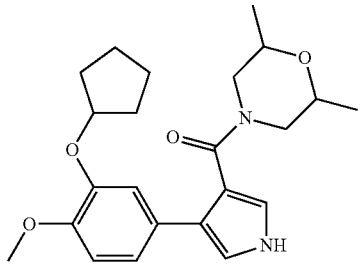

White solid. Yield: 49%. M.p.: 158-159° C. IR (KBr) cm$^{-1}$: 3171 (NH), 1592 (CO), $^1$H-NMR (CDCl$_3$): δ 0.88-1.35 (m, 6H, 2CH$_3$ morph.), 1.50-2.08 (m, 8H, 4CH$_2$cyclopent.), 2.08-2.50 (m, 4H, 2CH$_2$N morph.), 2.57-2.84 (m, 1H, OCH morph.), 3.88 (s, 3H, OCH$_3$), 4.24-4.61 (m, 1H, OCH morph.), 4.65-4.83 (m, 1H, OCH cyclopent.), 6.73-7.06 (m, 5H, H$_2$+H$_5$+H$_6$ Ar+H$_2$' and H$_5$' pyrrole), 9.32 (br s, 1H, NH which disappears with D$_2$O). Anal. (C$_{23}$H$_{30}$N$_2$O$_4$) C, H, N. (% calculated/found) C: 69.32/69.15; H: 7.59/8.00; N 7.03/6.70.

{4-[3-(Cyclopentyloxy)-4-methoxy-phenyl]-1H-pyrrol-3-yl}-(4-hydroxy-piperidin-1-yl)-methanone XXVIc

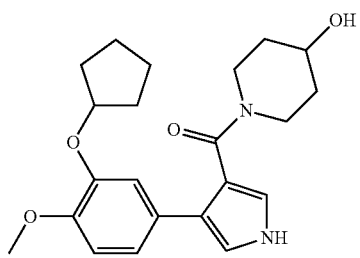 [SMILES: COc1ccc(-c2c[nH]cc2C(=O)N2CCC(O)CC2)cc1OC1CCCC1]

Grey solid. Yield: 20%. M.p.: 175-177° C. IR (KBr) cm$^{-1}$: 3521 (OH), 3176 (NH), 1606 (CO). $^1$H-NMR (CDCl$_3$): δ 1.50-2.40 (m, 12H, 4CH$_2$ cyclopent.+2CH$_2$ pip.), 3.00-3.21 (m, 2H, CH$_2$N pip.), 3.68-4.02 (m, 6H, OCH$_3$+CH$_2$N pip.+CH—OH pip.), 4.68-4.82 (m, 1H, OCH cyclopent.), 6.73-6.92 (m, 3H, H$_2$+H$_5$+H$_6$ Ar), 7.19-7.32 (m, 2H, H$_2$'+H$_5$' pyrrole), 9.79 (br s, 1H, NH which disappears with D$_2$O). Anal. (C$_{22}$H$_{28}$N$_2$O$_4$) C, H, N. (% calculated/found) C:68.73/68.40; H: 7.34/7.33; N 7.29/7.07.

Biological Methods

The activity of the compounds according to the present invention towards was evaluated following methods described in the literature (O. Bruno et al, *J. Med Chem*, 2009; O. Bruno et al *Br. J. Pharmacol*, 2011).

A summary of such methods is given hereinafter.

PDE4 Enzyme Inhibition

Compound's evaluation on PDE4D3, PDE4A4, PDE4B2 and PDE4C2 enzyme assays were performed by Scottish Biomedical (Glasgow, Scotland, UK) using recombinant human PDE enzymes expressed in a baculoviral system. The preliminary screening assays were performed by the IMAP technology (Molecular Devices), which is based on the high affinity binding of phosphate by immobilized metal coordination complexes on nanoparticles. The binding reagent complexes with phosphate groups on nucleotide monophosphate generated from cyclic nucleotides (cAMP) through phosphodiesterases. With fluorescence polarization detection, binding causes a change in the rate of the molecular motion of the phosphate bearing molecule and results in an increase in the fluorescence polarization value observed for the fluorescent label attached to the substrate. In all the experiments, rolipram as reference compound was tested at nine concentrations in duplicate to obtain an inhibition curve in order to validate this experiment. All compounds were solved in DMSO at 10$^{-2}$ M concentration and then diluted with water to the final suitable concentrations. All synthesized compounds were tested preliminary on PDE4D3 at 10$^{-5}$ M concentration, in duplicate. Results are expressed as a percent inhibition of control activity (see table 1). Results showing an inhibition of the control higher than 50% are considered to represent significant effects of the test compounds. 50% is the most common cutoff value for further investigation (determination of IC$_{50}$ value from concentration-response curves).

Compounds showing inhibition control higher than 50% on PDE4D3 were further tested on the same isoform enzyme at five concentrations in the interval 10$^{-8}$-10$^{-4}$ M. IC$_{50}$ values for rolipram and tested compounds were determined by nonlinear regression analysis of its inhibition curve, using Hill equation curve fitting (Graph Pad Prism software). The IC$_{50}$ values obtained for the reference compounds are within accepted limits of historic averages obtained (0.5 log unit). IC$_{50}$ values are reported at μM concentration in table 1. Then, the most active compounds have been tested on PDE4A4, PDE4B2 and PDE4C2 (being the most representative among the numerous splicing variants of each PDE4 isoform) to obtain more information about their isoform selectivity. The results are reported (as percent of inhibition at 10 μM concentration) in Table 1.

In Vitro Genotoxic and Cytotoxic Evaluation

To evaluate the preliminary toxic profile of the molecule XVIIIa, we performed cytotoxicity and genotoxicity assays on human neuronal cells (HTLA). For the cytotoxic potential, we analyzed the lactate-dehydrogenase release in cells exposed for 24 hours to high concentrations (100 μM) of XVIIIa or GEBR-7b (lead compound—Bruno et al, *Br. J. Pharm.*, 2011, 164:2054).

To evaluate the genotoxic potential of XVIIIa and GEBR-7b, we analyzed the phosphorylation of the chromatin-bound histone H2AX (γ-H2AX), which is a quantitative marker for the DNA damage response at the site of double-strand breaks. As a positive control, we used etoposide, a topoisomerase II inhibitor that induces DNA double-stranded breaks.

In Vitro cAMP-Enhancing Potential

To analyze the capability of GEBR-7b and XVIIIa of enhancing the intracellular accumulation of cAMP, we used a specific enzyme immunoassay (EIA) to quantify the levels of cAMP in neuronal cultured cells exposed to the PDE4D inhibitors.

In Vivo cAMP-Enhancing Potential

The in vivo effects of XVIIIa on extracellular cAMP levels in the hippocampus of freely moving rats were analyzed by means of intracerebral microdialysis.

Electrophysiological Studies

Compound XVIIIa was tested to determine whether PDE4D inhibition can revert the damage of synaptic function following Aβ elevation in Tg2576 mice.

All experiments were performed with approval of the Columbia University IACUC Committe. The animals were 12 month old single transgenic mice expressing the human APP mutation (K670N,M671L) (a.k.a. Tg2576), as well as their WT littermates.

Slice recordings were performed as described previously (Trinchese et al, *Ann Neurol* 2004). Briefly, 400-μm slices were cut with a tissue chopper and maintained in an interface chamber at 29° C. for 90 minutes prior to recording. CA1 fEPSPs were recorded by placing both the stimulating and the recording electrodes in CA1 stratum radiatum. Basal synaptic transmission was assayed either by plotting the stimulus voltages against slopes of fEPSP. For LTP experiments, a 10-minute baseline was recorded every minute at an intensity that evokes a response approximately 35% of the maximum evoked response. Baseline was followed by a 20 minute perfusion with the compound prior to eliciting LTP using θ-burst stimulation (4 pulses at 100 Hz, with the bursts repeated at 5 Hz, and each tetanus including 3 ten-burst trains separated by 15 seconds).

Biological Results

The tests carried out on compounds according to the present invention provided the following results.

TABLE 1

Activity on different PDE4 isoforms expressed as % of inhibition at 10 μM concentration and IC$_{50}$ values (μM)

| | PDE4D1 % inib at 10 μM | PDE4D2 % inib at 10 μM | PDE4D3 % inib at 10 μM (IC$_{50}$ μM) | PDE4A4 % inib at 10 μM (IC$_{50}$ μM) | PDE4B2 % inib at 10 μM (IC$_{50}$ μM) | PDE4C2 % inib at 10 μM |
|---|---|---|---|---|---|---|
| XIIIa | nt | nt | 21 | nt | nt | nt |
| XIIIb | nt | nt | 29 | nt | nt | nt |
| XIIIc | nt | nt | 26 | nt | nt | nt |
| XIIId | nt | nt | 15 | nt | nt | nt |
| XIIIe | nt | nt | 8 | nt | nt | nt |
| XIIIf | nt | nt | 33 | nt | nt | nt |
| XIVa | nt | nt | 29 | nt | nt | nt |
| XIVb | nt | nt | 51 (5.58) | 45 | 27 | 23 |
| XIVc | nt | nt | 30 | nt | nt | nt |
| XIVd | nt | nt | 57 (1.22) | 66 | 59 | 47 |
| XIVe | nt | nt | 40 | nt | nt | nt |
| XIVf | nt | nt | 23 | nt | nt | nt |
| XIVg | nt | nt | 65 (1.11) | 69 | 68 | 40 |
| XVa | nt | nt | 39 | nt | nt | nt |
| XVb | nt | nt | 13 | nt | nt | nt |
| XVIa | nt | nt | 38 | nt | nt | nt |
| XVIb | 2 | 3 | 15 | 0 | 5 | 7 |
| XVIIa | nt | nt | 41 | nt | nt | nt |
| XVIIb | nt | nt | 35 | nt | nt | nt |
| XVIIIa | 34 | 28 | 68 (7.6) | 22 | 18 | 11 |
| XVIIIb | 77 | 75 | 78 (6) | 52 (0.12) | 53.0 (0.46) | 45 |
| XVIIIc | nt | nt | 2 | nt | nt | nt |
| XIX | nt | nt | nt | nt | nt | nt |
| XXa | 42 | 23 | 27 | nt | nt | nt |
| XXb | 18 | 13 | 23 | nt | nt | nt |
| XXIa | nt | nt | 42 | nt | nt | 10 |
| XXIb | nt | nt | 53 (1.8) | 28 | 28 | 42 |
| XXIIa | nt | nt | 64 (2.43) | 11 | 26 | nt |
| XIIc | nt | nt | 73 | nt | nt | nt |
| XXIIIa | nt | nt | 7 | nt | nt | nt |
| XXIIIb | nt | nt | 13 | nt | nt | nt |
| XXIIIc | nt | nt | 9 | nt | nt | nt |
| XXIVa | nt | nt | 44 | nt | nt | nt |
| XXIVc | nt | nt | 29 | nt | nt | nt |
| XXVa | nt | nt | 21 | nt | nt | nt |
| XXVb | nt | nt | 36 | nt | nt | nt |
| XXVc | nt | nt | 5 | nt | nt | nt |
| XXVIa | nt | nt | 13 | nt | nt | nt |
| XXVIb | nt | nt | 6 | nt | nt | nt |
| XXVIc | nt | nt | 15 | nt | nt | nt |

The results of the lactate-dehydrogenase test clearly indicate that, at least under the tested conditions, none of XVIIIa, XXIIa and GEBR-7b (our lead used as reference compound) exerted cytotoxic effects as reported in the table 2.

TABLE 2

| Tested compound | % cytotoxicity |
|---|---|
| Positive Control | 100 ± 8.0 |
| XVIIIa | 3.3 ± 0.4 |
| XXIIa | 0.1 ± 0.36 |
| GEBR-7b | 0.7 ± 0.09 |

As concerns genotoxicity, the etoposide treatment of HTLA cells led to a rapid and robust DNA damage, which was not observed by exposing the cells to XVIIIa, XXIIa or GEBR-7b, as shown in FIG. 1, which is a Western blot analysis of γ-H2AX in HTLA cells treated for the indicated time periods with 100 μM etoposide, GEBR-7b, XVIIIa, XXIIa or an equal volume of solvent (DMSO). The H2AX signal represents the internal loading control. The figure is representative of three independent experiments all showing essentially similar results.

Figure 2:
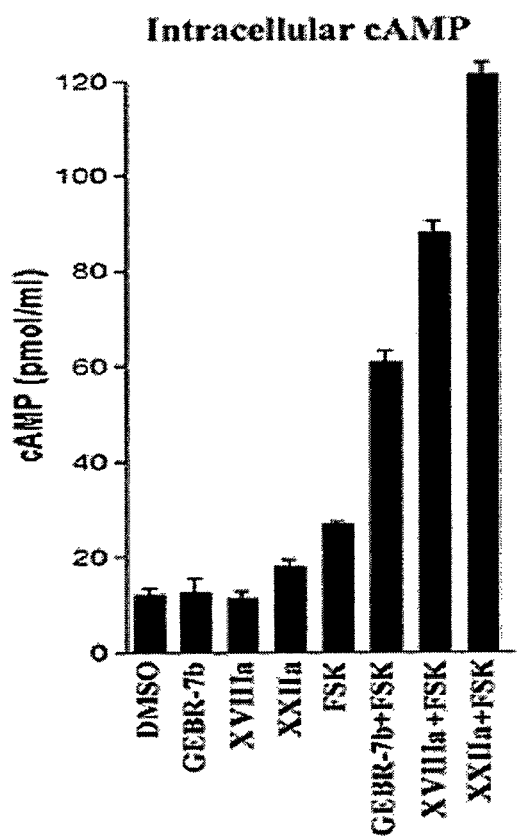
FIG. 2 is a histogram showing the effect of compounds GEBR-7b, XVIIIa and XXIIa on the accumulation of the forskolin (FSK)-induced cAMP in neuronal cultured cells.

In addition, GEBR-7b, XVIIIa and XXIIa significantly increased (2, 3 and 4.5 fold induction, respectively) the accumulation of the forskolin (FSK)-induced cAMP, without affecting the basal cAMP levels, as reported in FIG. 2, which represents a quantification of intracellular cAMP by specific enzyme immunoassay (EIA). Neuronal cultured cells were pre-treated for 10 min with XVIIIa (100 μM), XXIIa (100 μM), GEBR-7b (100 μM) or an equal volume of DMSO, Then, 1 μM forskolin (FSK) was added, where indicated, for 20 min. At the end of the incubation periods, intracellular cAMP was measured with a cAMP-specific EIA kit, according to the manufacturer's instructions. The histogram shows the mean±S.D. for three independent experiments.

Local administration of 30 μM XVIIIa by reverse dialysis caused a slight, though not significant, increase of hippocampal extracellular cAMP. However, when the PDE4D inhibitor was infused at the concentration of 100 μM, a marked cAMP response could be observed (40-80% over basal values) as reported in FIG. 3. The effects of XVIIIa were similar to those previously reported for the PDE4D inhibitor GEBR-7b (lead compound; data taken from Bruno et al., Br. J. Pharmacol. 2011, 164, 2054-2063).

Figure 3:
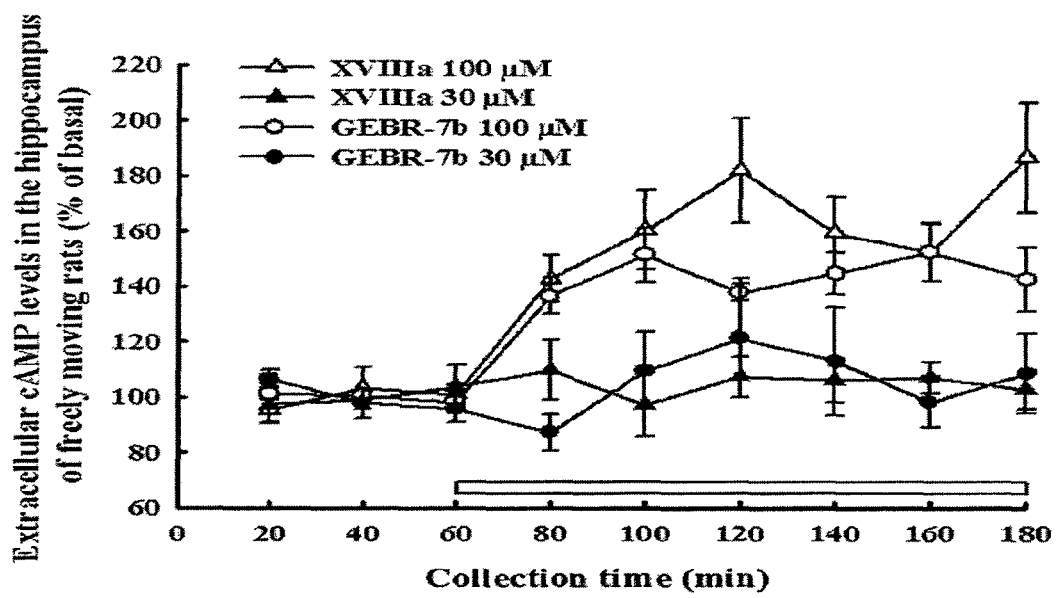
FIG. 3 is a diagram showing the effects of the PDE4D inhibitors XVIIIa and GEBR-7b on extracellular cAMP in the hippocampus of freely moving rats.

FIG. 3 shows the effects of PDE4D inhibitors on extracellular cAMP in the hippocampus of freely moving rats. XVIIIa or GEBR-7b were administered through the probe after 3 consecutive control samples had been collected and were present in the infusion fluid for the time indicated by the horizontal empty bar. Data are expressed as percentages of the mean basal value (defined 100%) that was determined by averaging the cAMP content in the three fractions collected before drug treatment. Each point represents the mean±SEM for 3-6 different experiments.

Figure 4:
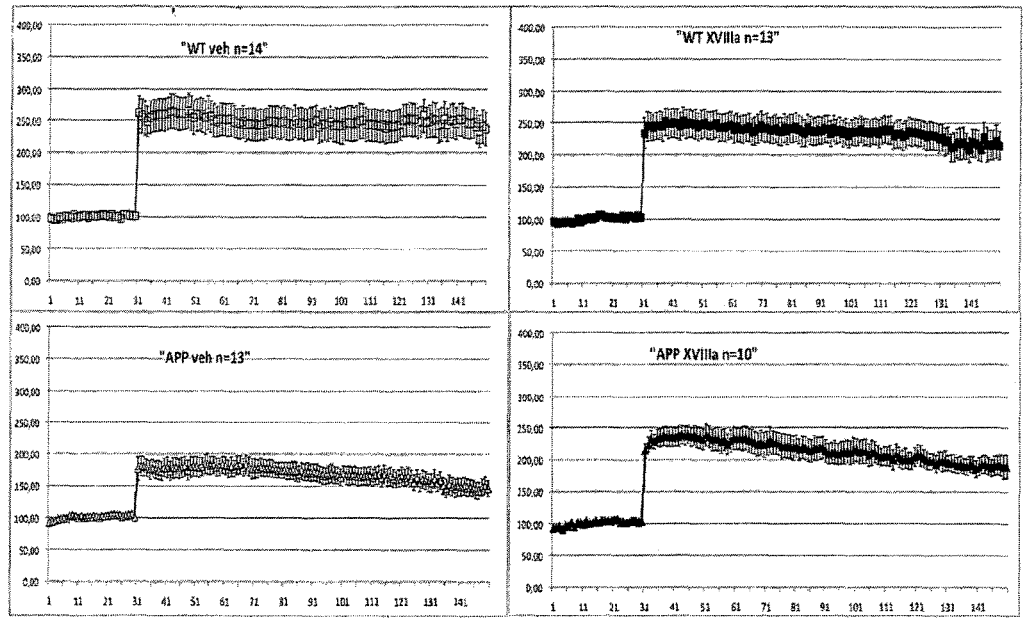
FIGS. 4 and 5 are diagrams representing the results of an electrophysiological study on Tg2576 mice.
Figure 5:
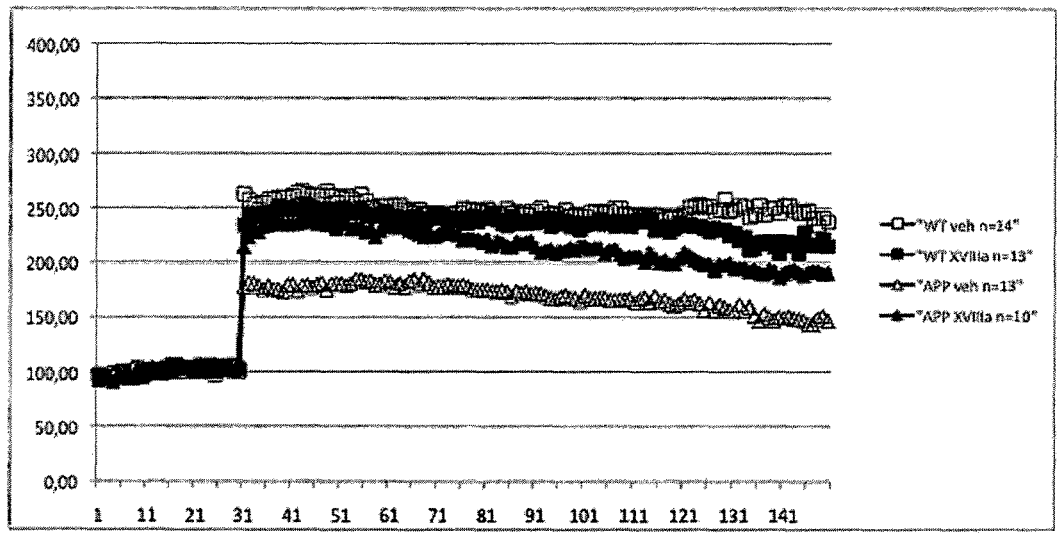

In the electrophysiological study on Tg2576 mice we confirmed that hippocampal slices from these animals show impairment of CA3-CA1 long term potentiation (LTP) at the age of 12 months when plaques are present (Trinchese F. et al, *Ann. Neurol.* 2004, 55, 801). Most importantly, we found that XVIIIa (2 μM, administered through the bath solution for 20 minutes before inducing LTP through theta burst stimulation) rescued the defect in LTP of hippocampal slices from 12 month-old Tg mice (two way ANOVA: p<0.05 comparing compound treated Tg slices vs. vehicle-treated Tg slices) without affecting LTP in WT littermates as reported in FIGS. 4 and 5 (FIG. 5 is a cumulative diagram wherein the four curves of FIG. 4 are reported together, while omitting, for the sake of clarity, the SD confidence intervals).

Figure 6:
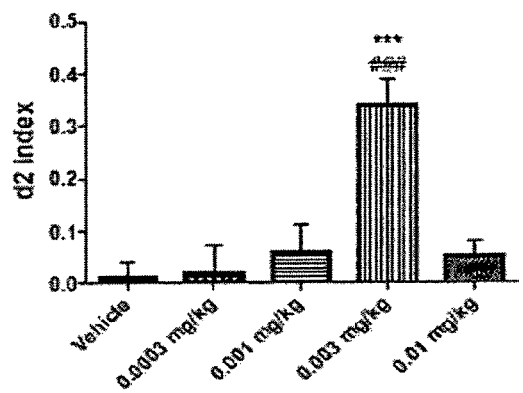
FIG. 6 is a diagram showing the results of an OLT dose-response experiment with XXIIa, which reflect the effects of different doses of XXIIa on spatial object memory performance.

The results of an OLT dose-response experiment, which is a spatial variant of ORT (Object recognition test) previously assessed by one of the applicant (Rutten et al., *Neuropsychopharmacology*, 2009, 34:1914), with XXIIa are summarized in Table 3 and FIG. 6. A one-way ANOVA revealed no significant differences between treatment conditions in the level of exploration in T1 (e1: $F_{4,109}$=1.038 n.s.). For T2 a significant difference was found (e2: $F_{4,109}$=5.120; P=0.001) and Post-hoc Bonferroni tests showed a difference between 0.003 mg/kg and vehicle/0.0003 mg/kg XXIIa. Implying that the active dose showed significantly more exploration behavior than vehicle and the lowest dose.

TABLE 3

Mean values (±SEM) of the different OLT measures

| Dose | e1 (s) | e2 (s) | d2 | N |
|---|---|---|---|---|
| vehicle | 31.90 (2.58) | 21.45 (1.62) | 0.01 (0.03) | 23 |
| 0.0003 mg/kg | 28.51 (3.13) | 25.91 (2.73) | 0.02 (0.05) | 22 |
| 0.001 mg/kg | 33.78 (2.82) | 29.07 (2.30) | 0.06 (0.05) | 24 |
| 0.003 mg/kg | 37.85 (4.62) | 35.82 (2.82) | 0.34 (0.05) ### | 23 |
| 0.01 mg/kg | 34.24 (3.12) | 30.32 (2.14) | 0.05 (0.03) | 22 |

Displayed are the mean exploration in T1 (e1) and T2 (e2) and discrimination performance (d2) of the different treatment conditions in the XXIIa dose-response study. The Standard Error of the Mean (SEM) is presented between brackets. One sample t-tests were performed on the d2 measures. A significant difference from zero (indicated by hash-signs; ### p < 0.001) indicates that the animals remembered the location of the object from T1.

One-sample t-test comparing the d2 index of every condition to zero showed that vehicle, 0.0003, 0.001 and 0.01 mg/kg XXIIa did not significantly differ from zero, implying no recognition of the moved object after a 24 h interval. 0.003 mg/kg XXIIa showed a significant difference compared to zero (P<0.0001). A one-way ANOVA comparing the d2 index of the condition was significant ($F_{4,109}$=9.345; P<0.001) and Dunnett's t-test comparing the conditions to vehicle showed that only 0.003 mg/kg XXIIa differs significantly from vehicle (P<0.001). These data indicated that XXIIa was able to fully enhance memory function at a dose of 0.003 mg/kg, whereas animals treated with 0.0003, 0.001 and 0.01 mg/kg did not show any memory improvement at all i.e. no difference from zero or vehicle. The effects of the different doses of XXIIa on spatial object memory performance are graphically presented in FIG. 6.

The results of the spatial working memory test, assessed by using the Y-maze spontaneous alternation task as previously described (Sierksma A. S., *Neurobiol. Aging*, 2013, 34:319) on XXIIa are summarized in Table 4. Working memory function is given by the percentage of alternations made while exploring the y-maze for 6 min. No animals were excluded from the statistical analysis.

TABLE 4

Mean alternations (+SEM) in the Y-maze continuous alternation task

| Condition | Alternations % | SEM | n |
|---|---|---|---|
| Vehicle | 60.36 ### | 2.03 | 16 |
| 0.001 mg/kg | 60.86 ### | 2.12 | 16 |
| 0.003 mg/kg | 63.54 ### | 1.53 | 16 |
| 0.01 mg/kg | 61.88 ### | 1.83 | 16 |

Displayed are the mean percentage of alternations and their SEM's of every condition in the y-maze alternation task. One sample t-tests were performed comparing the percentage of alternations to chance level (50%), a significant difference from 50% (indicated by hash-signs; ### p < 0.001) indicates that the animals have functioning working memory.

Figure 7:
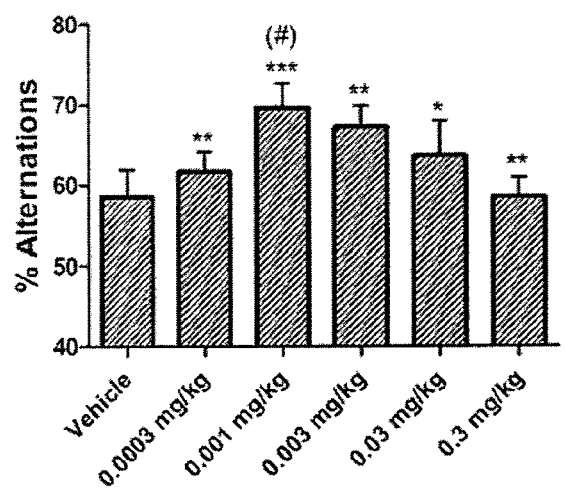
FIG. 7 is a diagram showing the results of the Y-maze continuous alternation task test on compound XXIIa.

One-sample t-tests were performed to compare every condition to 50% alternations, i.e. chance level. All the conditions, including vehicle, showed a significant difference from 50% (all Ps<0.001), indicating a well-functioning spatial working memory. A one-way ANOVA comparing the conditions to each other did not yield a significant results ($F_{3,60}$=0.551; n.s.). FIG. 7 gives a graphical overview of the Y-maze alternation performance.

The ketamine/xylazine induced $α_2$-adrenoceptor-mediated anesthesia test, a well-established surrogate measure of emesis in rodents, which are non-vomiting species (Robichaud et al. J. Clin. Invest., 2002, 110:1045), was used to measure emetic properties of XXIIa as summarized in table 5. A shorter anesthesia time than that of the vehicle condition would implicate emetic-like effects. Anesthesia time was calculated relatively to the vehicle condition, which itself was set at 100%, to control for repeated exposure to the test. Concentrations of XXIIa up to a thousand-fold of the effective dosage were tested.

TABLE 5

Mean anesthesia times (+SEM) of the emesis test

| Condition | Time anesthetized | SEM | n |
|---|---|---|---|
| Vehicle | 100.0 | 7.69 | 11 |
| 0.003 mg/kg | 112.28 | 10.24 | 12 |
| 0.03 mg/kg | 109.52 | 6.42 | 12 |
| 0.3 mg/kg | 107.45 | 7.86 | 11 |
| 3.0 mg/kg | 91.22 | 8.79 | 10 |

Displayed are the mean times the mice stayed anesthetized (and their SEMs) during every condition relative to vehicle (set at 100%), as measured during the ketamine/xylazine anesthesia test.

Figure 8:
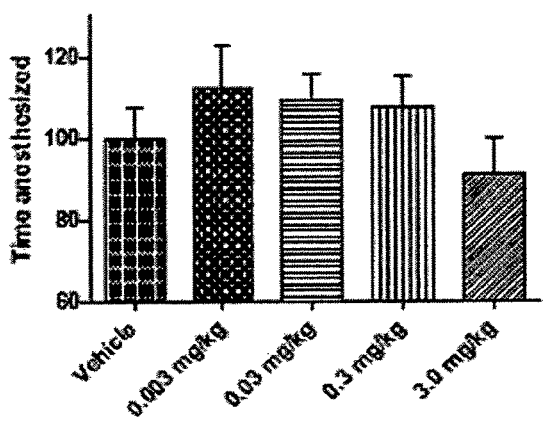
FIG. 8 is a diagram showing the results of the ketamine/xylazine induced $\alpha_2$-adrenoceptor-mediated anesthesia test carried out on compound XXIIa, to measure its emetic properties.

Except with the highest concentration, XXIIa treated animals stayed anesthetized longer than the vehicle condition. A one-way ANOVA comparing all conditions did not show any significant effect ($F_{4,51}$=1.003; n.s.), implying that XXIIa does not have emetic-like effects. A graphical overview of the ketamine/xylazine anesthesia test results are given in FIG. 8.

Pharmacokinetic Studies

A pharmacokinetic analysis has been carried out for compounds XVIIIa, XXIIa and GEBR-7b. by the Center for Drug Metabolism and Pharmacokinetics Research, Shanghai Institute of Materia Medica (Zhangjiang Hi-Tech Park, Pudong, Shanghai, China).

Briefly, a total of 21 male BALB/c mice were used for each drug and three mice were used for each time point. Drugs were dissolved in DMSO, diluted in 0.5% methylcellulose to yield a final concentration of 1 mg/mL and administered subcutaneously at the dose of 10 mg/kg. Blood samples (approximately 250 μL) were collected via retroorbital puncture at 10 min, 20 min, 40 min, 1 h, 2 h, 3 h, and 5 h post-injection. Plasma was separated by centrifugation (11000 rpm, 5 min, 4° C.) and stored at −70° C. before analysis. After blood harvest, mice were sacrificed by cervical dislocation and brains were excised, weighed, rinsed by cold saline and then frozen at −70° C. until analysis.

For blood analysis, aliquot of plasma (25 μL) were added with methanol (25 μL) and with internal standard (25 μL of 500 ng/mL lapatinib for GEBR-7b and XVIIIa, 500 ng/ml voriconazole for XXIIa), followed by the addition of 100 μL methanol.

As for brains, 100 mg of tissue added with 500 μL of methanol and homogenized for approximately 1 min. Homogenized samples were subjected to ultrasound for 10 min and centrifuged at 11000 rpm for 5 min, An aliquot of the homogenized samples (50 for GEBR-7b and XVIIIa, 25 μL for XXIIa) was added with internal standard (20 μL of 500 ng/mL lapatinib for GEBR-7b and XVIIIa, 25 μL of 500 ng/ml voriconazole for XXIIa)

After centrifugation at 11000 rpm for 5 min, a plasma (10 μL for GEBR-7b and XVIIIa, 5 μL for XXIIa) or a brain tissue (20 μL μL for GEBR-7b and XVIIIa, 5 μL for XXIIa) aliquot of the upper layer was injected onto the LC/MS/MS system that consisted of a Shimadztt LC-20A HPLC system (Shiseido, Tokyo, Japan) coupled with a TSQ Quantum Vantage triple quadrupole mass spectrometer equipped with a HESI source (TherrnoFisher, San Jose, Calif., USA). Chromatographic conditions were the following: guard column SecurityGuard $C_{18}$ column (4 mm×3.0 mm I.D., 5 μm, Phenomenex, Torrance, Calif., USA), analytical column SB $C_{18}$ (150 mm×4.6 mm I.D., 5 μm, Agilent, America), buffers 0.1% formic acid in 10 mM ammonium acetate: 0.1% formic acid in methanol 10:90, flow rate 0.6 mL/min. Mass spectrometric conditions were the following: source HESI; scan mode SRM; polarity positive; vaporizer temperature 420° C.; ion sweep gas pressure 1 bar; auxiliary gas pressure 5 bar; capillary temperature 320° C.

Calibration curves were prepared in heparinized blank mice plasma (1-10000 ng/mL) or blank brain homogenate (1-10000 ng/g) using the same internal standards as above.

The pharmacokinetic parameters, calculated by non-compartmental analysis using Phoenix 1.3 (Pharsight USA) were the following: $T_{max}$, the time corresponding to $C_{max}$; $C_{max}$, the maximum observed serum or brain concentration; $t_{1/2}$, the elimination half-life, calculated as $0.693/\lambda_z$, which was obtained by log-linear regression using the terminal points of the serum or brain concentration-time curve; $AUC_{0-t}$, the area under the serum or brain concentration curve from time 0 to the last measurable concentration, calculated by using the linear trapezoidal rule. The $AUC_{0-t}$ brain to plasma ratios represent an index of blood brain barrier penetration. All data have been reported in Table 6. As it is clearly shown, there is a significant increase in brain penetration from GEBR-7b to compound XXIIa.

TABLE 6

| Parameters | Compds | | | | | |
|---|---|---|---|---|---|---|
| | GEBR-7b | | XVIIIa | | XXIIa | |
| | Plasma | Brain | Plasma | Brain | Plasma | Brain |
| Tmax (h) | 0.17 | 0.17 | 0.17 | 0.17 | 0.33 | 0.33 |
| Cmax (ng/mL or g) | 4406 | 1567 | 2157 | 936 | 993 | 2608 |
| $t_{1/2}$ (h) | 0.70 | 1.36 | 0.82 | 0.54 | 0.95 | 0.95 |
| $AUC_{0-t}$ (ng · h/mL or g) | 1225 | 391 | 1893 | 812 | 861 | 2330 |
| $AUC_{0-t}$ ratio (Brain/Plasma) | 0.32 | | 0.75 | | 2.71 | |

The invention claimed is:

1. A compound of formula (I):

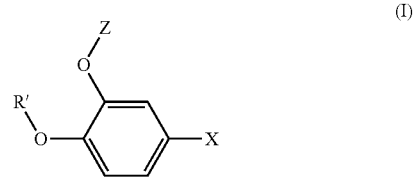

(I)

wherein:

Z=cyclopentyl;

R'=—$CH_3$ or $CHF_2$;

X=

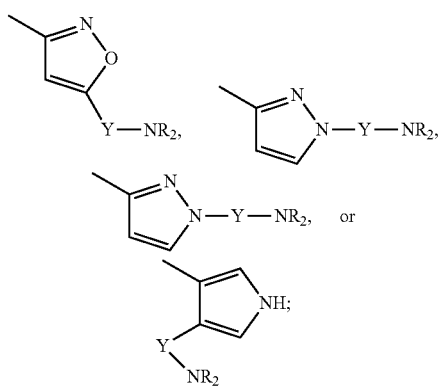

Y=—CO, —C=O($CH_2$), —CH(OH)—$CH_2$, —$CH_2$—C=O, —$CH_2$—$CH_2$—C=O, —$CH_2$—CH(OH)—$CH_2$, or —$CH_2$—CH($OCOR_1$)—$CH_2$;

$NR_2$=—N($CH_2$—$CH_2OH$)$_2$,

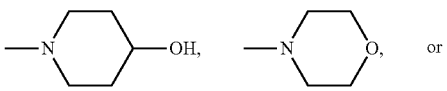

or

-continued

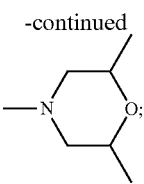

and
R₁=C₁-C₃ alkyl,
and enantiomers, diastereoisomers, and pharmaceutically acceptable salts thereof.

2. A compound according to claim 1, wherein X =

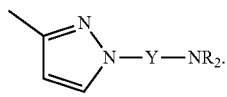

3. A compound according to claim 1, having the formula:
1-{3-[3-(Cyclopentyloxy)-4-methoxyphenyl]isoxazol-5-yl}-2-morpholin-4-ylethanone hydrochloride;
1-{3-[3-(Cyclopentyloxy)-4-methoxyphenyl]isoxazol-5-yl}-2-(2,6-dimethylmorpholin-4-yl)ethanone hydrochloride;
1-{3-[3-(Cyclopentyloxy)-4-methoxyphenyl]isoxazol-5-yl}-2-morpholin-4-ylethanol;
1-{3-[3-(Cyclopentyloxy)-4-methoxyphenyl]isoxazol-5-yl}-2-(2,6-dimethylmorpholin-4-yl)ethanol;
4-({3-[3-(Cyclopentyloxy)-4-methoxyphenyl]isoxazol-5-yl}carbonyl)morpholine;
4-({3-[3-(Cyclopentyloxy)-4-methoxyphenyl]isoxazol-5-yl}carbonyl)-2,6-dimethylmorpholine;
1-{3-[3-(Cyclopentyloxy)-4-methoxyphenyl]-1H-pyrazol-1-yl}-3-morpholin-4-ylpropan-2-ol dihydrochloride;
1-{3-[3-(Cyclopentyloxy)-4-methoxyphenyl]-1H-pyrazol-1-yl}-3-(2,6-dimethylmorpholin-4-yl) propan-2-ol dihydrochloride;
1(3-{3-[3-(Cyclopentyloxy)-4-methoxyphenyl]-1H-pyrazol-1-yl}-2-hydroxypropyl)piperidin-4-ol;
2-{3-[3-(cyclopentyloxy)-4-methoxyphenyl]-1H-pyrazol-1-yl}-1-(morpholin-4-ylmethyl)ethyl acetate;
4-({3-[3-(Cyclopentyloxy)-4-methoxyphenyl]-1H-pyrazol-1-yl}acetyl)morpholine;
4-({3-[3-(Cyclopentyloxy)-4-methoxyphenyl]-1H-pyrazol-1-yl}acetyl)-2,6-dimethylmorpholine;
4-(3-{3-[3-(Cyclopentyloxy)-4-methoxyphenyl]-1H-pyrazol-1-yl}propanoyl)morpholine;
4-(3-{3-[3-(Cyclopentyloxy)-4-methoxyphenyl]-1H-pyrazol-1-yl}propanoyl)-2,6-dimethylmorpholine;
4-(3-{3-[3-(cyclopentyloxy)-4-(difluoromethoxy)phenyl]-1H-pyrazol-1-yl}propanoyl)morpholine;
2-{3-[3-(cyclopentyloxy)-4-methoxy-phenyl]-pyrrol-1-yl}-1-morpholin-4-yl-ethanone;
2-{3-[3-(Cyclopentyloxy)-4-methoxy-phenyl]-pyrrol-1-yl}-1-(2,6-dimethyl-morpholin-4-yl)-ethanone;
2-{3-[3-(Cyclopentyloxy)-4-methoxy-phenyl]-pyrrol-1-yl}-1-(4-hydroxy-piperidin-1-yl)-ethanone;
3-{3-[3-(cyclopentyloxy)-4-methoxy-phenyl]-pyrrol-1-yl}-1-morpholin-4-yl-propan-1-one;
3-{3-[3-(Cyclopentyloxy)-4-methoxy-phenyl]-pyrrol-1-yl}-1-(4-hydroxy-piperidin-1-yl)-propan-1-one;
1-{3-[3-(Cyclopentyloxy)-4-methoxy-phenyl]-pyrrol-1-yl}-3-morpholin-4-yl-propan-2-ol;
1-{3-[3-(Cyclopentyloxy)-4-methoxy-phenyl]-pyrrol-1-yl}-3-(2,6-dimethyl-morpholin-4-yl)-propan-2-ol;
1-(3-{3[3-(cyclopentyloxy)-4-methoxy-phenyl]-pyrrol-1-yl}-2-hydroxy-propyl)-piperidin-4-ol;
{4-[3-(Cyclopentyloxy)-4-methoxy-phenyl]-1H-pyrrol-3-yl}-morpholin-4-yl-methanone;
{4-[3-(Cyclopentyloxy)-4-methoxy-phenyl]-1H-pyrrol-3-yl}-(2,6-dimethyl-morpholin-4-yl)-methanone; or
{4-[3-(Cyclopentyloxy)-4-methoxy-phenyl]-1H-pyrrol-3-yl}-(4-hydroxy-piperidin-1-yl)-methanone.

4. A pharmaceutical composition comprising a compound according to claim 1 and a pharmaceutically acceptable carrier.

5. A process for the preparation of a compound of formula (I):

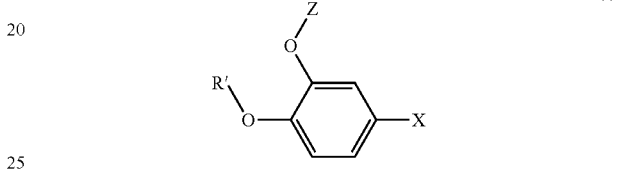

wherein:
Z=cyclopentyl;
R'=—CH₃ or CHF₂;
X=

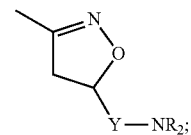

Y=—CH₂—C=O; and
NR₂=—N(CH₂—CH₂OH)₂,

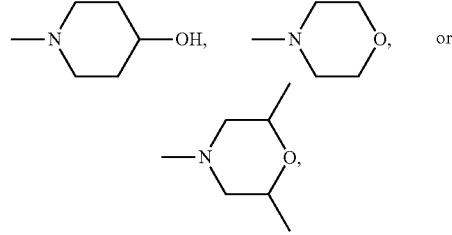

comprising reacting a compound of formula (II):

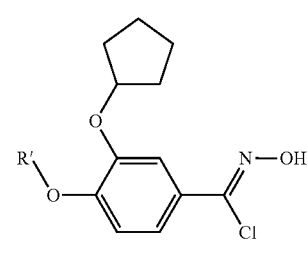

with a compound of formula (III):

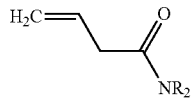

to yield the compound of formula (Ia):

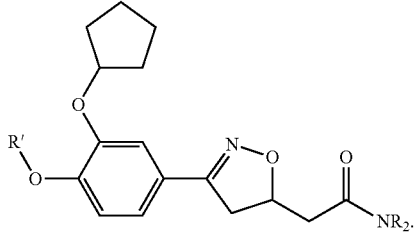

6. A process for the preparation of a compound according to claim 1, wherein:
X=

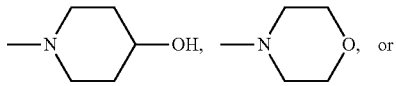

Y=—C=O; and
NR$_2$ =—N(CH$_2$—CH$_2$OH)$_2$,

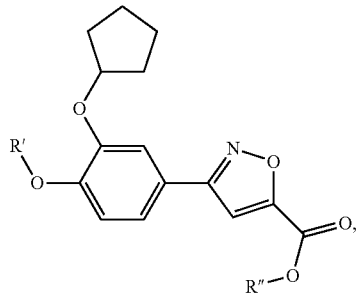

comprising reacting a compound of formula (V):

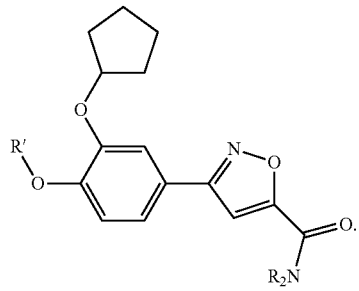

wherein R″ is C$_1$-C$_4$alkyl, with R$_2$NH, to yield the compound of formula (Ic):

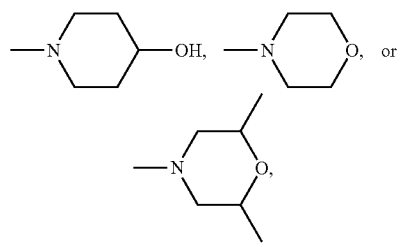

7. A process for the preparation of a compound according to claim 1, wherein:
X=

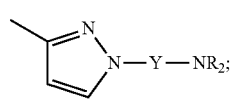

Y=—CH$_2$—CH(OH)—CH$_2$; and
NR$_2$=—N(CH$_2$—CH$_2$OH)$_2$,

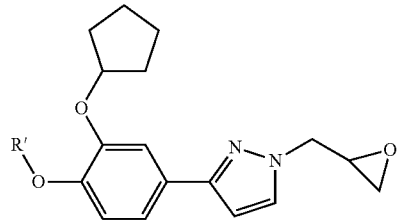

comprising reacting a compound of formula (VI):

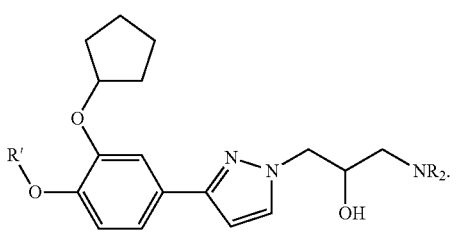

with R$_2$NH to yield:

(Id)

8. The process according to claim 7, wherein R' is —CHF$_2$ and the corresponding intermediate compound of formula (VIa) is prepared according to the reaction scheme:

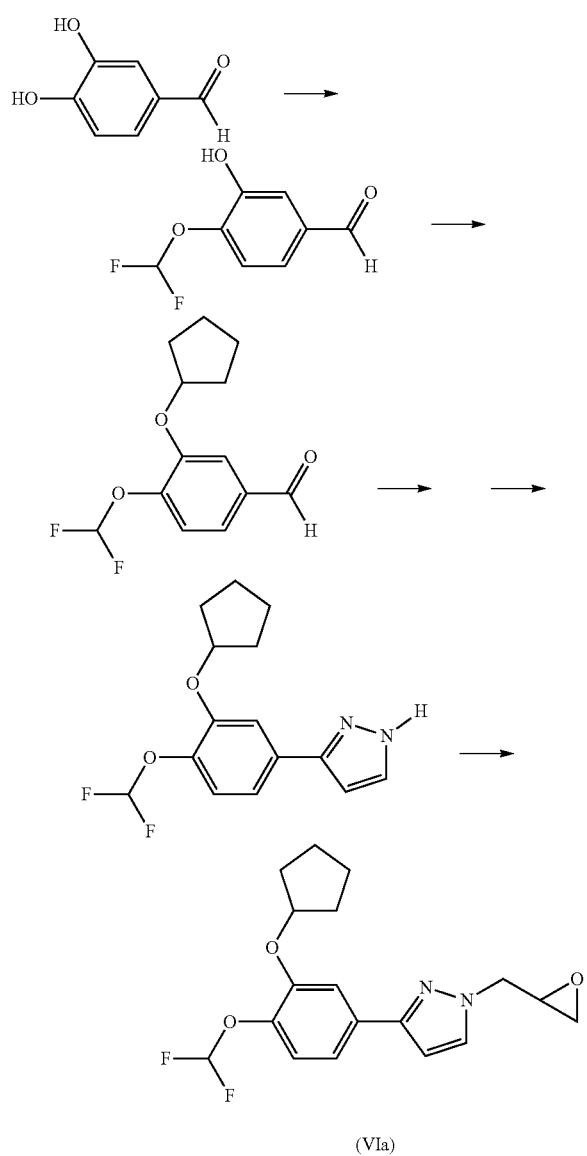

(VIa)

wherein the first step of converting 3,4-dihydroxybenzaldehyde into 3,4-(difluoromethoxy)-hydroxybenzaldehyde involves the reaction of 3,4-dihydroxybenzaldehyde with an ester of chlorodifluoroacetic acid in the presence of Cs$_2$CO$_3$ under irradiation with microwaves at a potency lower or equal to 300 W.

9. A process for the preparation of a compound according to claim 1, wherein:

X=

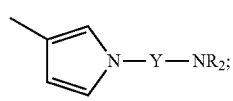

and
Y=—CH$_2$—C=O or —CH$_2$—CH$_2$—C=O, comprising reacting a compound of formula (VII):

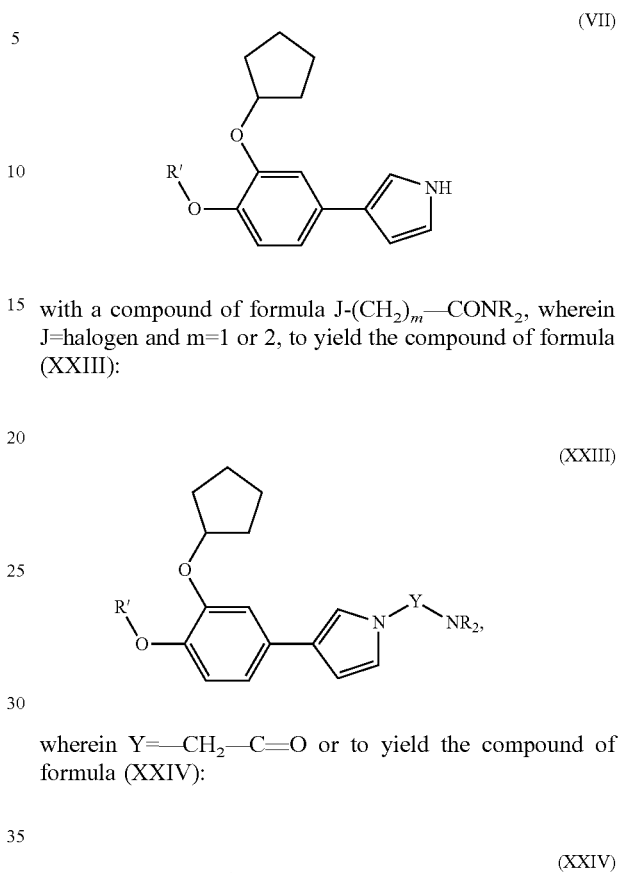

with a compound of formula J-(CH$_2$)$_m$—CONR$_2$, wherein J=halogen and m=1 or 2, to yield the compound of formula (XXIII):

(XXIII)

wherein Y=—CH$_2$—C=O or to yield the compound of formula (XXIV):

(XXIV)

wherein Y=—CH$_2$—CH$_2$—C=O.

10. A process for the preparation of a compound according to claim 1, wherein:

X=

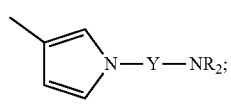

Y=CH$_2$—CH(OH)—CH$_2$; and
NR$_2$=—N(CH$_2$—CH$_2$OH)$_2$,

—N⟩—OH, —N⟩O, or

-continued
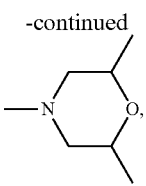
comprising reacting a compound of formula (VIII):
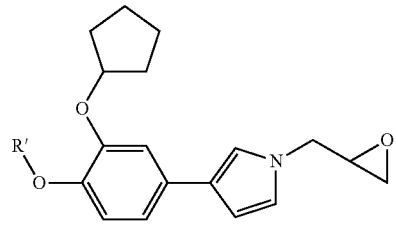
(VIII)
with R₂NH to yield the compound of formula (XXV):
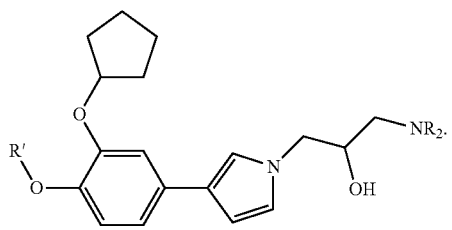
(XXV)
11. A process for the preparation of a compound according to claim 1, wherein:
X=
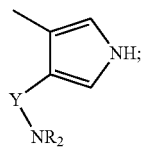
Y=—CO; and
NR₂=N(CH₂—CH₂OH)₂,
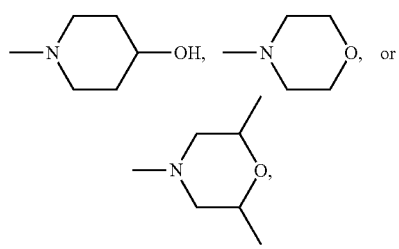
comprising reacting a compound of formula (IX):
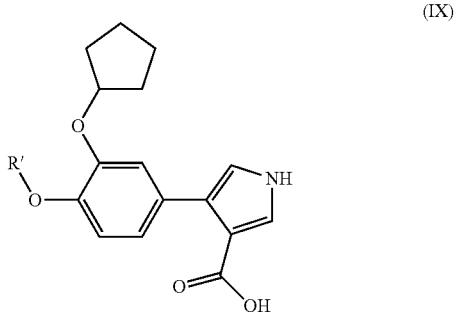
(IX)
with R₂NH to yield:
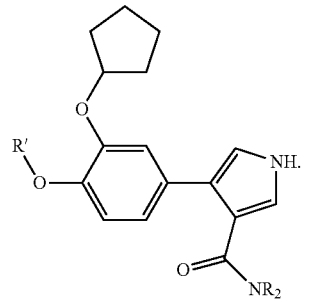
(XXVI)
12. The process according to claim 9, wherein J=Br or Cl.
* * * * *